(12) United States Patent
Wang et al.

(10) Patent No.: US 9,700,633 B2
(45) Date of Patent: Jul. 11, 2017

(54) CONJUGATES OF WATER SOLUBLE POLYMER-AMINO ACID OLIGOPEPTIDE-DRUG, PREPARATION METHOD AND USE THEREOF

(71) Applicant: JENKEM TECHNOLOGY CO. LTD., TIANJIN BRANCH, Tianjin (CN)

(72) Inventors: Jinliang Wang, Tianjin (CN); Xuan Zhao, Tianjin (CN); Zhenguo Wang, Tianjin (CN); Zewang Feng, Tianjin (CN); Jianhuan Jia, Tianjin (CN)

(73) Assignee: JENKEM TECHNOLOGY CO., LTD., TIANJIN BRANCH, Teda Development Zone, Tianjin (CN)

( * ) Notice: Subject to any disclaimer, the term of this patent is extended or adjusted under 35 U.S.C. 154(b) by 0 days.

(21) Appl. No.: 14/764,166

(22) PCT Filed: Jan. 24, 2014

(86) PCT No.: PCT/CN2014/071395
§ 371 (c)(1),
(2) Date: Jul. 28, 2015

(87) PCT Pub. No.: WO2014/114262
PCT Pub. Date: Jul. 31, 2014

(65) Prior Publication Data
US 2015/0359900 A1    Dec. 17, 2015

(30) Foreign Application Priority Data

Jan. 28, 2013 (CN) .......................... 2013 1 0032635
Jun. 18, 2013 (CN) .......................... 2013 1 0241907
Dec. 2, 2013 (CN) .......................... 2013 1 0632830

(51) Int. Cl.

| | |
|---|---|
| *A61K 47/48* | (2006.01) |
| *A61K 31/436* | (2006.01) |
| *A61K 31/4745* | (2006.01) |
| *A61K 31/506* | (2006.01) |
| *A61K 31/00* | (2006.01) |
| *A61K 31/337* | (2006.01) |
| *A61K 31/44* | (2006.01) |
| *A61K 31/517* | (2006.01) |
| *A61K 31/5377* | (2006.01) |
| *A61K 31/585* | (2006.01) |

(52) U.S. Cl.
CPC ........ *A61K 47/48246* (2013.01); *A61K 31/00* (2013.01); *A61K 31/337* (2013.01); *A61K 31/436* (2013.01); *A61K 31/44* (2013.01); *A61K 31/4745* (2013.01); *A61K 31/506* (2013.01); *A61K 31/517* (2013.01); *A61K 31/5377* (2013.01); *A61K 31/585* (2013.01); *A61K 47/48215* (2013.01)

(58) Field of Classification Search
CPC ........ A61K 47/48246; A61K 47/48215; A61K 31/506; A61K 31/436; A61K 31/4745; A61K 31/00; A61K 31/337; A61K 31/44; A61K 31/517; A61K 31/5377; A61K 31/585
See application file for complete search history.

(56) References Cited

U.S. PATENT DOCUMENTS

| 6,566,506 B2 | 5/2003 | Greenwald et al. |
| 2005/0147617 A1* | 7/2005 | Ji .................... A61K 47/48338 424/178.1 |
| 2011/0286956 A1 | 11/2011 | Zhao et al. |
| 2012/0282671 A1 | 11/2012 | Zhao et al. |

FOREIGN PATENT DOCUMENTS

| CN | 1283643 A | 2/2001 |
| CN | 1442440 A | 9/2003 |
| CN | 1556828 A | 12/2004 |

(Continued)

OTHER PUBLICATIONS

Machine translation of WO 2005/092898 A1, pp. 1-23, accessed Nov. 3, 2016.*
"International Search Report for PCT/CN2014/071395", May 19, 2014.

*Primary Examiner* — Julie Ha
*Assistant Examiner* — Li Ni Komatsu
(74) *Attorney, Agent, or Firm* — Jun He Law Offices P.C.; James J. Zhu

(57) ABSTRACT

A conjugate of water soluble polymer-amino acid oligopeptide-drug of Formula (I) below and a pharmaceutical composition comprising the conjugate are provided. In the conjugate, P is a water soluble polymer; X is a linking group, wherein the linking group links P and $A_1$; each of $A_1$, $A_2$ and $A_3$ is independently same or different amino acid residue or amino acid analogue residue; each of $D_1$ and $D_2$ is independently same or different drug molecule residue; a is 0 or 1; b is an integer of 2-12; c is an integer of 0-7; d is 0 or 1. The conjugate could improve drug load capacity, water solubility, stability and activity of the drug.

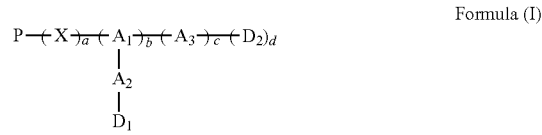

Formula (I)

24 Claims, 2 Drawing Sheets

(56) References Cited

FOREIGN PATENT DOCUMENTS

| | | | |
|---|---|---|---|
| CN | 1611524 A | 5/2005 | |
| CN | WO 2005/092898 A1 * | 10/2005 | ............ A61K 31/34 |
| CN | 1706865 A | 12/2005 | |
| CN | 1756758 A | 4/2006 | |
| CN | 1840201 A | 10/2006 | |
| CN | 101104078 A | 1/2008 | |
| CN | 102145178 A | 8/2011 | |
| CN | 102766258 A | 11/2012 | |
| WO | 2010120387 A1 | 10/2010 | |

* cited by examiner

CONJUGATES OF WATER SOLUBLE POLYMER-AMINO ACID OLIGOPEPTIDE-DRUG, PREPARATION METHOD AND USE THEREOF

CROSS REFERENCE TO RELATED APPLICATIONS

This application claims the benefit of priority to Chinese application No. 201310032635.5, filed on Jan. 28, 2013, and Chinese application No. 201310241907.2, filed on Jun. 18, 2013, and Chinese application No. 201310632830.1, filed on Dec. 2, 2013, the disclosures of which are hereby incorporated by reference in their entirety.

TECHNICAL FIELD

The present invention provides a conjugate of water soluble polymer-amino acid oligopeptide-drug and pharmaceutical composition thereof, method of preparing the conjugate and the composition and use thereof. The conjugate improves the effect of medicament on treating diseases by increasing the load capacity of active drugs. In addition, the stability of the conjugate is improved dramatically.

BACKGROUND ART

It is an important issue in pharmacy to deliver drugs at effective concentration to action sites with good stability and low toxicity. It can increase water solubility of a medicament by coupling the medicament to a water soluble polymer, such as polyethylene glycol (PEG). However, one shortcoming of the conventional PEG modification technique is that, in general, the medicament or other functional group could only link to two terminal ends of the PEG molecule, which remarkably limits the drug load capacity of the PEG carrier.

Therefore, it is still a problem to be solved of how to find a nontoxic carrier and administration method thereof which could increase water solubility and stability of the drug and reduce side effects of toxicity, and possess high drug load capacity. The present invention is directed to solving the problem.

SUMMARY OF THE INVENTION

The present invention provides a conjugate of water soluble polymer-amino acid oligopeptide-drug, which has the structure shown in Formula (I) below:

$$P\text{-}(X)_a\text{-}(A_1)_b\text{-}(A_3)_c\text{-}(D_2)_d \qquad \text{Formula (I)}$$
$$\quad\quad\quad\quad\quad | $$
$$\quad\quad\quad\quad\quad A_2$$
$$\quad\quad\quad\quad\quad |$$
$$\quad\quad\quad\quad\quad D_1$$

wherein, P is a water soluble polymer;
X is a linking group, wherein the linking group links P and $A_1$;
each of $A_1$, $A_2$ and $A_3$ is independently same or different amino acid residue or amino acid analogue residue;
each of $D_1$ and $D_2$ is independently same or different drug molecule residue;
a is 0 or 1;
b is an integer of 2-12;
c is an integer of 0-7;
d is 0 or 1.

In some embodiments, P is selected from a group consisting of PEG, polypropylene glycol, polyglutamic acid, poly(aspartic acid), polyvinylpyrrolidone, polyvinyl alcohol, polypropylene morpholine, glucan, carboxymethylcellulose and analogue or copolymer thereof.

In some embodiments, P is PEG with molecular weight of 300-60,000. In some embodiments, the molecular weight of PEG is 20,000-40,000. In some embodiments, the molecular weight of PEG is 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, or 40,000.

In some embodiments, PEG is linear, Y type branched or multi-arm PEG.

In some embodiments, PEG has the structure shown in Formula (II) below:

$$R_1\text{-}O\text{-}(CH_2CH_2O)_e \qquad \text{Formula (II)}$$

wherein, the $R_1$ is $C_{1-12}$ alkyl, $C_{1-12}$ heteroalkyl, hydrogen or arylalkyl, e is an integer of 10-1,500.

In some embodiments, P has the structure shown in Formula (III) below:

$$\begin{array}{l}R_2\text{—}O\text{-}(CH_2CH_2O)_f\text{—}R_4\\ \qquad\qquad\qquad\qquad\qquad\quad\;\backslash\\ \qquad\qquad\qquad\qquad\qquad\quad\;\;N\text{—}\\ \qquad\qquad\qquad\qquad\qquad\quad\;/\\ R_3\text{—}O\text{-}(CH_2CH_2O)_g\text{—}R_5\end{array} \qquad \text{Formula (III)}$$

wherein each of $R_2$ and $R_3$ is independently $C_{1-12}$ alkyl, $C_{1-12}$ heteroalkyl, hydrogen, or arylalkyl;
each of $R_4$ and $R_5$ is independently $C_{1-12}$ alkyl, or $C_{1-12}$ alkylcarbonyl;
each of f and g is independently an integer of 10-1,500.

In some embodiments, $R_2$ and $R_3$ in Formula (III) are cyclopropyl, cyclobutyl, cyclohexyl or benzyl.

In some embodiments, $R_2$ and $R_3$ in Formula (III) are methyl, $R_4$ is ethyl, and $R_5$ is methylenecarbonyl.

In some embodiments, P has a structure shown in Formula (IV) below:

$$R_6\text{-}[O\text{-}(CH_2CH_2O)_h]_i \qquad \text{Formula (IV)}$$

wherein $R_6$ is a residue of pentaerythritol, methylglucoside, sucrose, diethylene glycol, propanediol, glycerol or polyglycerol whose hydrogen in the hydroxyl group is removed; i is 3, 4, 6 or 8; h is an integer of 10-1,500.

In some embodiments, X is $(CH_2)_n$, $(CH_2)_nCO$, $(CH_2)_nOCO$, $(CH_2)_nNHCO$, $-S-$, $-SO_2-$, or $-SO_4-$; n is an integer of 1-12. In some embodiments, X is $CH_2CO$.

In some embodiments, $A_1$ is an amino acid residue or an amino acid analogue residue which has at least two carboxylic groups and one amino group.

In some embodiments, $A_1$ has a structure shown in Formula (V) below:

$$\begin{array}{c}\quad\quad\quad\quad\;\;O\\ \quad\quad\quad\quad\;\;\|\\ \text{—}NH\text{—}R_7\text{—}C\text{—}\\ \quad\quad\quad\quad\;|\\ \quad\quad\quad O=C\\ \quad\quad\quad\quad\;\;|\end{array} \qquad \text{Formula (V)}$$

wherein $R_7$ is $C_{1-20}$ alkyl or $C_{1-20}$ heteroalkyl. In some embodiments, $R_7$ is methyl, ethyl, propyl, butyl, pentyl, hexyl, heptyl, octyl, nonyl, decyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl, $C_{18}$ alkyl, $C_{19}$ alkyl or $C_{20}$ alkyl. Carbonyl group in Formula (V) could link to any carbon of $R_7$. In some embodiments, $R_7$ is linear alkyl or heteroalkyl. In some embodiments, $R_7$ is branched alkyl or heteroalkyl.

In some embodiments, $A_1$ has a structure shown in Formula (VI) below:

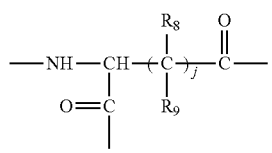

Formula (VI)

wherein each of $R_8$ and $R_9$ is independently hydrogen, $C_{1-12}$ alkyl, $C_{1-12}$ heteroalkyl, aryl, heteroaryl, aralkyl or heteroarylalkyl, and $R_8$ and $R_9$ in each repeat unit could be same or different; j is an integer of 1-10.

In some embodiments, $A_1$ is an aspartic acid residue or glutamic acid residue.

In some embodiments, $A_2$, $A_3$ independently has a structure shown in Formula (VII) below:

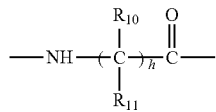

Formula (VII)

wherein, each of $R_{10}$ and $R_{11}$ is independently hydrogen, $C_{1-6}$ alkyl, or $C_{1-6}$ heteroalkyl, and $R_{10}$ and $R_{11}$ in each repeat unit could be same or different; h is an integer of 1-10. In some embodiments, each of $R_{10}$ and $R_{11}$ is independently methyl, ethyl, propyl, butyl, pentyl, hexyl. In some embodiments, each of $R_{10}$ and $R_{11}$ is independently linear alkyl or heteroalkyl. In some embodiments, each of $R_{10}$ and $R_{11}$ is independently branched alkyl or heteroalkyl.

In some embodiments, each of $A_2$ and $A_3$ is independently the residue of glycine, alanine, leucine, isoleucine, valine, proline, phenylalanine, methionine, serine, threonine, cysteine and tyrosine. In some embodiments, $A_2$ and $A_3$ are valine.

In some embodiments, $D_1$ and $D_2$ is independently residue of anti-tumor drug. In some embodiments, the residue of anti-tumor drug could form peptide or ester bond with $A_2$ or $A_3$. In some embodiments, after modification, the anti-tumor drug could form peptide or ester bond with $A_2$ or $A_3$. In some embodiments, the anti-tumor drug is dasatinib, rapamycin, elomotecan, imatinib, erlotinib, gefitinib, lapatinib, sorafenib, sunitinib, paclitaxel, camptothecin, cinobufagin, glycyrrhetinic acid, or scopoletin. In some embodiments, the anti-tumor drug is dasatinib.

In some embodiments, the present application provides a conjugate with a structure shown in Formula (VIII) below:

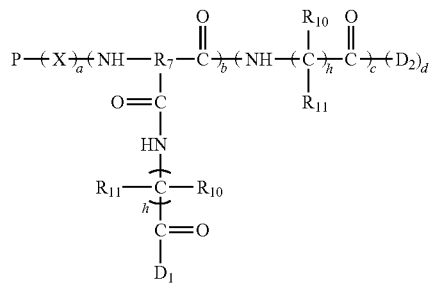

Formula (VIII)

wherein $R_7$ is $C_{1-20}$ alkyl, each of $R_{10}$ and $R_{11}$ is independently hydrogen, or $C_{1-6}$ alkyl, and $R_{10}$ and $R_{11}$ in each repeat unit could be same or different; h is an integer of 1-10. P, X, a, b, c, d, $D_1$, and $D_2$ are same as described above.

In some embodiments, the present application provides a conjugate with a structure shown in Formulas (IX), (X), or (XI) below:

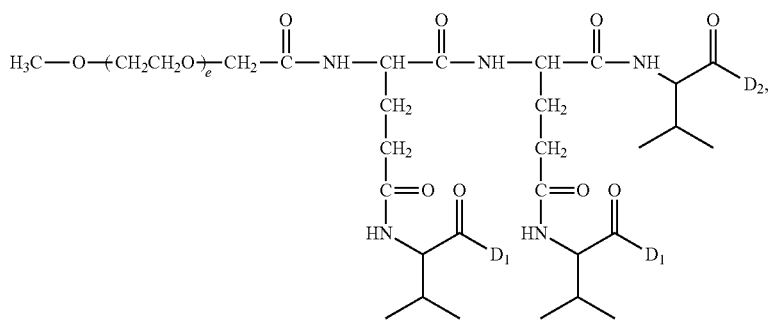

Formula (IX)

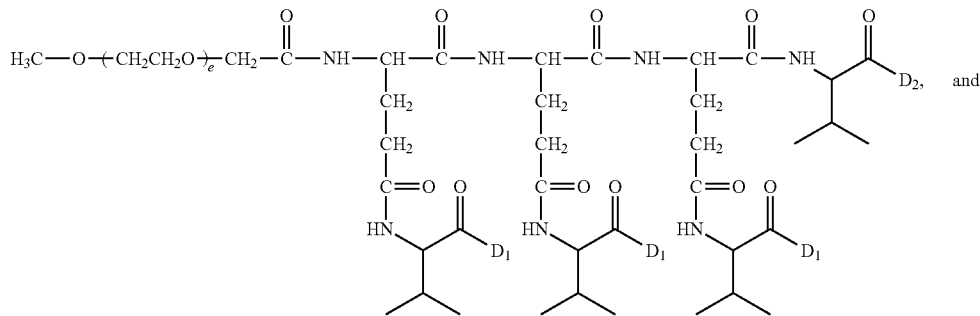

Formula (X)

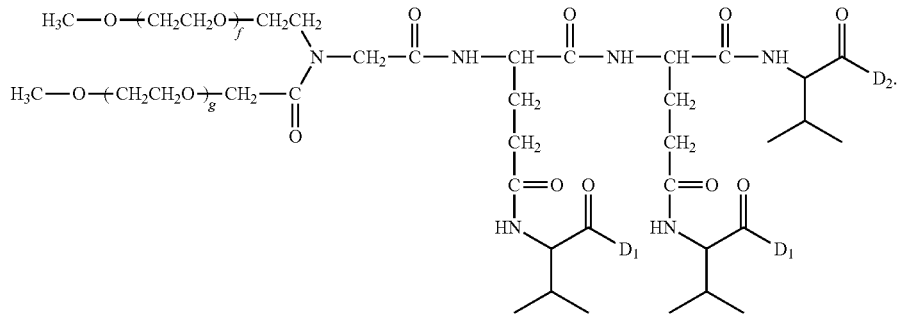

Formula (XI)

wherein each of e, f and g is independently an integer of 10-1,500. D1 and D2 are same as described above. $D_1$ and $D_2$ are the same drug.

In some embodiments, the present application provides a pharmaceutical composition comprising the conjugate above and a pharmaceutically acceptable carrier or excipient.

In some embodiments, the pharmaceutical composition is in the form of tablet, capsule, pill, granules, powder, suppository, injection, solution, suspension, ointment, patch, lotion, drop, liniment, spray.

In some embodiments, the present application provides use of the conjugate and/or pharmaceutical composition in the manufacture a medicament for treating tumor, fungal infection, rheumatoid arthritis, multiple sclerosis, heart valve restenosis or pneumonia.

In some embodiments, the anti-tumor medicament is for treating diseases selected from the group consisting of: leukemia, acute myelocytic leukemia, chronic myelocytic leukemia, chronic lymphocytic leukemia, acute lymphocytic leukemia, myelodysplasia, multiple myeloma, Hodgkin's disease or non-Hodgkin's disease, small cell lung cancer or non-small cell lung cancer, stomach cancer, colon cancer, esophageal cancer, colorectal cancer, prostate cancer, ovarian cancer, breast cancer, brain cancer, urinary tract cancer, kidney cancer, bladder cancer, malignant melanoma, liver cancer, uterine cancer, pancreas cancer, myeloma cancer, endometrial cancer, head and neck cancer, pediatric tumors, sarcomas.

In some embodiments, the present application provides a method for treating tumor, fungal infection, rheumatoid arthritis, multiple sclerosis, heart valve restenosis or pneumonia in a subject, the method comprising administrating the subject a therapeutically effective amount of the conjugate or pharmaceutical composition. In some embodiments, the subject is mammal. In some embodiments, the subject is human.

In some embodiments, the administration methods of the conjugate and/or pharmaceutical composition above include oral, mucosal, sublingual, ocular, topical, parenteral, rectal, intracisternal, vagina, peritoneum, bladder, or nasal administration.

In some embodiments, the present application provides a method for preparing the conjugate above, the method comprising:

forming the conjugate(s) $D_1$-$A_2$ and/or $D_2$-$A_3$ through esterification or amidation reaction between a drug molecule and an amino acid;

forming the compound of Formula (I) through amidation reaction between the conjugate(s) $D_1$-$A_2$ and/or $D_2$-$A_3$ and the compound P-(X)$_a$-(A$_1$)$_b$.

Other features and advantages of the present invention can be found in the detailed description below. The following examples and specific embodiments are intended to clarify technical solutions and advantages of the present invention, and do not intend to limit the scope of the invention.

DETAILED DESCRIPTION OF THE INVENTION

Figure 1:
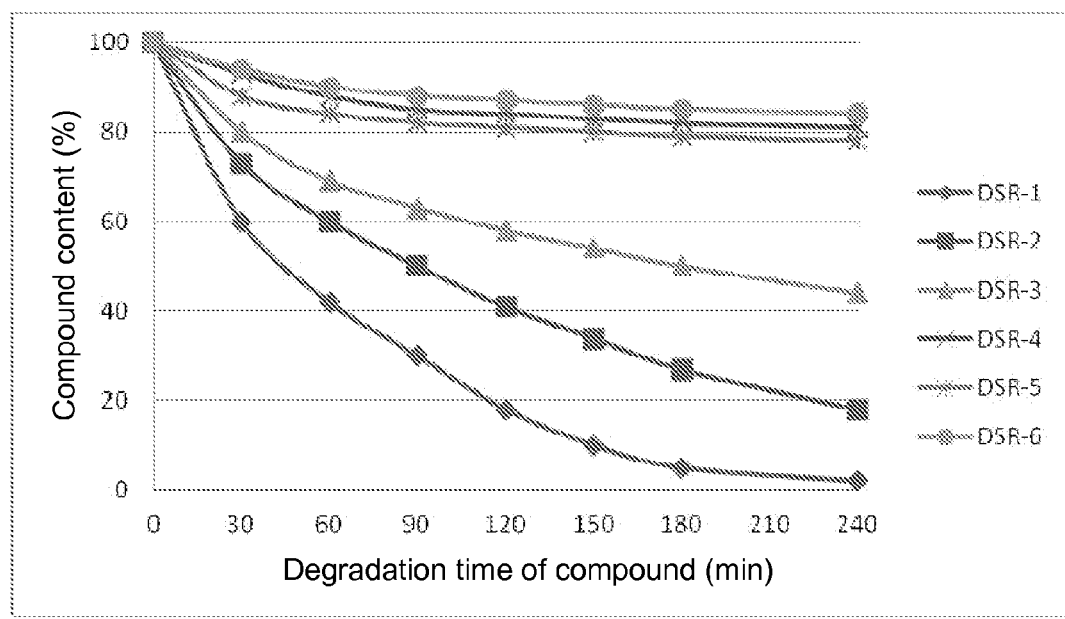
FIG. 1 shows degradation of the compound DSR1-6 in 0.01 M PBS buffer solution. DSR-1 is mPEG-dipeptide acid-dasatinib ester (20K), DSR-2 is mPEG-glycine dipeptide-dasatinib ester (20K), DSR-3 is mPEG-alanine dipeptide-dasatinib ester (20K), DSR-4 is mPEG-valine dipeptide-dasatinib ester (20K), DSR-5 is Y-PEG-valine dipeptide-dasatinib ester (30K), and DSR-6 is mPEG-valine tripeptide-dasatinib ester (40K).

Structure of the Conjugate of Water Soluble Polymer-Amino Acid Oligopeptide-Drug In one aspect, the conjugate of water soluble polymer-amino acid oligopeptide-drug of the present invention has a structure shown in Formula (I) below

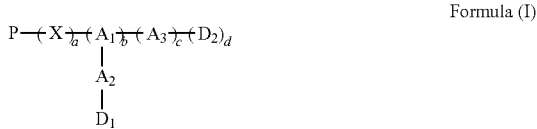

Formula (I)

wherein P is a water soluble polymer; X is a linking group which links P and $A_1$; each of $A_1$, $A_2$ and $A_3$ is independently same or different amino acid residue or amino acid analogue residue; each of $D_1$ and $D_2$ is independently same or different drug molecule residue; a is 0 or 1; b is an integer of 2-12; c is an integer of 0-7; d is 0 or 1.

The water soluble polymer refers to a polymer formed by linking compounds comprising polar or charged functional groups, and the polymer is water soluble, i.e. the polymer is hydrophilic. The water soluble polymer includes but not limited to: PEG, polypropylene glycol, polyglutamic acid, poly(aspartic acid), polyvinylpyrrolidone, polyvinyl alcohol, polypropylene morpholine, glucan, carboxymethylcellulose and analogue or copolymer thereof.

In some embodiments of the present invention, P is PEG with a molecular weight of 300-60,000. In some embodiments, the molecular weight of PEG is 20,000-40,000. In some embodiments, the molecular weight of PEG is 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000.

In some embodiments, the PEG is linear, Y type branched or multi-arm PEG.

In some embodiments, the PEG has a structure shown in Formula (II) below:

Formula (II)

wherein $R_1$ is $C_{1-12}$ alkyl, $C_{1-12}$ heteroalkyl, hydrogen, or arylalkyl, e is an integer of 10-1,500. In some embodiments, e is an integer of 100-1,400. In some embodiments, e is an integer of 200-1,300. In some embodiments, e is an integer of 300-1,200. In some embodiments, e is an integer of 400-1,100. In some embodiments, e is an integer of 500-1,000. In some embodiments, e is 600, 700, 800, 900 or 1,000. Preferably, $R_1$ is $C_{1-10}$ alkyl. More preferably, $R_1$ is $C_{1-8}$ alkyl. More preferably, $R_1$ is $C_{1-6}$ alkyl. More preferably, $R_1$ is $C_{1-5}$ alkyl. More preferably, $R_1$ is $C_{1-4}$ alkyl. More preferably, $R_1$ is $C_{1-3}$ alkyl. More preferably, $R_1$ is $C_{1-2}$ alkyl. In some embodiments, $R_1$ is methyl, ethyl, propyl, butyl, or pentyl.

In some embodiments, P has a structure shown in Formula (III) below:

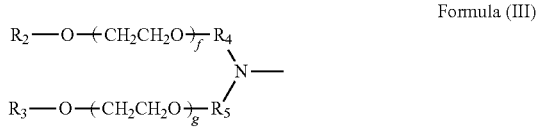

Formula (III)

wherein each of $R_2$ and $R_3$ is independently $C_{1-12}$ alkyl, $C_{1-12}$ heteroalkyl, hydrogen, arylalkyl; preferably, each of $R_2$ and $R_3$ is independently $C_{1-10}$ alkyl. More preferably, each of $R_2$ and $R_3$ is independently $C_{1-8}$ alkyl. More preferably, each of $R_2$ and $R_3$ is independently $C_{1-6}$ alkyl. More preferably, each of $R_2$ and $R_3$ is independently $C_{1-5}$ alkyl. More preferably, each of $R_2$ and $R_3$ is independently $C_{1-4}$ alkyl. More preferably, each of $R_2$ and $R_3$ is independently $C_{1-3}$ alkyl. More preferably, each of $R_2$ and $R_3$ is independently $C_{1-2}$ alkyl. In some embodiments, each of $R_2$ and $R_3$ is independently methyl, ethyl, propyl, butyl, or pentyl.

Each of $R_4$ and $R_5$ is independently $C_{1-12}$ alkyl, $C_{1-12}$ alkylcarbonyl. Preferably, each of $R_4$ and $R_5$ is independently $C_{1-10}$ alkyl, $C_{1-10}$ alkylcarbonyl. More preferably, each of $R_4$ and $R_5$ is independently $C_{1-8}$ alkyl, $C_{1-8}$ alkylcarbonyl. More preferably, each of $R_4$ and $R_5$ is independently $C_{1-6}$ alkyl, $C_{1-6}$ alkylcarbonyl. More preferably, each of $R_4$ and $R_5$ is independently $C_{1-5}$ alkyl, $C_{1-5}$ alkylcarbonyl. More preferably, each of $R_4$ and $R_5$ is independently $C_{1-4}$ alkyl, $C_{1-4}$ alkylcarbonyl. More preferably, each of $R_4$ and $R_5$ is independently $C_{1-3}$ alkyl, $C_{1-3}$ alkylcarbonyl. More preferably, each of $R_4$ and $R_5$ is independently $C_{1-2}$ alkyl, $C_{1-2}$ alkylcarbonyl.

Each of f and g is independently an integer of 10-1,500. In some embodiments, each of f and g is independently an integer of 100-1,400. In some embodiments, each of f and g is independently an integer of 200-1,300. In some embodiments, each of f and g is independently an integer of 300-1,200. In some embodiments, each of f and g is independently an integer of 400-1,100. In some embodiments, each of f and g is independently an integer of 500-1,000. In some embodiments, each of f and g is independently 600, 700, 800, 900 or 1,000.

In some embodiments, each of $R_2$ and $R_3$ in Formula (III) is independently cyclopropyl, cyclobutyl, cyclohexyl or benzyl.

In some embodiments, $R_2$ and $R_3$ in Formula (III) are methyl, $R_4$ is ethyl, and $R_5$ is methylenecarbonyl.

In some embodiments, P has a structure shown in Formula (IV) below:

Formula (IV)

wherein $R_6$ is a residue of pentaerythritol, methylglucoside, sucrose, diethylene glycol, propanediol, glycerol or polyglycerol whose hydrogen in hydroxyl group is removed; i is 3, 4, 6 or 8; h is an integer of 10-1,500. In some embodiments, h is an integer of 100-1,400. In some embodiments, h is an integer of 200-1,300. In some embodiments, h is an integer of 300-1,200. In some embodiments, h is an integer of 400-1,100. In some embodiments, h is an integer of 500-1,000. In some embodiments, h is an integer of 600, 700, 800, 900 or 1,000.

The linking group X in Formula (I) is a group between the water soluble polymer and the amino acid oligopeptide, which has the function of linking. In some embodiments, the purpose of introducing the linking group is to modify the water soluble polymer so that it could better link to the amino acid oligopeptide. In some embodiments, X is $(CH_2)_n$, $(CH_2)_nCO$, $(CH_2)_nOCO$, $(CH_2)_nNHCO$, —S—, —$SO_2$—, or —$SO_4$—; n is an integer of 1-12. Preferably, n is 1-6. Preferably, n is 1-3. Preferably, n is 1-2. In some embodiments, X is $CH_2CO$.

$A_1$ in Formula (I) could be any amino acid residue or amino acid analogue residue, wherein the amino acid residue or amino acid analogue residue comprises at least one amino group and one carboxylic group. In some embodiments, $A_1$ is an amino acid residue or amino acid analogue residue comprising at least two carboxylic groups and one amino group.

In some embodiments, $A_1$ has a structure shown in Formula (V) below:

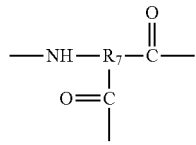

Formula (V)

wherein $R_7$ is $C_{1-20}$ alkyl, $C_{1-20}$ heteroalkyl. In some embodiments, $R_7$ is $C_{1-10}$ alkyl, $C_{1-10}$ heteroalkyl. In some embodiments, $R_7$ is $C_{1-9}$ alkyl, $C_{1-9}$ heteroalkyl. In some embodiments, $R_7$ is $C_{1-8}$ alkyl, $C_{1-8}$ heteroalkyl. In some embodiments, $R_7$ is $C_{1-7}$ alkyl, $C_{1-7}$ heteroalkyl. In some embodiments, $R_7$ is $C_{1-6}$ alkyl, $C_{1-6}$ heteroalkyl. In some embodiments, $R_7$ is $C_{1-5}$ alkyl, $C_{1-5}$ heteroalkyl. In some embodiments, $R_7$ is $C_{1-4}$ alkyl, $C_{1-4}$ heteroalkyl. In some embodiments, $R_7$ is $C_{1-3}$ alkyl, $C_{1-3}$ heteroalkyl. In some embodiments, $R_7$ is methyl, ethyl, propyl, butyl, pentyl, hexyl, heptyl, octyl, nonyl, decyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl, $C_{18}$ alkyl, $C_{19}$ alkyl, $C_{20}$ alkyl. The carbonyl of Formula (V) could link to any one carbon of $R_7$. In some embodiments, $R_7$ is linear alkyl or heteroalkyl. In some embodiments, $R_7$ is branched alkyl or heteroalkyl.

In some embodiments, $A_1$ has a structure shown in Formula (VI) below:

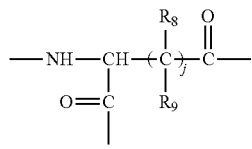

Formula (VI)

wherein, each of $R_8$ and $R_9$ is independently hydrogen, $C_{1-12}$ alkyl, $C_{1-12}$ heteroalkyl, aryl, heteroaryl, aralkyl, or heteroarylalkyl, and $R_8$ and $R_9$ in each repeat unit could be same or different; j is an integer of 1-10. In some embodiments, j is an integer of 1-10. In some embodiments, j is an integer of 1-9. In some embodiments, j is an integer of 1-8. In some embodiments, j is an integer of 1-7. In some embodiments, j is an integer of 1-6. In some embodiments, j is an integer of 1-5. In some embodiments, j is an integer of 1-4. In some embodiments, j is an integer of 1-3. In some embodiments, j is an integer of 1-2.

In some embodiments, $A_1$ is aspartic acid residue or glutamic acid residue.

Each of $A_2$ and $A_3$ in Formula (I) could be independently any amino acid residue or amino acid analogue residue, wherein the amino acid residue or the amino acid analogue residue comprises at least one amino group and one carboxylic group. In some embodiments, each of $A_2$ and $A_3$ independently has a structure shown in Formula (VII) below:

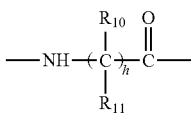

Formula (VII)

wherein, each of $R_{10}$ and $R_{11}$ is independently hydrogen, $C_{1-6}$ alkyl, or $C_{1-6}$ heteroalkyl, and $R_{10}$ and $R_{11}$ in each repeat group could be same or different; h is an integer of 1-10. In some embodiments, each of $R_{10}$ and $R_{11}$ is independently methyl, ethyl, propyl, butyl, pentyl, hexyl. In some embodiments, each of $R_{10}$ and $R_{11}$ is independently linear alkyl or heteroalkyl. In some embodiments, each of $R_{10}$ and $R_{11}$ is independently branched alkyl or heteroalkyl. In some embodiments, h is 1, 2, 3, 4, 5, 6, 7, 8, 9, or 10.

In some embodiments, each of $A_2$ and $A_3$ is independently residue of glycine, alanine, leucine, isoleucine, valine, proline, phenylalanine, methionine, serine, threonine, cysteine and tyrosine.

The drug in the conjugate of water soluble polymer-amino acid oligopeptide-drug of the present invention includes any drug molecule that can bind to an amino acid or amino acid analogue. In some embodiments, the drug molecule that can bind to an amino acid or amino acid analogue comprises one functional group, such as amino, hydroxyl, phenolic, thiol or guanidyl group. Example of drug molecule comprising amino, hydroxyl, phenolic, thiol or guanidyl includes but not limited to: acetohydroxamic acid, acyclovir {2-amino-1,9-dihydro-9-[(2-hydroxyethoxy) methyl]6H-purin-6-one}, allopurinol, adenosine (6-amino-9-i3-D-ribofuranosyl-9-H-purine), prednisolone, prednisone, triamcinolone, cortisol (hydrocortisone), adenosine (6-amino-9-β-D-ribofuranosyl-9-H-purine), cortisone, estradiol, gynotermone, estriol, 16-hydroxyestrone, equilin, equilenin, dienoestrol, hexestrol, stilbesterol, benzestrol, 4-hydroxyandrostenedione, ICI 164384, aminoglutethimide, ICI 182780, 7-aminophenylthioandrost-4-ene-3,17-dione, megestrol, chlormadinone, methylnorethindron, lynestrenol, methandienone, mifepristone, onapristone, danazol, methenolone, stanozolol, amikacin(D-streptamine), 9-aminoacridine, aminoacridine, atovaquone, baclofen, calcifediol, calcitriol, phenylpropanolamine, captopril {1-[(2S)-3-thiol-2-methylpropionyl]-L-proline}, secbutabarbital, carbamazepine, carbidopa, theophylline, levodopa, pseudoephedrine, chloromycetin, chloroxine, clioquinol, chloroxylenol, chlorphenesin carbamate, chlorthalidone, phenylpropanolamine, clonidine[2-(2,6-dichloroanilino)-2-imidazoline], cladribine, phenylpropanolamine hydrochloride, clonazepam, cytarabine[4-amino-1-β-D-arabinofuranosyl-2-(1H)-pyrimidone], danazol, dexpanthenol, guaifenesin, daunorubicin, adriamycin, idarubicin, dextrothyroxine [D-3,5,3',5'-tetraiodothyronine], didanosine, dezocine, dopaminem, dihydrotachysterol, dicoumarolum, dronabinol, diprophylline, enoxacin, enalapril [(S)-1-[N-(1-carboxyl-3-phenylpropyl)-L-alanyl-L-proline], dienoestrol, calcipotriene [(5Z,7E,22E,24S)-24-cyclopropyl-9,10-secocholestane-5,7,10 (19), 22-tetraen-1α,3β,24-triol], viosterol [9,10-secoergsta-5, 7,10 (19), 22-tetraen-3-ol, (3β,5Z,7E, 22E)], levonorgestrel, methylnorethindrons, norethindrone, natulane, famciclovir, felodipine, norgestimate, floxuridine, idoxuridine, etoposide, monobenzone, fludarabine phosphate, dihydrotachysterol, finasteride, fluconazole, fludarabine, fluorouracil, flucytosine, ethchlorvynol, fluorometholone, halobetasol, mometasone, fluvoxamine, flurandrenolide, ganciclovir, fluticasone, desogestrel, ethinyl estradiol, ethinyloestradiol, mestranol, desoximetasone, dexamethasone, gentamicin, hydroxyprogesterone, provera, indamine, levodopa, methyldopa, hydralazine, dihydrochlorothiazide, hydroflumethiazido, iodoquinol, kanamycin, lovastatin, masoprocol, lorazepam, oxazepam, medrysone, methylphenobarbital, methaqualone, metaxalone, methocarbamol, methyclothiazide, metronidazole, mercaptopurine, methimazole, methotrexate, milrinone, nandrolone, naphazoline, mexiletine, nitrofurantoin, niclosamide, nifedipine, nimodipine, norepinephrine, novobiocin, omeprazole, oxandrolone, pemoline, pentamidine, oxymetholone, omeprazole, oxandrolone, nordihydroguaiaretic acid, zafirlukast, BANZEL (rufinamide), phenacemide, phenelzine, phenazopyridine, phenobarbital, sulfisoxazole, phentolamine, phenytoin, podofilox, methyhydrazine, polythiazide, trichlormethiazide, primidone, probucol, propofol, propylthiouracil, procarbazine, procarbazine, sulfadoxine, quinethazone, propylthiouracil, virazol, streptozotocin rimexolone, simvastatin, carinamide, stanozolol, sulfamethoxazole, sulfamethoxazole, sulfisoxazole, sulfonamide, sulfadiazine, sulfasalazine, temazepam, terazosin, tacrine, thiabendazole, thiopental, tolazoline, thioguanine, olmesartan medoxomil [(5-methyl-2-on-1,3-dioxo-4-yl) methyl-5-(1-hydroxy-1-methyl-ethyl)-2-propyl-3[W-[2-QH-tetrazole-5-yl]-phenyl]-phenyl]methyl]-3H-imidazole-4-formate], teniposide, torsemide, triamterene, trifluridine, trimethoprim, trimetrexate, uramustine, tropicamide, vidarabine, warfarin, zalcitabine, zidovudine, fluticasone furoate, Ro 46-2005, bosentan, clazosentan, tezosentan, Isentress {N-[(4-fluorophenyl)methyl]-1, 6-dihydro-5-hydroxy-1-methyl-2-[1-methyl-1 [[(5-methyl-1,3,4-oxadiazole-2-yl) carbonyl]amino]ethyl]-6-on-4-pyrimidinylformamide}, aliskiren (2S,4S,5S,7R)-5-amino-N-(2-carbamoyl-2-methyl-propyl)-4-hydroxy-7-114-methoxy-3-(methoxy-propoxy)-phenyl]methyl}-8-methyl-2-propyl-2-yl-pelargonamide, efavirenz, dextroamphetamine, finasteride, armodafinil, anidulafungin, darunavir, tipranavir, amprenavir, brecanavir, telbivudine, lenalidomide, thalidomide, entecavir, conivaptan, NEXAVAR (sorafenib), BARACLUDE (entecavir), VIDAZA (azacytosine), ALIMTA (pemetrexed), ramelteon, ezetimibe, CLOFARA (clofarabine), nelarabine, TARCEVA (erlotinib), CIALIS (tadalafil), amprenavir, REYATAZ (atazanavir), ezetimibe, acetaminophen, gliburnuride, etravirine, abacavir (Ziagen), N-[1-[(2R,3R,4S,5R)-3,4-dihydroxy-5-methyltetrahydrofuran-2-yl]-5-fluoro-2-onepyrimidine-4-yl]amine, tenofovir, voriconazole, dihydrochlorothiazide, zoledronic acid, melatonin, 3-Aminopropanesulfonic acid, fulvestrant, voriconazole, resveratrol, lovastatin, tenofovir disoproxil, tenofovir, simvastatin, pentyl N[1-K2R, 3R, 4S, 5R)-3,4-dihydroxy-5-methyltetrahydrofuran-2-yl]-5-fluoro-2-onepyrimidine-4-yl]carbamate ((capecitabine), calciferol (vitamin D2), cholecalciferol (vitamin D3), 1,25-dihydroxycholecalciferol, lamivudine, doxercalciferol (1α-hydroxy vitamin D2), dihydrotachysterol (vitamin D4), lopinavir, 3-[4-(4-chlorphenyl)cyclohexyl]-4-hydroxynaphthaline-1,2-dione, cidofovir, ritonavir, entacapone, CIALIS (tadalafil), finasteride, zileuton, melatonin, TAMIFLU (oseltamivir), paricalcitol, metronidazole, diflunisal, aspirin, meloxicam, JANUVIA (sitagliptin), emtricitabine 5-fluoro-1-(2R,5S)-[2-hydroxymethyl-1, 3-oxathiolan-5-yl]cytosine, propofolum, vitamin A analogue, everolimus (1R,9S, 12S, 15R, 16E, 18R, 19R, 21R, 23S, 24E, 26E, 28E, 30S, 32S, 35R)-1, 18-dihydroxy-12-{(IR)-2-[(IS, 3R, 4R)-4-(2-cyanethyloxyl)-3-methoxycyclohexyl]-1-methyl ethyl}-19, 30-dimethoxy-15, 17, 21, 23, tetra, 35-hexamethyl-11, 36-dioxo-4-aza-tricyclic[30.3.1.04, 9]hextriacon-16, 24, 26, 28-tetraene 2,3,10,14, 20-pentylone], curcumin, tipranavir, etravirine, tadalafil, tolvaptan, polypeptides, DNAs, RNAs, adenine, guanine, cytosine, cytosine and uracil.

In some embodiments, the drug molecule that can bind to the amino acid or amino acid analogue comprises one carboxyl or one phosphate/phosphonate group. Example of the drug molecule comprising the carboxyl group includes but not limited to: methallenestril, aminosalicylic acid, methallenestril, aminosalicylic acid, baclofen, carbidopa, levodopa, aminobenzoic acid, bumetanide, captopril [1-[(2S)-3-thiol-2-methylpropionyl]-L-proline], cilastatin [(2)-7-[[(3)-2-amino-2-carboxyethyl]sulfo]-2-[(S)-2, 2-dimethylcyclopropanecarboxamide]-2-heptylic acid], levothyroxine [D-3,5,3',5'-tetraiodothyronine], amphotericin B, etretinate, eflornithine, 10-undecenoic acid, cinoxacin, clorazepate, profloxacin [1-cyclopropyl-6-fluoro-1,4-dihydro-4-on-7-(1-piperazino)-3-quinolinic acid], cromolyn sodium, dehydrocholic acid, enalapril [(S)-1-[N-(1-carboxyl-3-phenylpropyl)-L-alanyl]-L-proline], enoxacin, ethacrynic acid, furosemide, gemfibrozil, octadecenoic acid, 2-[4-(4-chlorobenzoyl)-phenoxy]-2-methyl-propanoic acid (fenofibric acid), 7-[(1S,3R, 7S, 8S, 8aR)-1-(2S)-2-methylbutanoyloxy-3, 7-dimethyl-1, 2, 3, 7, 8, 8a-hexahydro naphthalen-1-yl][(3R,5R)-3, 4-dihydroxyheptylic acid], gabapentin, fosinopril, pravastatin, argatroban, 7 theophyllineacetic acid, iopanoic acid, liothyronine, iotalamic acid, Duloamide [N,N'-(2-chloro-5-cyano-m-phenylene)dioxalic acid], probenecid, lisinopril [(S)-1-[N-(1-carboxyl-3-phenylpropyl)-L-lysyl]-L-proline], methotrexate, acetylaminopropane sulfonate, nedocromil, thiosalicylic acid, quinapril, ramipril, norfloxacin, ioxaglate, sulfasalazine, pravastatin, valproic acid, olmesartan, LETAIRIS (ambrisentan), darusentan, azelaic acid (anchoic acid), ursodeoxycholic acid, ofloxacin, TAK-044{:cyclo[D-aspartyl-3-[(4 -phenylpiperazine-1-yl) carbonyl]-L-propylamino-L-aspartyl-D-2-(2-thienyl)glycyl-L-leucyl -D-tryptophanyl]}, BQ123{cyclo[D-tryptophan-D-aspartic acid-proline-D-valine-leucine]}{cyclo[D-Trp-D-Asp-Pro-D-Val-Leu]}, LIPITOR (atorvastatin), fluticasone furoate, lubiprostone, LYRICA (pregabalin-13), ALIMTA (pemetrexed), treprostinil, CRESTOR (rosuvastatin), methyldopa, valsartan, telmisartan, (E)-5-[[-4-(2-carboxyethyl) carbamoyl]phenyl] aza]-2-hydroxybenzoic acid, eprosartan, eprosartan, LESCOL (fluvastatin), (E)-5-[-4-(2-carboxyl) carbamoyl] phenyl]aza]-2-hydroxybenzoic acid, asparagine-alanine-proline-valine-tryptophan-isoleucine-proline-glutamine (Asn-Ala-Pro-Val-Ser-IIe-Pro-Gln), 2-naphthylacetic acid, suprofen, 3-(2-thienylcarbonyl)-phenylacetic acid, ibuprofen, flurbiprofen, aspirin, carprofen, pranoprofen, alminoprofen, benoxaprofen, indoprofen, hexaprofen, 10, 11-dihydro-10-on-dibenzo [b, f]thiepin-2-carboxylic acid, W-(2-oncyclo-pentyl)-methyl]benzoic acid, [5-phenyl-(2-thiophene)]-carboxylic acid, (3-phenoxylphenyl)acetic acid, 4-(4-chlorphenyl)-2-phenyl-5-thiazolacetic acid, 4-(2, 5-dihydropyrrole-1-yl)-phenylacetic acid, 4,5-biphenyl-2-oxazole propanoic acid, [4-2-cyclopentanone-methyl]phenylacetic acid, 10, 11-dihydro-10-on-dibenzo [b, f]thiepin-2-carboxylic acid, 5-cyclohexyl-2, 3-dihydro-IH indenyl-1-carboxylic acid, 5-phenyl-2-furanpropanoic acid, Y-on-(1, 1'-biphenyl)-4-butyric acid, 5-benzoyl-2, 3-dihydro-IH-pyrrolecarboxylic acid, benzylidene-IH-indene-3-acetic acid, 1-benzoyl-5-methoxy-2-methyl-IH-benzazole-3-acetic acid, 4-benzoyl-IH-pyrrole-2-acetic acid, 1,3,4,9-tetrahydropyrane-[3,4-b]benzazole-1-acetic acid, 3-phenylamino-phenylacetic acid, 2-phenylamino-phenylacetic acid, 3-(4-chlorphenyl)-1-phenyl-IH-pyrazol-4-acetic acid, 4-(2-acryloxyl)phenylacetic acid, 2-phenyl-5-thiazole-acetic acid, 4-(6-methoxy-2-naphthyl-3-propanoic acid, acetylsalicylic acid, 3-phenylbenzoic acid, salicylsalicylate, [(1-benzyl-IH-indazole-3-yl)oxo]acetic acid, trisalicylate, sulfasalazine, 2-anilinopyridine-3-carboxylic acid, eltrombopag(eltrombopag), montelukast, bendamustine (bendamustine), prostaglandin E2, prostaglandin F2a, carboprost (15-methylprostaglandin F2a), prostaglandin D2, prostaglandin E1 (alprostadil), prostaglandin F1 a, (Z)-7-[(1R,2R, 3R, 5S)-3, 5-dihydroxy-2-[(E, 3S)-3-hydroxy-5-phenyl+pentenyl]cyclopentyl]-5-heptenoic acid, (E)-7-[(1R, 2R, 3R, 5S)-3, 5-dihydroxy-2-[(3R)-3-hydroxy-5-phenypentyl]cyclopentyl]-5-heptenoic acid, prostaglandin (; 12(prostacyclin), (Z)-7-[(1R,2R, 3R, 5S)-3, 5-dihydroxy-2-[(E, 3R)-3-hydroxy-4-[3-(trifluoromethyl)phenoxyl]butenyl]cyclopentyl]-5-heptenoic acid, (E)-7-[(1R,2R, 3R, 5S)-3, 5-dihydroxy-2-(-3-decanone) cyclopentyl]5-heptenoic acid, misoprostol, gemeprost, 7-[3-hydroxy-2-3 (3-hydroxy-4-phenoxyl-1-butenyl-5-cyclopentanone]-5-heptenoic acid, fenprostalene, prostaglandin A1, prostaglandin A2, prostaglandin Bi, prostaglandin A2, retinoic acid, bexarotene, 9-cis retinoic acid (alitretinoin), retinoic acid analogue 13-cis retinoic acid (isotretinoin), bexarotene analogue, bexarotene analogue, penicillin G, phenoxylmethyl penicillin, methicillin, oxacillin, piperacillin, mezlocillin, carbenicillin, a-ticarcillin, ampicillin, amdinocillin, cephalosporin, cephapirin, cefazolin, cephadroxil, cefradine, cefonicid, cefamandole, cefuroxime, cefoxitin, ceforanide, cefotetan, cefuroxime, loracarbef, cefotaxime, ceftriaxone, cefoperazone, moxalactam, LIVALO (pitavastatin), TYVASO (travoprost), FOLOTYN (pralatrexate), TAMIFLU (oseltamivir), beraprost.

In some embodiments, each of $D_1$ and $D_2$ is independently a residue of anti-tumor drug. In some embodiments, the residue of anti-tumor drug can react with $A_2$ or $A_3$, forming peptide or ester bond. In some embodiments, after modification, the anti-tumor medicament can react with $A_2$ or $A_3$, forming peptide or ester bond. In some embodiments, the anti-tumor drug is dasatinib, rapamycin, elomotecan, imatinib, erlotinib, gefitinib, lapatinib, sorafenib, sunitinib, paclitaxel, camptothecin, cinobufagin, glycyrrhetinic acid, or scopoletin. In some embodiments, the anti-tumor drug is dasatinib.

In some embodiments, the present application provides a conjugate with a structure shown in Formula (VIII) below:

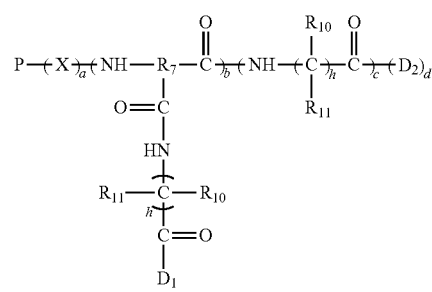

Formula (VIII)

wherein, each of $R_{10}$ and $R_{11}$ is independently hydrogen, or $C_{1-6}$ alkyl, and $R_{10}$ and $R_{11}$ in each repeat unit could be same or different; h is an integer of 1-10. $R_7$, P, X, a, b, c, d, $D_1$, and $D_2$ are same as described above.

In some embodiments, the present application provides a conjugate with a structure shown in Formulas (IX), (X), or (XI) below:

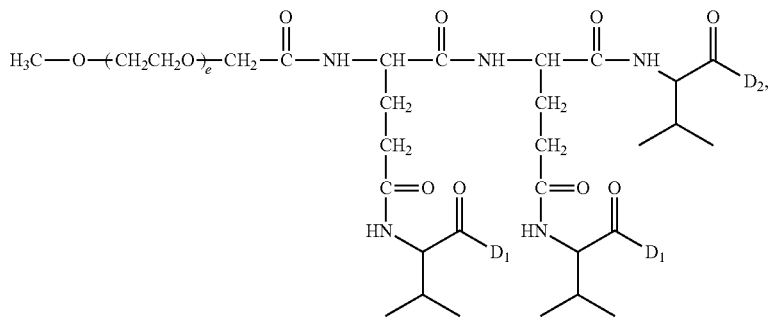

Formula (IX)

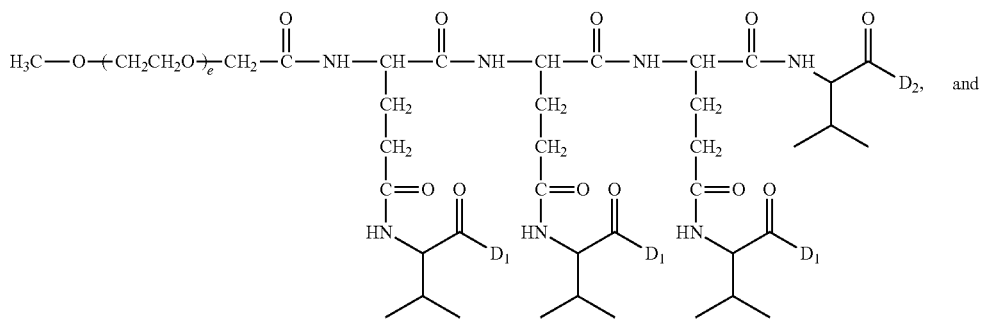

Formula (X)

and

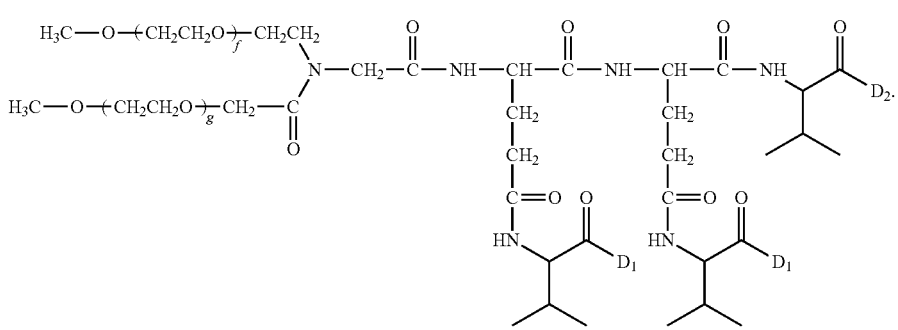

Formula (XI)

wherein, each of e, f, and g is independently an integer of 10-1,500. In some embodiments, each of e, f, and g is independently an integer of 100-1,400. In some embodiments, each of e, f, and g is independently an integer of 200-1,300. In some embodiments, each of e, f, and g is independently an integer of 300-1,200. In some embodiments, each of e, f, and g is independently an integer of 400-1,100. In some embodiments, each of e, f, and g is independently an integer of 500-1,000. In some embodiments, each of e, f, and g is independently 600, 700, 800, 900 or 1,000. $D_1$ and $D_2$ are same as described above. $D_1$ and $D_2$ are the same drug. In one embodiment, $D_1$ and $D_2$ are dasatinib.

The compounds and derivatives thereof of the present application are denominated according to IUPAC (International Union of Pure and Applied Chemistry) or CAS (Chemical Abstracts Service, located in Columbus, Ohio) nomenclature system.

The minimum and maximum values of carbon atom in a hydrocarbon group are expressed by prefixes; for example, prefix $(C_{a-b})$ alkyl means any alkyl containing the number of carbon atom from "a" to "b". Accordingly, for example, $(C_{1-6})$ alkyl is an alkyl comprising one to six carbon atoms. The alkyl is linear or branched.

"Alkoxy" refers to a linear or branched, monovalent, saturated aliphatic chain that is bound with an oxygen atom, which includes but is not limited to, such as methoxy, ethyoxyl, propoxy, butoxy, isobutoxy, tert-butoxy and other similar groups.

"Alkyl" refers to a linear or branched, monovalent, saturated aliphatic chain, which includes but is not limited to such as methyl, ethyl, propyl, isopropyl, butyl, isobutyl, pentyl, isopentyl, hexyl and other similar groups.

"Heteroalkyl" refers to above-mentioned alkyl group in which one or more carbon atoms have been replaced by heteroatom(s), such as nitrogen, oxygen or sulfur. If the heteroalkyl contains more than one heteroatom, the heteroatoms could be same or different.

"Alkenyl" refers to a linear or branched hydrocarbon having one or more double bonds, which includes but is not limited to such as ethenyl, propenyl and other similar groups.

"Aryl" refers to a cyclic aromatic hydrocarbon, which includes but is not limited to such as phenyl, naphthyl, anthryl, phenanthryl and other similar groups.

"Cycloalkyl" refers to a saturated alkyl group having one or more rings, which could fuse with one aromatic group. Cycloalkyl includes but not limited to such as cyclopropyl, cyclobutyl, cyclopentyl, cyclohexyl, cycloheptyl, indanyl, tetrahydronaphthyl and other similar groups.

"Arylalkyl" refers to a group formed by covalently binding above-mentioned aryl and alkyl, such as but not limited to phenylmethyl, phenylethyl, or phenylpropyl.

"Heteroaryl" refers to a monocyclic or polycyclic aromatic hydrocarbon, in which one or more carbon atoms have been replaced by heteroatom(s), such as nitrogen, oxygen or sulfur. If the heteroaryl contains more than one heteroatom, the heteroatoms could be same or different. The heteroaryl includes but is not limited to such as benzofuranyl, benzothienyl, benzimidazolyl, benzoxazolyl, benzothiazolyl, benzopyran, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phthalazinyl, pteridinyl, purinyl, pyranyl, pyrazinyl, pyrazolyl, pyridazinyl, pyrido[3,4-b]indolyl, pyridyl, pyrimidyl, pyrrolyl, quinolizinyl, quinolyl, quinoxalinyl, thiadiazolyl, thiatriazol, thiazolyl, thienyl, triazinyl, triazolyl, xanthenyl and other similar groups.

A cyclic group could bind to another group in a variety of manners. Unless otherwise clearly indicated, the binding includes all possible binding manners. For example, "pyridyl" includes 2-, 3-, or 4-pyridyl, and "thienyl" includes 2- or 3-thienyl.

"Amino acid analogue" is an organic compound containing at least one amino and at least one carboxyl group, which has a structure similar to an amino acid.

A Method for Preparing the Conjugate of Water Soluble Polymer-amino Acid Oligopeptide-drug The conjugate of the present invention could be synthesized through the following procedures. The procedure is merely for exemplary illustration and does not intend to exclude other potential methods for preparing the conjugate. In addition, the steps in the procedure are present only for better demonstrating the method for preparing the conjugate, and according to the actual needs, the steps could be modified without departing from the scope of the invention in the present application.

A method for preparing the conjugate of water soluble polymer-amino acid oligopeptide-drug, comprising:

forming the conjugate $P\text{-}(X)_a\text{-}(A_1)_b$ by linking the water soluble polymer P to amino acid $A_1$ through the linking group X.

making the drug molecule $D_1$ react with amino acid $A_2$ to form the conjugate $D_1\text{-}A_2$.

making the drug molecule $D_2$ react with amino acid $A_3$ to form the conjugate $D_2\text{-}A_3$.

linking the conjugate(s) $D_1\text{-}A_2$ and/or $D_2\text{-}A_3$ to the compound $P\text{-}(X)_a\text{-}(A_1)_b$ to form the compound of Formula (I).

In some embodiments, the water soluble polymer could be modified to introduce an active group for binding to an amino acid oligopeptide. In some embodiments, the introduction of the active group is realized by linking to the group X. In some embodiments, the active group introduced is a carboxylic group.

In some embodiments, the conjugate(s) $D_1$-$A_2$ and/or $D_2$-$A_3$ could be formed through the reaction between the active group of drug molecule and the amino acid $A_2$ or $A_3$. In some embodiments, the active group of the drug molecule could be hydroxyl or amino. In some embodiments, the reaction between the drug molecule and the amino acid is esterification or amidation reaction.

In some embodiments, the compound of Formula (I) is formed through the amidation reaction between the conjugate(s) $D_1$-$A_2$ and/or $D_2$-$A_3$ and the compound P—(X—)$_a$—($A_1$)$_b$.

The Pharmaceutical Composition of the Conjugate of Water Soluble Polymer-amino Acid Oligopeptide-drug In another aspect, the present invention further provides the pharmaceutical composition comprising the conjugate of water soluble polymer-amino acid oligopeptide-drug and a pharmaceutically acceptable carrier.

The term of "a pharmaceutically acceptable carrier" herein refers to a pharmaceutically acceptable substance, ingredient or medium, such as liquid or solid filler, diluent, excipient, solvent or encapsulating material, which involves in the loading or transportation of the compound of the present invention from one position, body fluid, tissue, (internal or external) organ, or a body part, to another position, body fluid, (internal or external) organ, or a body part. The pharmaceutically acceptable carrier could be medium, diluent, excipient, or other materials which do not have excessive toxicities or side effects, and could be used to contact the animal tissues. The conventional pharmaceutically acceptable carrier includes sugar, starch, cellulose type, maltose, tragacanth, gelatin, Ringer's solution, alginic acid, normal saline, buffers, etc.

Each of the pharmaceutically acceptable carriers should be compatible with other ingredients. For example, it can form a formulation with the conjugate of the present invention and it does not have excessive toxicity, irritation, allergic response, immunogenicity, or other problems or complications to biological living tissues or organs and possesses a reasonable benefit-risk ratio.

Some of the pharmaceutically acceptable carriers contain: (1) saccharide, such as lactose, glucose and sucrose; (2) starch, such as corn starch and potato starch; (3) cellulose and its derivative, such as sodium carboxymethyl cellulose, ethyl cellulose, cellulose acetate; (4) gum tragacanth powder; (5) maltose; (6) gelatin; (7) talcum powder; (8) excipient, such as cocoa butter and suppository wax; (9) oil, such as peanut oil, cottonseed oil, safflower oil, sesame oil, olive oil, corn oil and soybean oil; (10) glycol species, such as propanediol; (11) polyol species, such as glycerol, sorbitol, mannitol and PEG; (12) lipid, such as ethyl oleate, ethyl laureate; (13) gum agar gel; (14) buffer agent, such as magnesium hydroxide and aluminum hydroxide; (15) alginic acid; (16) sterile pyrogen-free water; (17) normal saline; (18) Ringer's solution; (19) alcohol species, such as ethanol and propanol; (20) phosphate buffer; (21) other compatible substances without toxicity in a pharmaceutical dosage form, such as acetone.

The pharmaceutical composition could contain pharmaceutically acceptable excipients to mimic physiological conditions, such as pH adjusting and buffering agent, toxicity adjusting agent etc., such as sodium acetate, sodium chloride, potassium chloride, calcium chloride, sodium lactate, etc.

The pharmaceutical ingredients could be prepared to form any suitable dosage form, such as solid dosage form (such as tablet, capsule, powder, granule etc.) and liquid dosage form (such as aqueous solution, emulsion, elixir, syrup etc.). The process for preparing the pharmaceutical composition is well-known in the art, which could be any conventional process provided in such as *Remington, The Science and Practice of Pharmacy* (Gennaro ed. 20th edition, Williams & Wilkins PA, USA) (2000).

In some embodiments, the compound or pharmaceutical composition of the present invention could be made into a dosage form which is suitable for drug release. It could be administered through injection (such as subcutaneous, intravenous, intramuscular, artery, sheath, capsule, box, intracardial, intradermal, intraperitoneal, trachea, skin, intraarticular, subcapsular, subarachnoid, intraspinal, intrasternal, and/or infusion) and non-injection route (such as oral, intestinal, buccal, nasal, intranasal, mucosal, skin, emplastrum, dermal, ophthalmic, pulmonary, sublingual, rectal, vaginal or topical administration of epidermis).

The suitable dosage form includes (but not limited to) a dosage form for injection, such as emulsion, solutions and suspensions; a dosage form for oral, such as tablets, capsules, pills, sugar-coated pills, powder and granules; a dosage form for topical administration or dermal absorption, such as spray agents, ointments, pastes, creams, lotions, gels, solutions, drug patches and inhalants; a dosage form for vaginal or rectal administration, such as suppositories. These dosage forms could be prepared in suitable conditions according to the compound and suitable excipients, and the preparation method and process are well-known in the art, provided in such as *Remington: The Science and Practice of Pharmacy* (Gennaro ed. 20th edition, Williams & Wilkins PA, USA) (2000).

Use of the Conjugate of Water Soluble Polymer-Amino Acid Oligopeptide-drug and/or Pharmaceutical Composition One aspect of the present invention is to modify the water soluble polymer in order to increase the solubility of the drug molecule and extend half-life thereof. In some embodiments, the pharmaceutical activity, the drug loading capacity, the stability and the solubility of the conjugate are all increased when compared to the unmodified drug molecule.

Another aspect of the present invention is to use the amino acid oligopeptide to increase the stability of the pharmaceutical conjugate, thereby reducing toxic and side effects. In some embodiments, the increased stability of the pharmaceutical conjugate is realized by selecting a suitable amino acid oligopeptide. In some embodiments, the increased stability of the pharmaceutical conjugate is realized by selecting a suitable amino acid residue (i.e. the amino acid $A_2$ or $A_3$ in Formula (I)) which binds to the drug molecule. Preferably, the amino acid residue that binds to the drug molecule is valine residue. In some embodiments, the toxicity of the conjugate is decreased. In some embodiments, the conjugate further improves the clinical effect of the drug.

In another aspect of the present invention, each hydrophilic polymer could link to multiple drug molecules through the amino acid oligopeptides, thus remarkably increasing loading ratio of the drug. In some embodiments, each hydrophilic polymer could link to at least two drug molecules. In some embodiments, each water soluble polymer could link to at least three drug molecules. In some embodiments, each water soluble polymer could link to at least four drug molecules.

Another aspect of the present invention provides use of the conjugate and/or pharmaceutical composition above in the manufacture of a medicament and in the treatment of a disease.

In some embodiments, the present invention provides use of the conjugate and/or pharmaceutical composition above in the manufacture of a medicament for treating tumor, fungal infection, rheumatoid arthritis, multiple sclerosis, heart valve restenosis or pneumonia.

In some embodiments, the anti-tumor medicament is for treating diseases selected from group consisting of: leukemia, acute myelocytic leukemia, chronic myelocytic leukemia, chronic lymphocytic leukemia, acute lymphocytic leukemia, myelodysplasia, multiple myeloma, Hodgkin's disease or non-Hodgkin's disease, small cell lung cancer or non-small cell lung cancer, stomach cancer, colon cancer, esophageal cancer, colorectal cancer, prostate cancer, ovarian cancer, breast cancer, brain cancer, urinary tract cancer, kidney cancer, bladder cancer, malignant melanoma, liver cancer, uterine cancer, pancreas cancer, myeloma cancer, endometrial cancer, head and neck cancer, pediatric tumors, sarcomas.

In some embodiments, the present application provides a method for treating tumor, fungal infection, rheumatoid arthritis, multiple sclerosis, heart valve restenosis or pneumonia in a subject, the method comprising administrating the subject a therapeutically effective amount of the conjugate or the pharmaceutical composition above. In some embodiments, the subject is a mammal. In some embodiments, the subject is human, domestic animals or pets.

The conjugate or the pharmaceutical composition of the present invention could be administrated to the body through any suitable route, such as oral, intravenous injection, intranasal, topical, intramuscular injection, intradermal injection, percutaneous administration or subcutaneous route. In some embodiments, the administration of the conjugate or pharmaceutical composition of the present invention includes oral, mucosal, sublingual, ocular, topical, parenteral, rectal, intracisternal, vagina, peritoneum, bladder, nasal administration.

In some embodiments, the conjugate or pharmaceutical composition of the present invention could be administrated simultaneously with a second active substance, in order to obtain additive effects or even synergistic effects in the body. For example, the compound of the present invention and the second active substance could be combined into one pharmaceutical composition, or they could be administrated simultaneously or sequentially in separate compositions. The second active substance that can be administrated simultaneously with the compound of the present invention for treating the cancer includes but not limited to fluorouracil, doxorubicin, daunorubicin, tamoxifen, leuprolide, goserelin, flutamide, nilutamide, finasteride, dexamethasone, aminoglutethimide, amsacrine, anastrozole, asparaginase, BCG, bicalutamide, bleomycin, clinical, busulfan, camptothecin, capecitabine, carboplatin, carmustine, chlorambucil, cisplatin, cladribine, colchicine, cyclophosphamide, drugs, cyproterone, cytarabine, dacarbazine, dactinomycin d, daunorubicin, dienoestrol, diethylstilbestrol, docetaxel, doxorubicin, adriamycin, epirubicin, estradiol, estramustine, etoposide, exemestane, filgrastim, fludarabine, fludrocortisone, fluorouracil, fluoxymesterone, flutamide, gemcitabine, genistein, goserelin, tamoxifen, teniposide, testosterone, titanocene dichloride, topotecan, trastuzumab, tretinoin, vinblastine, hydroxyurea, idarubicin, ifosfamide, imatinib, interferon, irinotecan, irinotecan, letrozole, leucovorin, pentostatin, mithramycin, procarbazine, raltitrexed porfimer, rituximab streptozocin, suramin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, platinum, paclitaxel, pamidronic acid, thioguanine, thiotepa, chloromethane, topotecan titanocene, trastuzumab, tretinoin, vinblastine, vincristine, vindesine, vinorelbine.

In some embodiments, the conjugate of the present invention could be used to treat cancer simultaneously with non-chemical methods. In some embodiments, the conjugate of the present invention could be used simultaneously with radiation therapy. In some embodiments, the conjugate provided in the present invention could be used with surgery, thermoablation, focused ultrasound therapy, cryotherapy or any combination thereof.

In some embodiments, the conjugate of the present invention could be used with steroid simultaneously. The suitable steroid includes but not limited to: amcinonide, beclomethasone, betamethasone, budesonide, chloroprednisone, clobetasol, corticosterone, cortisone, desonide, desoximetasone, dexamethasone, diflorasone, diflucortolone, difluprednate, glycyrrhetinic acid, fluazacort, flumetasone, flunisolide, flucloronide, fluocinonide, fluocinonide, fluocortin butyl, fluocortolone, flurandrenolone, fluperolone acetate, fluprednidene acetate, fluprednisolone, flurandrenolide, fluorine propinate, formocortal, clobetasol propionate, halcinonide, halometasone, hydrocortisone, loteprednol etabonate, mazipredone, medrysone, meprednisone, 6-methyl prednisolone, mometasone furoate, paramethasone, prednisolone, dexamethasone, and 25-prednisolone diethylaminoacetate.

In some embodiments, the compound of the present invention could be used with immunotherapeutic agents simultaneously. The suitable immunotherapeutic agent includes multidrug resistance reversal agents for tumor cells (such as verapamil), rapamycin, mycophenolate mofetil, thalidomide, cyclophosphamide, cyclosporine, and monoclonal antibodies.

The beneficial effects of the conjugate of the present application are: 1) the conjugate of water soluble polymer-amino acid oligopeptide-drug of the present application possesses better therapeutical effects than the drug. The conjugate of the present application exhibits better anti-tumor or anti-cancer activities than the drug at the same dosage; 2) the water soluble polymer-amino acid of the present application could bind to more drugs, increase the drug load capacity of the conjugate, and slow release the drugs, which avoid multiple administrations to a patient for maintaining effective plasma concentration; 3) the conjugate reduces the toxicity of the drug; 4) the stability of the pharmaceutical conjugate is improved by using the amino acid $A_1$ and $A_2$, which facilitates the preparation, storage and administration of the drug.

EXAMPLE

Conjugates of Dasatinib

The dasatinib used in the present example was purchased from Nanjing Ange Pharmaceutical Co., Ltd. L-(+)-glutamic acid was purchased from Beijing Chemical Reangent Co. p-toluenesulfonic acid, benzyl alcohol and dicyclohexylcarbodiimide (DCC) were purchased from Sinopharm Chemical Reagent Co. Ltd. 4-dimethylaminopyridine (DMAP) and 1-hydroxybenzotriazole (HOBt) were from Shanghai Medpep Co., Ltd. N-(tert-Butoxycarbonyl)glycine, N-(tert-butoxycarbonyl)alanine, N-(tert-butoxycarbonyl)valine and N-tert-butoxycarbonyl-L-glutamic acid-5-benzylester were purchased from Sichuan Tongsheng Amino acid Co., Ltd. Methoxy PEG acetic acid (20K) and Y-shape PEG acetic acid (40K) were provided by Beijing JenKem Technology Co., Ltd., and other reagents were commercial available.

EXAMPLE 1

Preparation of the Conjugate of Methoxy PEG Dipeptide Acid of Glutamic Acid (Number-average Molecular Weight of 20,000)-dasatinib (DSR-1)

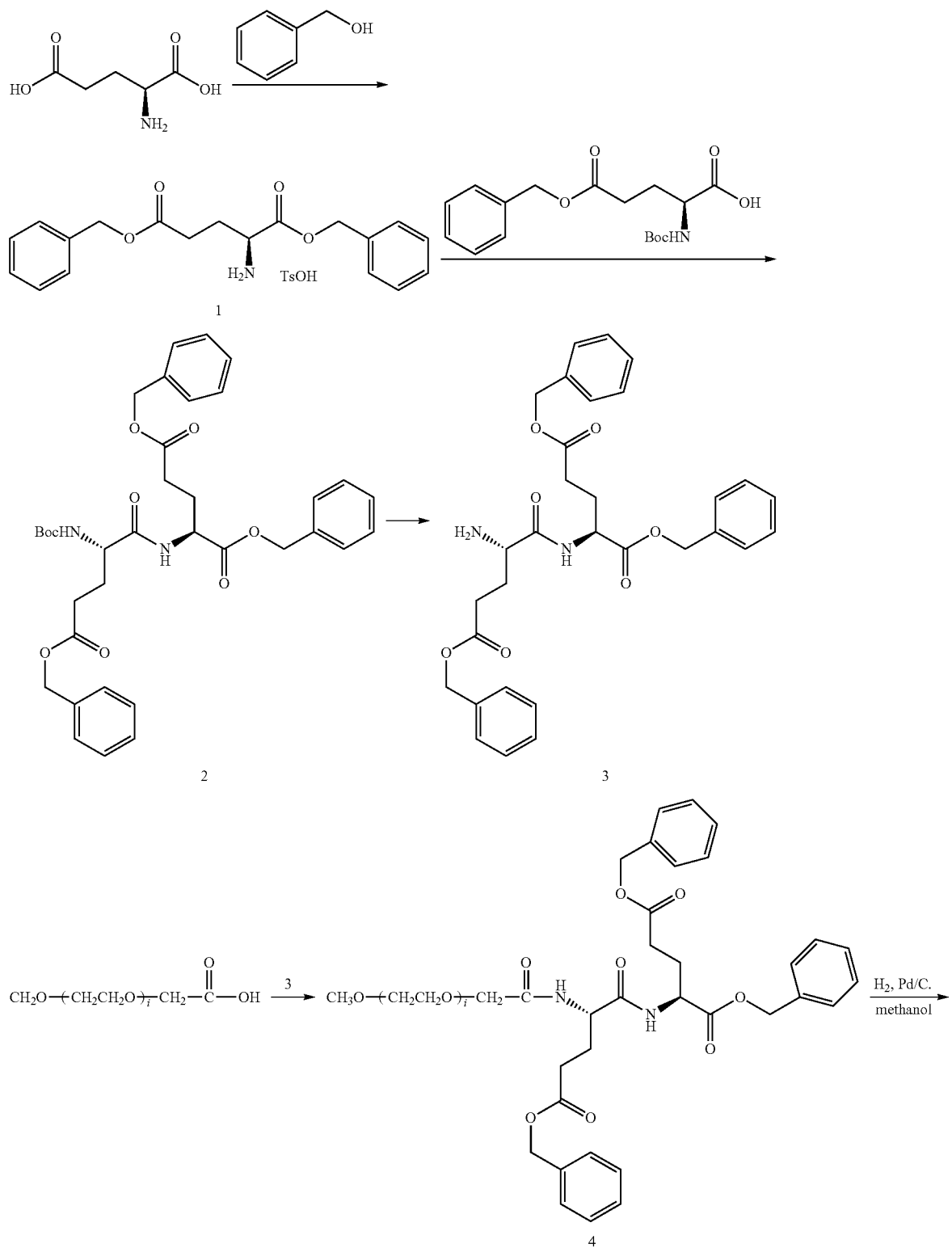

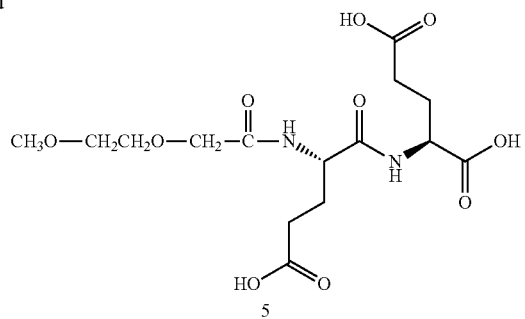

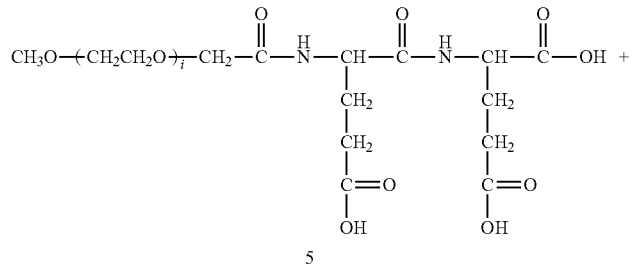

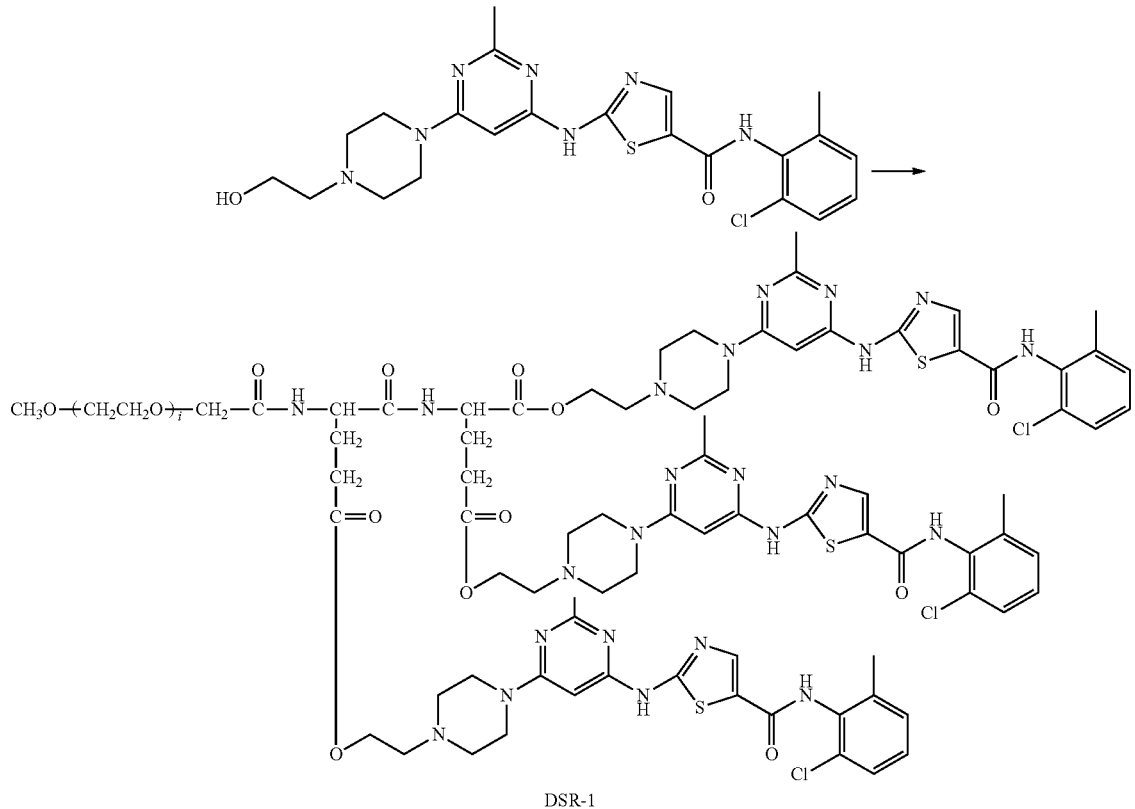

DSR-1

29.4 g (0.2 mol) L-(+)-glutamic acid, 40 g (0.23 mol) p-toluenesulfonic acid, and 80 mL benzyl alcohol were dissolved in 500 mL methylbenzene. 11 mL water was separated out by backflow under the protection of nitrogen gas. The backflow was continued for 3 h, and 150 mL liquid was evaporated and removed. The solution was cooled down to 50° C., and then the reaction solution was poured into a beaker containing 600 mL petroleum ether for stirring 1 h. The precipitation was collected by filtration. The filter cake was dissolved in 280 mL of 95% ethanol by heating, then the heating was stopped and the solution was cooled overnight. The precipitation was collected by filtration and dried in vacuum to produce 61 g L-(+)-glutamic acid dibenzyl ester p-toluenesulfonate (compound 1).

30 g (0.06 mol) of L-(+)-glutamic acid dibenzyl ester p-toluenesulfonate (compound 1) was dissolved in 500 mL dichloromethane. Then, 20.86 g (0.062 mol) tert-butyloxy-carbonyl-L-glutamic acid-5-benzyl ester, 7.55 g (0.062 mol) DMAP and 8.35 g (0.07 mol) HOBt were added. The dichloromethane solution containing 14.3 g DCC was added under the protection of nitrogen gas. After all the reagents were dropped, the system was sealed and reacted overnight.

TLC was used to monitor the completion of the reaction. The solvent was removed by filtration and 20 mL ethyl acetate was added to the concentrated solution. The solid was removed by filtration and 400 mL petroleum ether was added to the mother liquid to precipitate it. The product of 15.8 g N-tert-butyloxycarbonyl dipeptide of benzyl glutamate (compound 2) was produced after the filtration.

0.78 g N-tert-butyloxycarbonyl dipeptide of benzyl glutamate (compound 2) was dissolved in 7 mL dichloromethane. 3 mL trifluoroacetic acid was added and the system reacted at room temperature for 2 h. The solvent was removed and 100 mL dichloromethane was added, and 5% sodium bicarbonate solution was used to adjust the pH to 7-8. The solution was separated by extract, and the organic phase was washed by 5% sodium bicarbonate solution for two times and then dried by anhydrous sodium sulfate. After the filtration, the filter liquid was directly added to the reaction bottle, and 20.0 g (1 mmol) methoxy PEG acetic acid (20K), 245 mg (2 mmol) DMAP and 135 mg (1 mmol) HOBt were added under the protection of nitrogen gas. After they were dissolved completely, 412 mg (2 mmol) DCC was added. The solution was stirred and reacted at room temperature overnight. After filtration, the solvent was removed by rotary evaporation, and 500 mL isopropanol was added to the residues, which was filtered and the product was dried in vacuum. The product was dissolved in 200 mL anhydrous methanol. 1.0 g palladium-carbon was added, the hydrogen was introduced and the system was reacted at room temperature overnight. The palladium-carbon was removed by filtration, the solvent was removed by rotary evaporation.

500 mL isopropanol was added to the residues, which was filtered and the product was dried in vacuum. 13.4 g methoxy PEG dipeptide acid of glutamic acid (20K) (compound 5) was formed.

Methoxy PEG dipeptide acid of glutamic acid (compound 5) (20K, 0.5 g, 0.025 mmol), 73 mg (0.15 mmol) dasatinib, and 24.4 mg (0.2 mmol) DMAP were added to the reaction bottle. The solvent mixture of dichloromethane and N,N-dimethylformamide was used to dissolve them, and the system was cooled in ice bath under the protection of nitrogen gas. Then, the dichloromethane solution containing 41.3 mg (0.2 mmol) DCC was dropped into the solution. After the drop, the system was naturally warmed to room temperature to react overnight. In the next day, the reaction solution was concentrated and the residues were recrystallized by the isopropanol to produce 0.37 g of the conjugate of methoxy PEG dipeptide acid of glutamic acid (20K)-dasatinib (DSR-1). $^1$H-NMR (DMSO-$d_6$): 2.12(s, 9H), 2.13 (m, 2H), 2.17 (m, 2H), 2.40 (t, 4H), 2.44 (s, 9H), 2.51 (t, 6H), 3.30 (s, 3H), 3.44 (t, 12H), 3.50 (s, 2H), 3.54(m, 1800H), 3.60 (t, 6H), 3.62 (t, 12H), 4.45 (t, 1H), 4.53 (t, 1H), 5.28 (s, 3H), 7.01 (m, 3H), 7.26 (m, 3H), 7.44 (m, 3H), 8.03 (s, 2H), 8.10 (s, 3H), 9.15 (s, 3H), 11.44 (s, 3H).

EXAMPLE 2

Preparation of the Conjugate of Methoxy PEG Dipeptide of Glutamic Acid and Glycine (Number-average Molecular Weight of 20,000)-dasatinib (DSR-2)

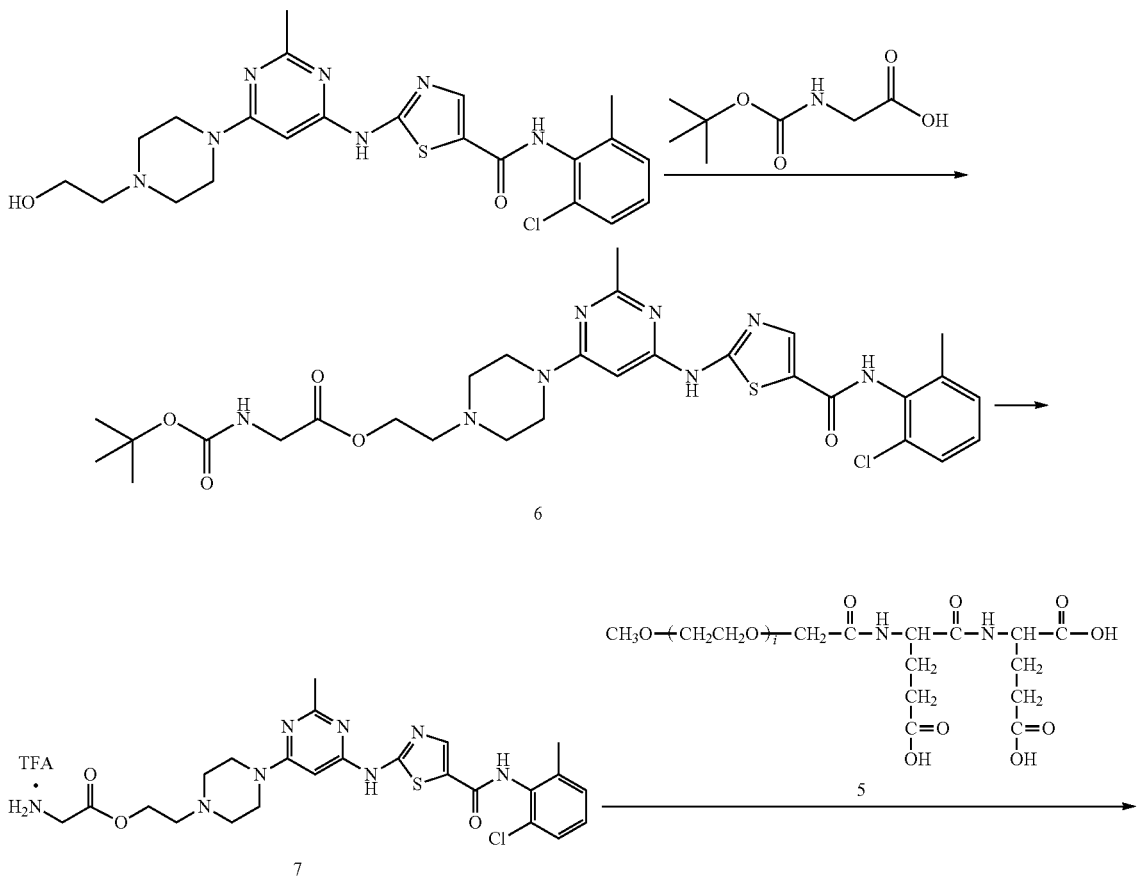

-continued

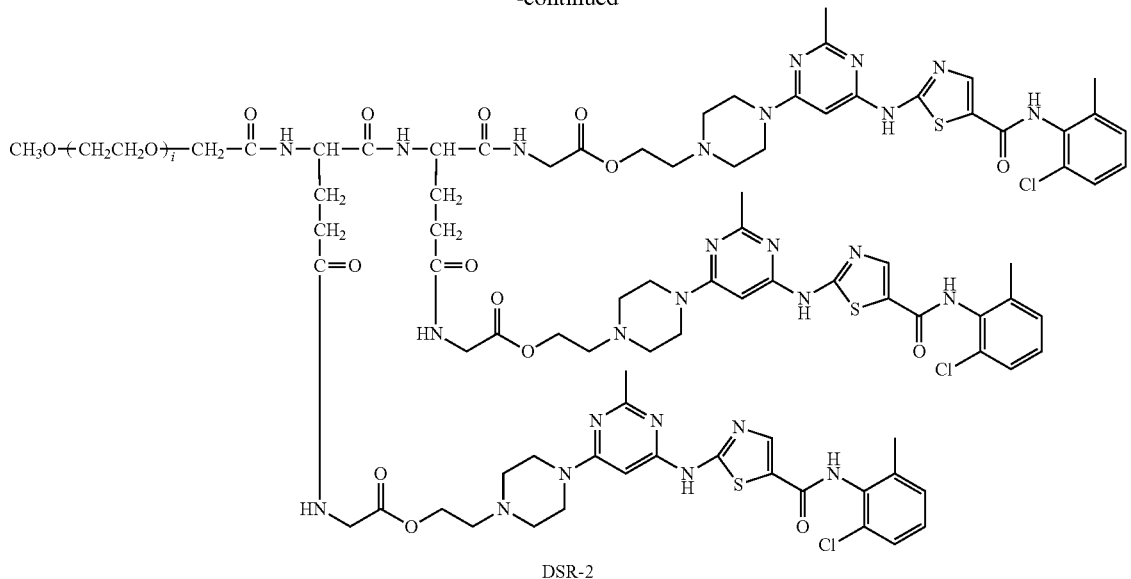

DSR-2

Methoxy PEG dipeptide acid of glutamic acid (compound 5) was prepared according to the method in the Example 1.

1.95 g (4 mmol) Dasatinib, 840 mg (4.8 mmol) N-tert-butyloxycarbonyl glycine and 714 mg (4.8 mmol) DMAP were added to the reaction bottle. 40 mL N,N-dimethylformamide was used to dissolve them, and the system was cooled in ice bath under the protection of the nitrogen gas. Then, 20 mL dichloromethane solution containing 1.03 g (5 mmol) DCC was dropped into the solution. After the drop, the system was naturally warmed to room temperature to react overnight. The solvent was evaporated under reduced pressure after the reaction was detected to be completed by TLC, The residues were separated by column chromatography to produce 1.5 g of N-tert-butyloxycarbonyl glycine dasatinib ester (compound 6) at a yield of 58%. $^1$H-NMR (DMSO-$d_6$): 1.32(s, 9H), 2.15(s, 3H), 2.46(s, 3H), 2.51(m, 2H), 3.53(m, 10H),4.10(s, 2H), 5.88(s, 1H), 7.29(m, 3H), 8.12(s, 1H), 8.28(s, 1H), 9.81(s, 1H), 11.25(s, 1H).

1 g (1.6 mmol) N-tert-butyloxycarbonyl glycine dasatinib ester (compound 6) and 50 mL dichloromethane were added to the reaction bottle, and then trifluoroacetic acid 25 mL was added. After the system was stirred and reacted for 3 h, the solvent was evaporated under reduced pressure. Dichloromethane was added to the residues, which was dried by evaporation under reduced pressure. The step was repeated for three times to produce 1.2 g glycine dasatinib ester trifluoroacetate (compound 7) which was used for the next reaction directly.

Methoxy PEG dipeptide acid of glutamic acid (compound 5) (20K, 0.5 g, 0.025 mmol), 100 mg (0.15 mmol) glycine dasatinib ester trifluoroacetate (compound 7), (3.4 mg, 0.025mmol) HOBt and 24.4 mg (0.2 mmol) DMAP were added to the reaction bottle. The solvent mixture of dichloromethane and N,N-dimethylformamide was used to dissolve them and the system was cooled in ice bath under the protection of the nitrogen gas. The dichloromethane solution containing 36.1 mg (0.175 mmol) DCC was then dropped into the solution. After the drop, the system was naturally warmed to room temperature to react overnight. In the next day, the reaction solution was concentrated and the residues were recrystallized by the isopropanol to produce 0.39 g of the conjugate of methoxy PEG dipeptide of glutamic acid and glycine (20K)-dasatinib (DSR-2). $^1$H-NMR (DMSO-$d_6$): 2.12(s, 9H), 2.13 (m, 2H), 2.17 (m, 2H), 2.40 (t, 4H), 2.44 (s, 9H), 2.97 (t, 6H), 3.30 (s, 3H), 3.44 (t, 12H), 3.50 (s, 2H), 3.51(s, 6H), 3.54(m,1800H), 3.62 (t, 12H), 4.35 (t, 6H), 4.45 (t, 1H), 4.53 (t, 1H), 5.28 (s, 3H), 7.01 (m, 3H), 7.26 (m, 3H), 7.44 (m, 3H), 8.03 (s, 2H), 8.05 (s, 3H), 8.11 (s, 3H), 9.15 (s, 3H), 11.45 (s, 3H).

EXAMPLE 3

Preparation of the Conjugate of Methoxy PEG Dipeptide of Glutamic Acid and Alanine (Number-average Molecular Weight of 20,000)-dasatinib (DSR-3)

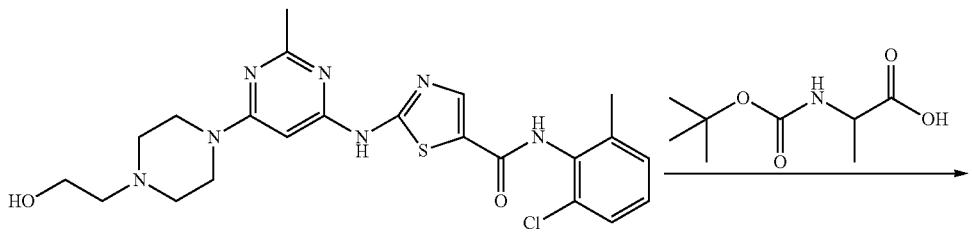

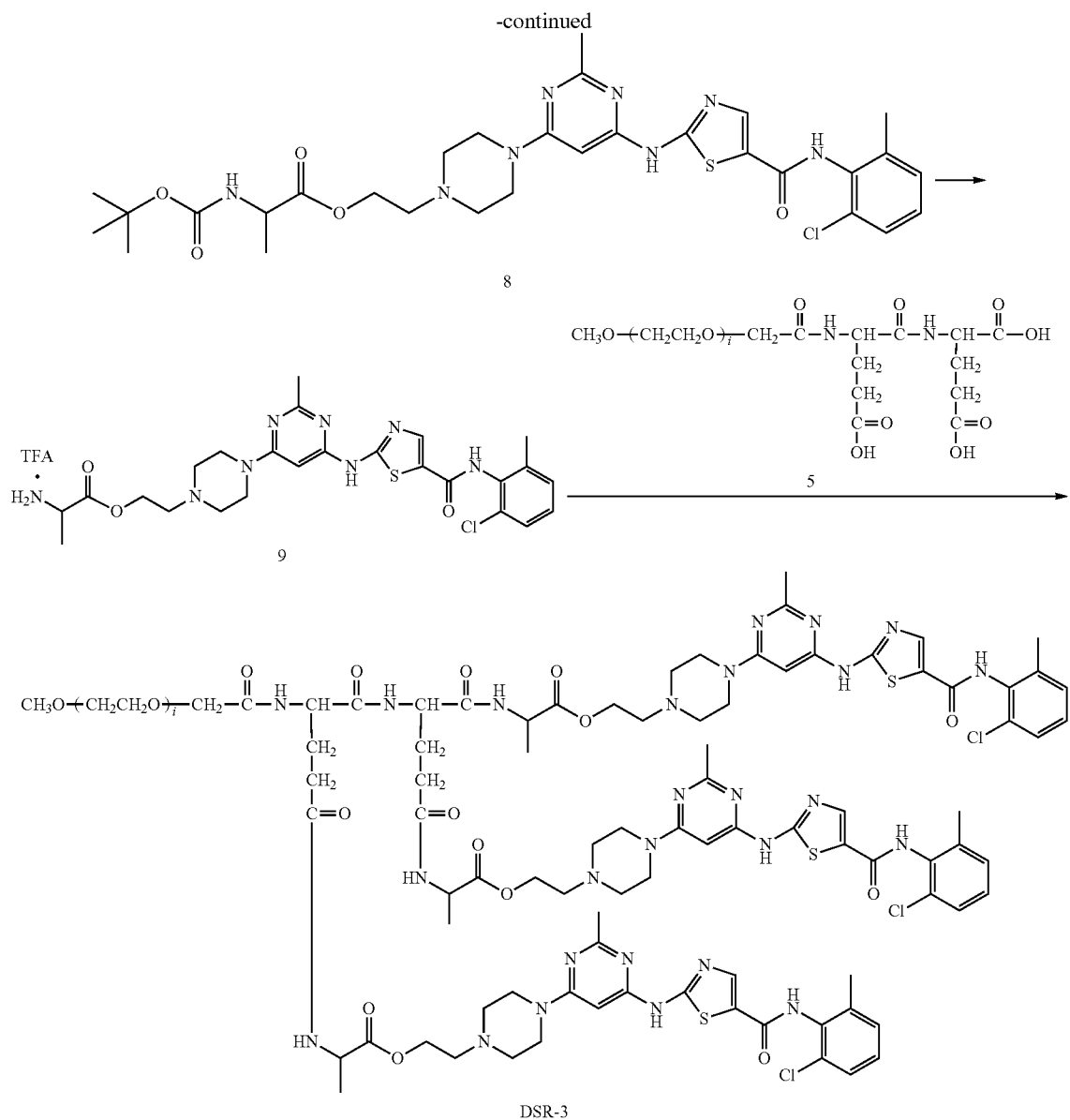

Methoxy PEG dipeptide acid of glutamic acid (compound 5) was prepared according to the method in the Example 1.

1.95 g (4 mmol) dasatinib, 907 mg (4.8 mmol) N-tert-butyloxycarbonyl alanine and 714 mg (4.8 mmol) DMAP were added to the reaction bottle. 40 mL N,N-dimethylformamide was used to dissolve them, and the system was cooled in ice bath under the protection of the nitrogen gas. Then, 20 mL dichloromethane solution containing 1.03 g (5 mmol) DCC was dropped into the solution. After the drop, the system was naturally warmed to room temperature to react overnight. The residues were separated by column chromatography after the reaction was detected to be completed by the TLC. The residues were separated by column chromatography to produce 1.6 g of the N-tert-butyloxycarbonyl alanine dasatinib ester (compound 8) at a yield of 61%. $^1$H-NMR (DMSO-$d_6$): 1.33(s, 9H), 1.49(s, 3H), 2.12 (s, 3H), 2.45(s, 3H), 2.98(m, 2H), 3.46(m, 4H), 3.63(m, 4H), 4.22(m, 2H), 4.31(m, 1H), 5.97(s, 1H), 7.29(m, 3H), 8.15(s, 1H), 8.32(s, 1H), 9.66(s, 1H), 11.17(s, 1H).

1 g (1.6 mmol) N-tert-butyloxycarbonyl alanine dasatinib ester (compound 8) and 50 mL dichloromethane were added to the reaction bottle, and 25 mL trifluoroacetic acid was then added. After the system was stirred and reacted for 3 h, the solvent was evaporated under reduced pressure. Dichloromethane was added to the residues, which was dried by evaporation under reduced pressure. The step was repeated for three times to produce 1.3 g alanine dasatinib ester trifluoroacetate (compound 9) which was used for the following reactions directly.

Methoxy PEG dipeptide acid of glutamic acid (compound 5) (20K, 0.5 g, 0.025 mmol), 102 mg (0.15 mmol) alanine dasatinib ester trifluoroacetate (compound 9), (3.4 mg, 0.025mmol) HOBt and 24.4 mg (0.2 mmol) DMAP were added to the reaction bottle, the solvent mixture of dichloromethane and N,N-dimethylformamide was used to dissolve them, and the system was cooled in ice bath under the protection of the nitrogen gas. Then, the dichloromethane solution containing 36.1 mg (0.175 mmol) DCC was dropped into the solution. After the drop, the system was naturally warmed to room temperature to react overnight. In the next day, the reaction solution was concentrated and the residues were recrystallized by using the isopropanol to produce 0.39 g conjugate of methoxy PEG dipeptide of glutamic acid alanine (20K)-dasatinib (DSR-3). $^1$H-NMR (DMSO-d$_6$): 1.28 (s, 3H), 2.12(s, 9H), 2.13 (m, 2H), 2.17 (m, 2H), 2.40 (t, 4H), 2.44 (s, 9H), 2.97 (t, 6H), 3.30 (s, 3H), 3.44 (t, 12H), 3.50 (s, 2H), 3.54 (m,1800H), 3.62 (t, 12H), 3.63 (m, 3H), 4.18 (t, 6H), 4.45 (t, 1H), 4.53 (t, 1H), 5.28 (s, 3H), 7.01 (m, 3H), 7.26 (m, 3H), 7.44 (m, 3H), 8.03 (s, 2H), 8.05 (s, 3H), 8.10 (s, 3H), 9.15 (s, 3H), 11.44 (s, 3H).

EXAMPLE 4

Preparation of the Conjugate of Methoxy PEG Dipeptide of Glutamic Acid and Valine (Number-average Molecular Weight of 20,000)-dasatinib (DSR-4)

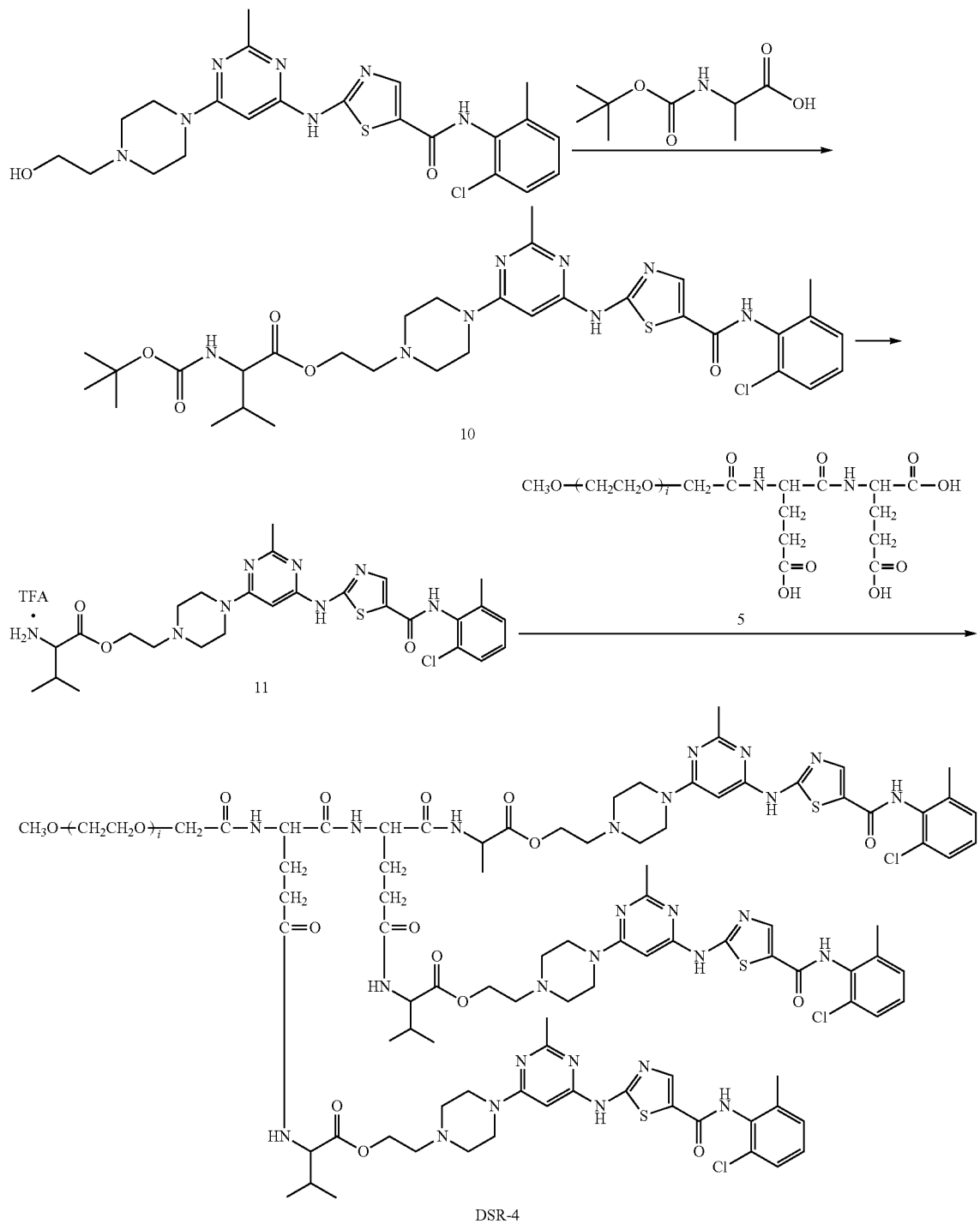

Methoxy PEG dipeptide acid of glutamic acid (compound 5) was prepared according to the method in the Example 1.

1.95 g (4 mmol) Dasatinib, 1.11 g (4.8 mmol) N-tert-butyloxycarbonyl valine and 714 mg (4.8 mmol) DMAP were added to the reaction bottle. 40 mL N,N-dimethylformamide was used to dissolve them, and the system was cooled in ice bath under the protection of the nitrogen gas. Then, 20 mL dichloromethane solution containing 1.03 g (5 mmol) DCC was dropped into the solution. After the drop, the system was naturally warmed to room temperature to react overnight. The solvent was evaporated under reduced pressure after the reaction was detected to be completed by TLC. The residues were separated by column chromatography to produce 1.7 g N-tert-butyloxycarbonyl valine dasatinib ester (compound 10) at a yield of 62%. $^1$H-NMR (DMSO-$d_6$): 1.02 (d, 6H), 1.21 (s, 9H), 2.23(s, 3H), 2.49(s, 3H), 2.51 (m, 4H), 2.78 (m, 6H), 3.53(m, 8H), 6.04(s, 1H), 7.27(m, 2H), 7.40(m, 1H), 8.22(s, 1H), 9.88(s, 1H), 11.48(s, 1H).

1 g (1.5 mmol) N-tert-butyloxycarbonyl valine dasatinib ester, 50 mL dichloromethane, and 25 mL trifluoroacetic acid were added to the reaction bottle. After the system was stirred and reacted for 3 h, the solvent was evaporated under reduced pressure. Dichloromethane was added to the residues, which was dried by evaporation under reduced pressure. The step was repeated for three times to produce 1.4 g valine dasatinib ester trifluoroacetate (compound 11) which was used for the next reaction directly.

Methoxy PEG glutamic acid dipeptide acid (compound 5) (20K, 0.5 g, 0.025 mmol), 140 mg (0.15 mmol) valine dasatinib ester trifluoroacetate (compound 11), (3.4 mg, 0.025 mmo) HOBt and 24.4 mg (0.2 mmol) DMAP were added to the reaction bottle. The solvent mixture of dichloromethane and N,N-dimethylformamide was used to dissolve them, and the system was cooled in ice bath under the protection of the nitrogen gas. Then, the dichloromethane solution containing 36.1 mg (0.175 mmol) DCC was dropped into the solution. After the drop, the system was naturally warmed to room temperature to react overnight. In the next day, the reaction solution was concentrated and the residues were recrystallized by the isopropanol to produce 0.32 g conjugate of methoxy PEG glutamic acid dipeptide valine (20K)-dasatinib (DSR-4). $^1$H-NMR (DMSO-$d_6$): 0.91 (s, 18H), 2.12(s, 9H), 2.13 (m, 2H), 2.17 (m, 2H), 2.40 (t, 4H), 2.44 (s, 9H), 2.67 (m, 3H), 2.97 (t, 6H), 3.30 (s, 3H), 3.44 (t, 12H), 3.46 (d, 3H), 3.50 (s, 2H), 3.54(m,1800H), 3.62 (t, 12H), 4.18 (t, 6H), 4.45 (t, 1H), 4.53 (t, 1H), 5.28 (s, 3H), 7.01 (m, 3H), 7.26 (m, 3H), 7.44 (m, 3H), 8.03 (s, 2H), 8.05 (s, 3H), 8.10 (s, 3H), 9.15 (s, 3H), 11.44 (s, 3H).

EXAMPLE 5

Preparation of the Conjugate of Y Shape PEG Dipeptide of Glutamic Acid and Valine (Number-average Molecular Weight of 40,000)-dasatinib (DSR-5)

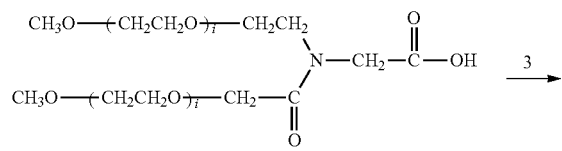

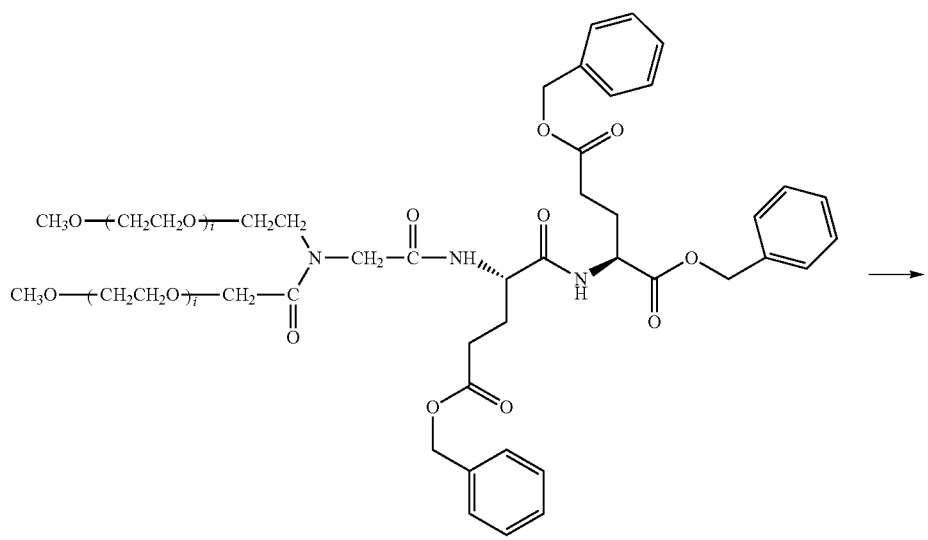

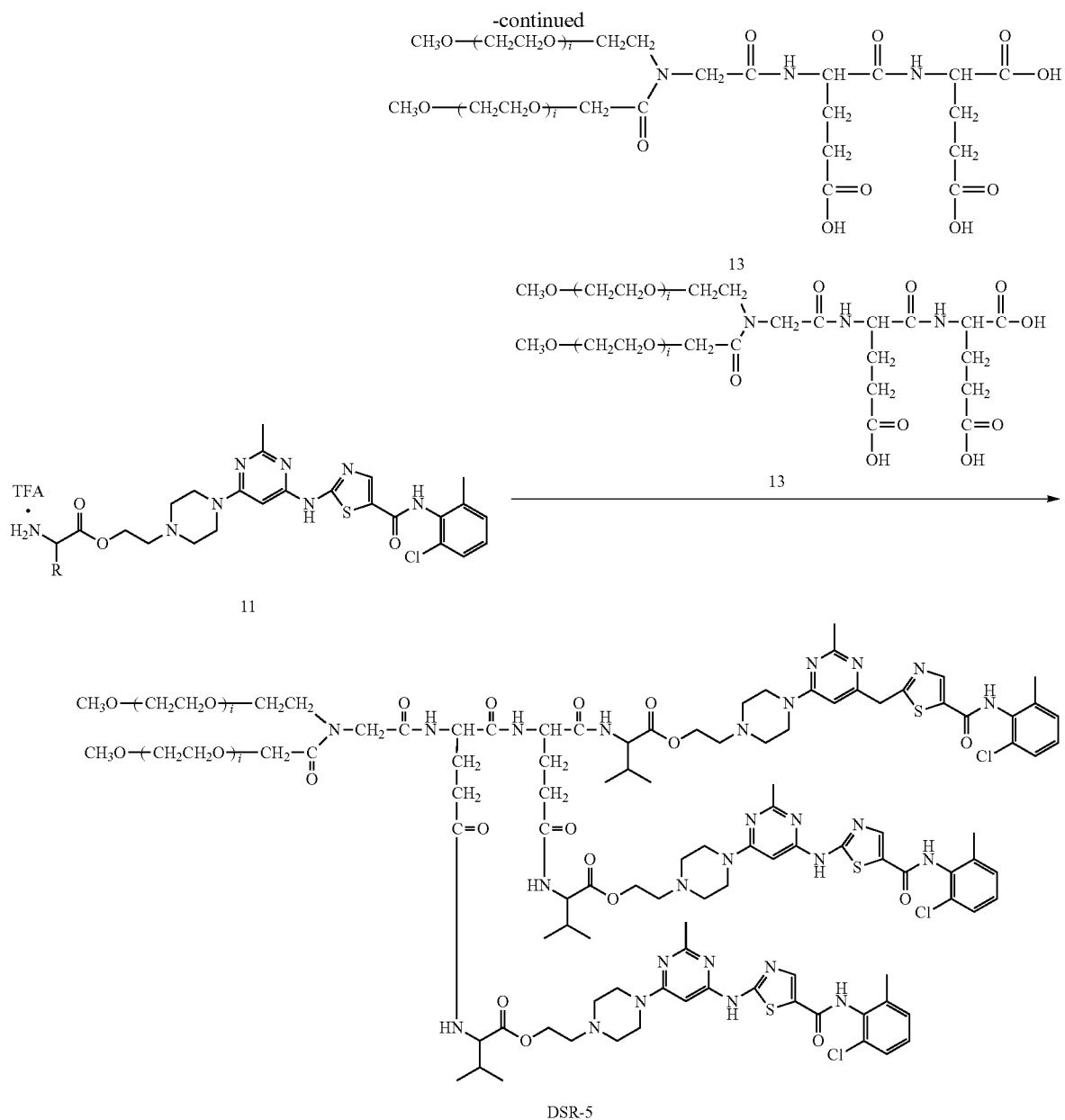

0.78 g N-tert-butyloxycarbonyl dipeptide of benzyl glutamate (compound 2) (Example 1) was dissolved in 7 mL dichloromethane. 3 mL trifluoroacetic acid was added, and the system was reacted at room temperature for 2 h. The solvent was removed, and 100 mL dichloromethane was added and 5% sodium bicarbonate solution was used to adjust pH to 7-8. The solution was separated by extract, and the organic phase was washed by 5% sodium bicarbonate solution for two times and then dried by the anhydrous sodium sulfate. After filtration, the filter liquid was directly added to the reaction bottle, and 40.0 g Y shape PEG acetic acid (40K), 245 mg (2 mmol) DMAP and 135 mg (1 mmol) HOBt were added under the protection of the nitrogen gas. After they were dissolved completely, 412 mg (2 mmol) DCC was added. The solution was stirred and reacted at room temperature overnight. After filtration, the solvent was removed by rotary evaporation. 500 mL isopropanol was added to the residues, which was filtered and the product was dried in vacuum. The product was dissolved in 200 mL anhydrous methanol, and 1.0 g palladium-carbon was added. The hydrogen was introduced and the system was reacted at room temperature overnight. The palladium-carbon was removed by filtration, and the solvent was removed by rotary evaporation. 500 mL isopropanol was added to the residues which were filtered and the product was dried in vacuum. 33.4 g Y shape PEG glutamic acid dipeptide acid (40K) (compound 13) was formed.

Valine dasatinib ester trifluoroacetate (compound 11) was prepared according to the method in the Example 4. Y shape PEG dipeptide acid of glutamic acid (compound 13) (40K, 0.6 g, 0.02 mmol), 112 mg (0.12 mmol) valine dasatinib ester trifluoroacetate, HOBt (2.7 mg, 0.02 mmol) and 24.4 mg (0.2 mmol) DMAP were added to the reaction bottle, the solvent mixture of dichloromethane and N,N-dimethylformamide was used to dissolve them, and the system was cooled in ice bath under the protection of the nitrogen gas.

Then, The dichloromethane solution containing 36.1 mg (0.175 mmol) DCC was dropped into the solution. After the drop, the system was naturally warmed to room temperature to react overnight. In the next day, the reaction solution was concentrated and the residues were recrystallized by the isopropanol to produce 0.39 g conjugate of Y shape PEG glutamic acid dipeptide valine (40K)-dasatinib (DSR-5).
$^1$H-NMR (DMSO-$d_6$): 0.91 (s, 18H), 2.12(s, 9H), 2.13 (m, 2H), 2.17 (m, 2H), 2.40, (t, 4H), 2.44 (s, 9H), 2.67 (m, 3H), 2.97 (t, 6H), 3.30 (s, 6H), 3.37 (t, 2H), 3.44 (t, 12H), 3.46 (d, 3H),3.54 (m,1800H), 3.62 (t, 12H), 3.76 (t, 2H), 4.09 (s, 2H), 4.18 (t, 6H), 4.26 (s, 2H), 4.45 (t, 1H), 4.53 (t, 1H), 5.28 (s, 3H), 7.01 (m, 3H), 7.26 (m, 3H), 7.44 (m, 3H), 8.03 (s, 2H), 8.05 (s, 3H), 8.10 (s, 3H), 9.15 (s, 3H), 11.44 (s, 3H).

EXAMPLE 6

Preparation of the Conjugate of Methoxy PEG Tripeptide of Glutamic Acid and Valine (Number-Average Molecular Weight of 20,000)-dasatinib (DSR-6)

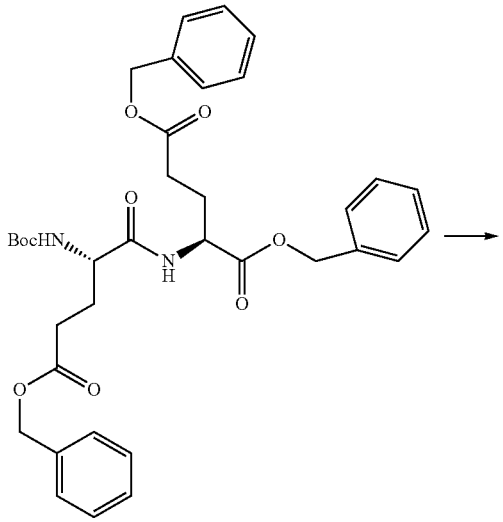

2

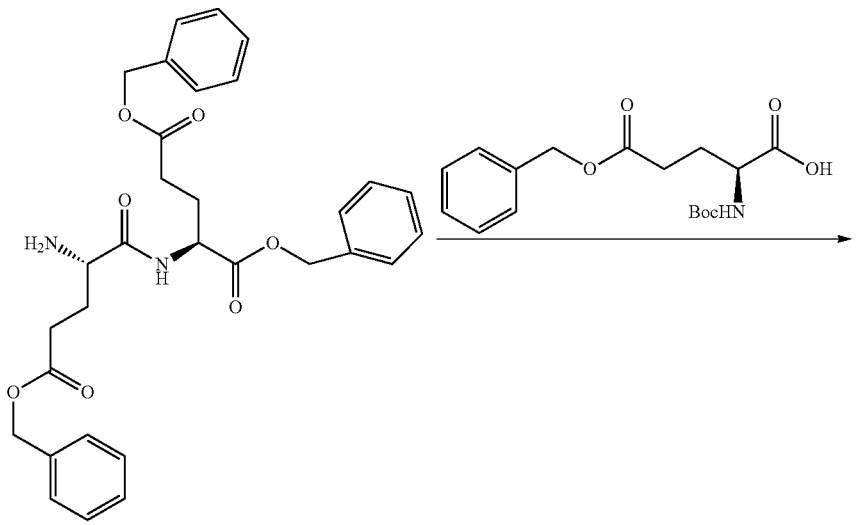

3

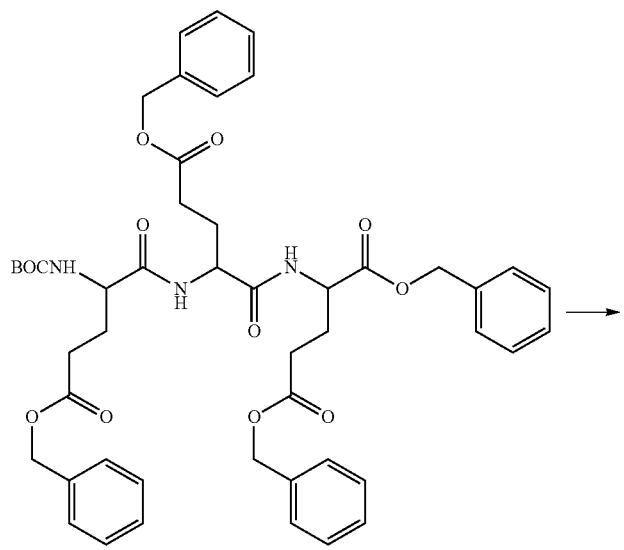
14
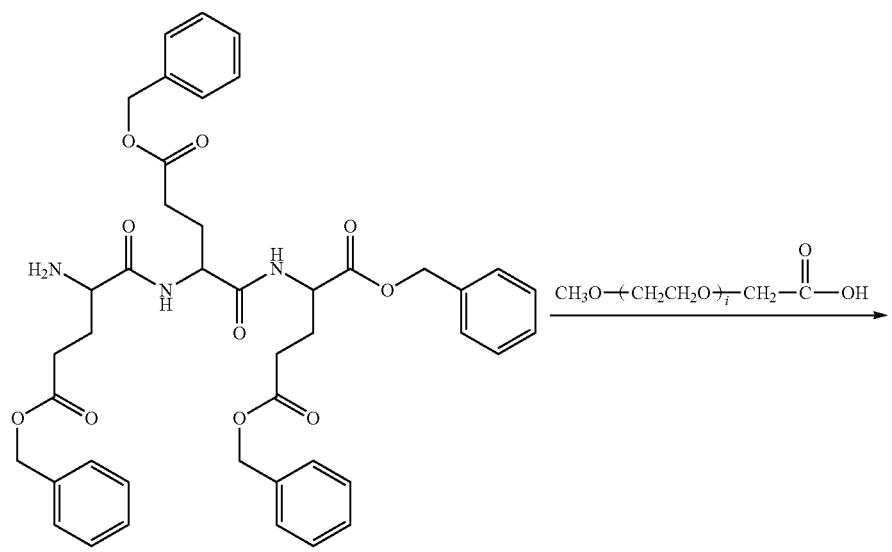
15

-continued
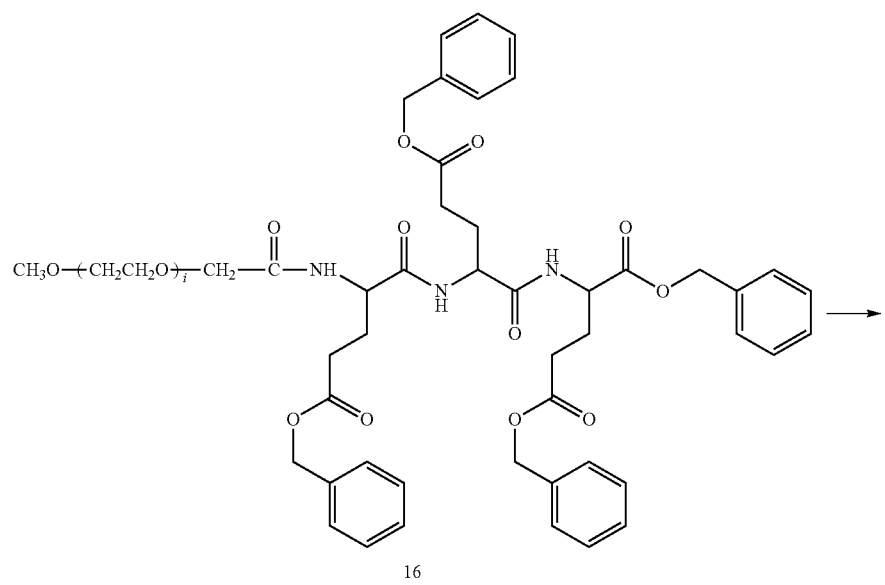
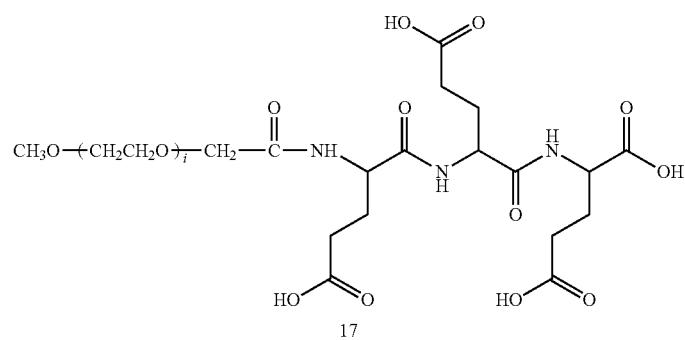
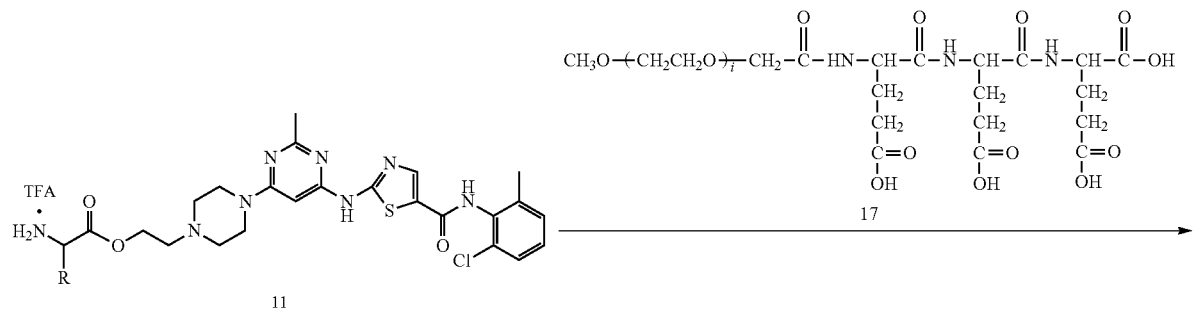

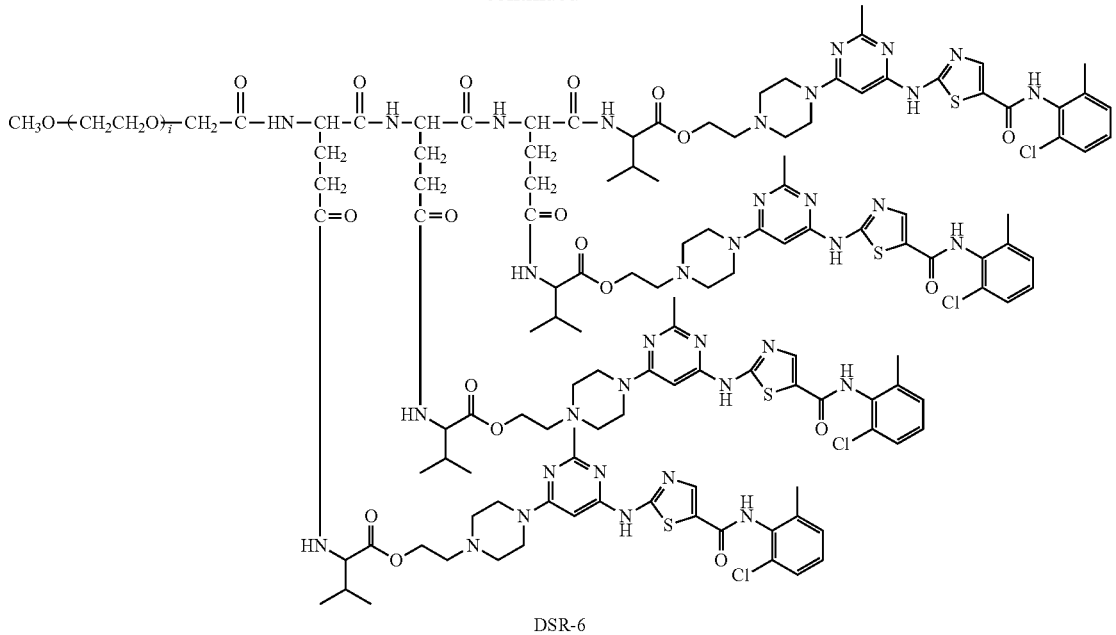

DSR-6

6.47 g (0.01 mol) N-tert-butyloxycarbonyl dipeptide of benzyl glutamate (compound 2) was dissolved in 15 mL dichloromethane. 6 mL trifluoroacetic acid was added and the system was reacted at room temperature for 2 h. The solvent was removed, and 100 mL dichloromethane was added and 5% sodium bicarbonate solution was used to adjust pH to 7-8. The solution was separated by extract, and the organic phase was washed by 5% sodium bicarbonate solution for two times and then dried through the anhydrous sodium sulfate. After filtration, the filter liquid was directly added to the reaction bottle, and 3.37 g (0.01 mol) tert-butyloxycarbonyl-L-glutamic acid-5-benzyl ester, 1.22 g (0.01 mol) DMAP and 1.35 g (0.01 mol) HOBt were added under the protection of the nitrogen gas. After they were dissolved completely, the dichloromethane solution containing 2.39 g (0.011 mol) DCC was added. After all the reagents were dropped, the system was sealed and reacted overnight. TLC was used to monitor that the end of the reaction. After filtration, the system was washed sequentially by 10% citric acid (30 mL*3), 5% sodium bicarbonate (30 mL*3) and 5% saturated sodium chloride aqueous solution (30 mL*3) and then dried by the anhydrous sodium sulfate. After the filtration, the solvent was removed and 25 mL ethyl acetate was added to the concentrated solution. The solid was removed by the filtration and 400 mL petroleum ether was added to the mother solution to precipitate it. The system was filtered to produce 6.8 g N-tert-butyloxycarbonyl tripeptide of benzyl glutamate (compound 14).

1.04 g (1 mmol) N-tert-butyloxycarbonyl tripeptide of benzyl glutamate (compound 14) was dissolved in 7 mL dichloromethane. 3 mL trifluoroacetic acid was added and the system was reacted at room temperature for 2 h. The solvent was removed, and 200 mL dichloromethane was added and 5% sodium bicarbonate solution was used to adjust pH to 7-8. The solution was separated by extract, and the organic phase was washed by 5% sodium bicarbonate solution for two times and then dried by the anhydrous sodium sulfate. After filtration, the filter liquid was directly added to the reaction bottle, and 20.0 g (1 mmol) methoxy PEG acetic acid (20K), 245 mg (2 mmol) DMAP and 135 mg (1 mmol) HOBt were added under the protection of the nitrogen gas. After they were dissolved completely, 412 mg (2 mmol) DCC was added. The system was stirred and reacted at room temperature overnight. After filtration, the excessive solvent was removed by rotary evaporation, 500 mL isopropanol was added to the residues, which was filtered and the product was dried in vacuum. The product was dissolved in 200 mL anhydrous methanol, 1.0 g palladium-carbon was added. The hydrogen was introduced and the system was reacted at room temperature overnight. The palladium-carbon was removed by filtration, and the solvent was removed by rotary evaporation. 500 mL isopropanol was added to the residues, which was filtered and the product was dried in vacuum to produce 15.4 g Methoxy PEG tripeptide acid of glutamic acid (20K) (compound 17).

Valine dasatinib ester trifluoroacetate (compound 11) was prepared according to the method in the Example 4. Methoxy PEG tripeptide acid of glutamic acid (compound 17) (20K, 0.6 g, 0.03 mmol), 224 mg (0.24 mmol) valine dasatinib ester trifluoroacetate (compound 11), HOBt (4 mg, 0.03 mmol) and 29.3 mg (0.24 mmol) DMAP were added to the reaction bottle. The solvent mixture of dichloromethane and N,N-dimethylformamide was used to dissolve it, and the system was cooled in ice bath under the protection of the nitrogen gas. Then, the dichloromethane solution containing 43.3 mg (0.21 mmol) DCC was dropped into the solution. After the drop, the system was naturally warmed to room temperature to react overnight. In the next day, the reaction solution was concentrated and the residues were recrystallized by the isopropanol to produce 0.45 g conjugate of methoxy PEG tripeptide of glutamic acid and valine (20K)-dasatinib (DSR-6).

$^1$H-NMR (DMSO-$d_6$): 0.91 (s, 24H),1.93 (m, 2H), 2.05 (t, 2H), 2.12(s, 12H), 2.13 (m, 2H), 2.17 (m, 2H), 2.40, (t, 4H), 2.44 (s, 12H), 2.67 (m, 4H), 2.97 (t, 8H), 3.30 (s, 3H), 3.44 (t, 16H), 3.46 (d, 4H),3.50 (s, 2H), 3.54(m,1800H), 3.56 (t, 2H), 3.62 (t, 16H), 4.18 (t, 8H), 4.45 (t, 1H), 4.53 (t, 1H), 5.28 (s, 4H), 7.01 (m, 4H), 7.26 (m, 4H), 7.44 (m, 4H), 8.03 (s, 3H), 8.05 (s, 4H), 8.10 (s, 4H), 9.15 (s, 4H), 11.44 (s, 4H).

EXAMPLE 7

In Vitro Degradation Assay of the Compounds DSR1~6

In order to determine the degradation of the compounds in PBS buffer solution, the compounds DSR1~6 were dissolved in 0.01 M PBS buffer solution, and were sampled every 30 min. The degradation is shown in FIG. 1.

As it shows in the figure, degradation happened to several compounds at different degrees in the PBS buffer solution over time. The compound DSR-1 degraded most quickly, with 60% degradation at 60 min; the compounds DSR-2 and DSR-3 degraded relatively slower, with 50% degradation at 90 min and 150 min respectively; the compounds DSR-4, DSR-5 and DSR-6, different from the former three compounds, degraded much slower, and only 20% degradation occurred at 240 min, which shows that the stability of the DSR-4, DSR-5 and DSR-6 was much better than DSR-1, DSR-2 and DSR-3. It can been seen that the conjugate of drug linked by two types of amino acids (i.e. DSR-2, DSR-3, DSR-4, DSR-5 and DSR-6) was more stable than the drug molecule linked by one amino acid only (i.e. DSR-1). When valine was used as the second amino acid for linking the drugs, the stability of the conjugate was significantly improved.

EXAMPLE 8

Anti-cancer Effects of Different Conjugates of PEG Dasatinib in Subcutaneous Tumor Model of K562 Human Chronic Myelogenous Leukemia Experiment Methods:

K562 cells were subcutaneously inoculated at the back of NOD/SCID mice right side so as to establish a subcutaneous xenograft animal model of human chronic myelogenous leukemia. When the average tumor volume reached 130 mm$^3$, the experiment mice were divided to different groups, with 8 mice for each group, and the drugs were administrated by intravenous injections twice a week. The effect was evaluated based on relative tumor proliferation ratio (T/C %).

Experiment Steps:

(1) Cell Culture

K562 cell line was in vitro cultured in RPMI-1640 medium with supplement of 10% fetal calf serum and L-glutamine (2 mM) at 37° C. in an atmosphere with 5% $CO_2$. Tumor cells were routinely passaged twice a week. Tumor cells in exponential growth phase were collected, then suspended in a mixture of PBS: matrigel with equal volume ratio and placed on ice for tumor inoculation.

(2) Animal Grouping $5 \times 10^6$ K562 cells were subcutaneously inoculated at the back of experiment mice right side. The mice were monitored at regular intervals for the tumor growth. When tumor grew to average 130 mm$^3$, the mice were divided to groups randomly according to tumor volume and mouse body weight, and were administrated.

(3) Experiment Observation

All of the operations relevant to operation, nursing and treatment in this investigation were conducted according to guidelines approved by Association for Assessment and Accreditation of Laboratory Animal Care (AAALAC). After the incoluation, the incidence of disease and death of animals were observed every day. In the process of daily observation, the effects of tumor growth on normal behavior of animals (such as exercise, feeding, drinking, body weight change, eyes, hair) as well as any other abnormality were attentively monitored. Death and clinical symptom were recorded for animals in each group.

(4) Results Analysis

The mouse body weight and the tumor size were measured twice a week during the whole experiment process. The calculation formula for tumor volume is as follows: tumor volume (mm$^3$)=0.5×(long diameter of the tumor× short diameter of the tumor$^2$). RTV and T/C ratios were calculated according to the tumor volumes of the treatment groups and the control group. RTV refers to relative tumor volume. T/C ratio refers to the percentage value of the average tumor volumes between the treatment groups and the control group at a time point after the treatment, which reflects the anti-tumor effects of different treatment groups.

(5) Statistical Analysis

All the experiment results were expressed as the average tumor volume±SE (standard error). For statistical analysis, since the variances of relative tumor volume data were different, one-way analysis of variance (one-way ANOVA) and Dunnett T3 method for multiple comparisons were used to compare significant difference of relative tumor volumes between the groups. $p<0.05$ indicated the significant difference.

Experiment results: the tumor growth of each treatment group and the solvent control group were shown in Tables 1 and 2.

TABLE 1

T/C% value of tumor volume for each treatment group (5 mg/kg) (compared with the solvent control group)

| | The 14$^{th}$ day after the grouping | | | |
|---|---|---|---|---|
| Treatment group | Tumor volume ($\bar{x} \pm$ SE) | Relative tumor volume ($\bar{x} \pm$ SE) | T/C (%) | P value |
| Group 1 solvent | 2447 ± 329 | 1819.4 ± 120.2 | — | — |
| Group 2 dasatinib | 311 ± 55 | 226.9 ± 30.0 | 12.4 | <0.001 |
| Group 3 DSR-4 | 39.2 ± 6 | 29.1 ± 4.8 | 1.6 | <0.001 |
| Group 4 DSR-5 | 178.6 ± 58 | 132.8 ± 35.9 | 7.3 | <0.001 |
| Group 5 DSR-6 | 137 ± 41 | 101.9 ± 19.3 | 5.8 | <0.001 |

TABLE 2

T/C% value of tumor volume for each treatment group (5 mg/kg) (compared with the dasatinib group)

| | The 21$^{st}$ day after grouping | | | |
|---|---|---|---|---|
| Treatment group | Tumor volume ($\bar{x} \pm$ SE) | Relative tumor volume ($\bar{x} \pm$ SE) | T/C (%) | P value |
| Group 2 dasatinib | 391 ± 79 | 289.1 ± 46.9 | — | — |
| Group 3 DSR-4 | 176 ± 59 | 130 ± 28 | 45 | <0.001 |
| Group 4 DSR-5 | 203 ± 78 | 150.3 ± 32 | 52 | <0.001 |
| Group 5 DSR-6 | 258 ± 89 | 191 ± 55 | 66 | <0.001 |

Due to fast growth of the subcutaneous tumor model of K562 human chronic myelogenous leukemia, the experiment on the solvent control group was stopped at the 14$^{th}$ day after the grouping and treatment because the average tumor volume (2,447 mm$^3$) exceeds 2,000 mm$^3$. In the 14$^{th}$ day after the grouping and treatment, the differences of the effect between the positive drug dasatinib (5 mg/kg) and the solvent control group were statistically significant (p<0.001). The average tumor volume of the positive drug dasatinib is 311 mm$^3$ and relative tumor proliferation ratio (T/C %) is 12.4%. The differences of the effect between the tested drugs DSR-4, DSR-5 and DSR-6 (5 mg/kg) and the solvent control group were statistically significant (p<0.001). The average tumor volume of DSR-4, DSR-5 and DSR-6 is 39.2 mm$^3$, 178.6 mm$^3$, and 137 mm$^3$, respectively, and the relative tumor proliferation ratio (T/C %) is 1.6%, 7.3% and 5.8%, respectively.

In the 21$^{st}$ day after the grouping and treatment, the average tumor volume of the dasatinib (5 mg/kg) group is 391 mm$^3$. The differences of the effect between the tested drugs DSR-4, DSR-5 and DSR-6 (5 mg/kg) and the dasatinib group were all statistically significant (p<0.001). The average tumor volume of DSR-4, DSR-5 and DSR-6 is 176 mm$^3$, 203 mm$^3$, and 258 mm$^3$, respectively and relative tumor proliferation ratio (T/C %) is 45%, 52% and 66%, respectively.

Compared with the solvent control group, the relative tumor proliferation rates (T/C %) of the positive drug dasatinib (5 mg/kg) and the tested drugs DSR-4, DSR-5 and DSR-6 (5 mg/kg) is 12.4%, 1.6%, 7.3% and 5.8%, respectively. This result indicated that all the compounds had significant anti-K562 tumor growth effects (all of the p<0.001). Compared with the dasatinib (5 mg/kg), the anti-tumor effects of DSR-4, DSR-5 and DSR-6 at the same dose (5 mg/kg) were significantly better (all of the p<0.001).

EXAMPLE 9

Effects of Different Conjugates of PEG Dasatinib on Subcutaneous Tumor Model of PC-3 Human Prostate Cancer Experiment Methods:

PC-3 cells were subcutaneously inoculated at the right side on the back of Balb/c nude mouse so as to establish a subcutaneous xenograft animal model of human prostate cancer. When the average tumor volume reached 160 mm$^3$, the experiment mice were divided to different groups, with 8 mice for each group, and the drugs were administrated by intravenous injections twice a week. The therapeutic effect was evaluated based on relative tumor proliferation ratio (T/C %).

Experiment Steps:

(1) Cell Culture

PC-3 cell line was cultured in vitro in Ham's F12K medium with supplement of 10% fetal calf serum and L-glutamine (2 mM) at 37° C. in an atmosphere with 5% CO$_2$ for the tumor cells culture. The tumor cells were routinely passaged twice a week. Tumor cells in exponential growth phase were collected, then were suspended in a mixture of PBS: matrigel with equal volume ratio and were placed on ice for tumor inoculation.

(2) Animal Grouping

5×10$^6$ PC-3 cells were subcutaneously inoculated at the right side on the back of experiment mice. The mice were monitored at regular intervals for the tumor growth. When tumor grew to average 160 mm$^3$, the mice were divided to groups randomly according to the tumor volume and the mouse body weight, and were administrated.

(3) Experiment Observation

All of the operations relevant to operation, nursing and treatment in this investigation were conducted according to guidelines approved by Association for Assessment and Accreditation of Laboratory Animal Care (AAALAC). After the incoulation, the incidence of disease and death of animals were observed every day. In the process of daily observation, the effects of tumor growth on normal behavior of animals (such as exercise, feeding, drinking, body weight change, eyes, hair) as well as any other abnormality were attentively monitored. Death and clinical symptom were recorded for animals in each group.

(4) Results Analysis

The mouse body weight and the tumor size were measured twice a week during the whole experiment process. The calculation formula for tumor volume is as follows: tumor volume (mm$^3$)=0.5×(long diameter of the tumor× short diameter of the tumor$^2$). RTV and T/C ratios were calculated according to the tumor volumes of the treatment groups and the control group. RTV refers to relative tumor volume. T/C ratio refers to the percentage value of the relative tumor volumes of the treatment groups and the control group at a time point after the treatment, which reflects the anti-tumor effects of different treatment groups. At the end of the experiment, the pictures of the tumors were recorded according to the following two methods: 1. after euthanatized by CO$_2$, the animals in each group were placed with tumor-bearing side up, and the pictures were taken and recorded respectively for each group; 2. after the tumor was removed, the tumor weight was weighed first. T/C (percentage value of the tumor weight between the treatment group and the control group) was calculated, and then the tumors from each group were placed in order. The pictures of the tumors were taken and recorded.

(5) Statistical Analysis

All the experiment results were expressed as average tumor volume±SE (standard error). For statistical analysis, one-way analysis of variance (one-way ANOVA) and LSD multiple comparisons method were used for the relative tumor volume data, comparing the significant difference of the relative tumor volumes between the groups. p<0.05 indicates the significant difference.

Experiment Results:

The tumor growth conditions of each treatment group and the solvent control group were shown in Tables 3 and 4.

TABLE 3

T/C% value of tumor volume for each treatment group (10 mg/kg) (compared with the solvent control group)

| | 22$^{nd}$ day after grouping | | | |
|---|---|---|---|---|
| Treatment group | Tumor volume ($\bar{x}$ ± SE) | Relative tumor volume ($\bar{x}$ ± SE) | T/C (%) | P value |
| Group 1 solvent | 2462 ± 158 | 1572.6 ± 133.0 | — | — |
| Group 2 dasatinib | 1752 ± 76 | 1148.9 ± 112.7 | 73 | 0.002 |
| Group 3 DSR-4 | 1187 ± 67 | 745.9 ± 54.4 | 47 | <0.001 |
| Group 4 DSR-5 | 1380 ± 112 | 894.2 ± 77.8 | 57 | <0.001 |
| Group 5 DSR-6 | 1439 ± 136 | 885.8 ± 66.9 | 56 | <0.001 |

TABLE 4

T/C% value of tumor volume for each treatment group (10 mg/kg) (compared with the dasatinib group)

| | 25$^{th}$ day after grouping | | | |
|---|---|---|---|---|
| Treatment group | Tumor volume ($\bar{x}$ ± SE) | Relative tumor volume ($\bar{x}$ ± SE) | T/C (%) | P value |
| Group 2 dasatinib | 1868 ± 76 | 1235.3 ± 119.6 | — | — |
| Group 3 DSR-4 | 1200 ± 113 | 751.9 ± 78.9 | 61 | 0.030 |

TABLE 4-continued

T/C% value of tumor volume for each treatment group
(10 mg/kg) (compared with the dasatinib group)

| | 25th day after grouping | | | |
|---|---|---|---|---|
| Treatment group | Tumor volume ($\bar{x}$ ± SE) | Relative tumor volume ($\bar{x}$ ± SE) | T/C (%) | P value |
| Group 4 DSR-5 | 1406 ± 116 | 928.6 ± 106.6 | 75 | 0.015 |
| Group 5 DSR-6 | 1449 ± 164 | 887.4 ± 79.1 | 72 | 0.001 |

The tumor in the subcutaneous tumor model of PC-3 human prostate cancer grew fast and led to decrease of the mouse body weight when the tumor burden increased. The experiment on the solvent control group was stopped at the 22nd day after the grouping and treatment because the average tumor volume (2,462 mm³) exceeded 2,000 mm³. In the 22nd day after the grouping and treatment, the differences of the effect between the positive drug dasatinib (10 mg/kg) and the solvent control group were statistically significant (p<0.001). The average tumor volume of the positive drug dasatinib is 1,752 mm³ and the relative tumor proliferation ratio (T/C %) is 73%; the differences of the effect between the tested drugs DSR-4, DSR-5 and DSR-6 (10 mg/kg) and the solvent control group were statistically significant (p<0.001). The average tumor volume of DSR-4, DSR-5 and DSR-6 is 1187 mm³, 1380 mm³ and 1439 mm³, respectively, and the relative tumor proliferation ratio (T/C %) is 47%, 57% and 56%, respectively.

In the 25th day after the grouping and treatment, the average tumor volume of the dasatinib (10 mg/kg) group was 1,868 mm³. The differences of the effect between the tested drugs DSR-4, DSR-5 and DSR-6 (10 mg/kg) and the dasatinib group were all statistically significant (p<0.05, p<0.05 and p<0.01). The average tumor volume of DSR-4, DSR-5 and DSR-6 is 1,200 mm³, 1,406 mm³ and 1,449 mm³, respectively, and the relative tumor proliferation ratio (T/C %) is 61%, 75% and 72%, respectively.

Compared with the solvent control group, the relative tumor proliferation ratios (T/C %) of the positive drug dasatinib (10 mg/kg) and the tested drugs DSR-4, DSR-5 and DSR-6 (10 mg/kg) were 73%, 47%, 57% and 56%, respectively. This result indicated that all the compounds had statistically significant effect of anti-PC-3 tumor growth (all of the p<0.001). Compared with dasatinib (10 mg/kg), the anti-tumor effects of DSR-4, DSR-5 and DSR-6 at the same dose (10 mg/kg) were significantly better (all of the p<0.05).

EXAMPLE

Conjugates of Rapamycin

The rapamycin used in the present example was purchased from Wuhan Yuancheng Gongchuang Technology Co., Ltd. Tert-Butyl bromoacetate and triphenyl phosphine were purchased from Sinopharm Chemical Reagent Co., Ltd.

EXAMPLE 10

Preparation of the conjugate of methoxy PEG acetic acid glycine (number-average molecular weight of 20,000)-rapamycin (LPR-1)

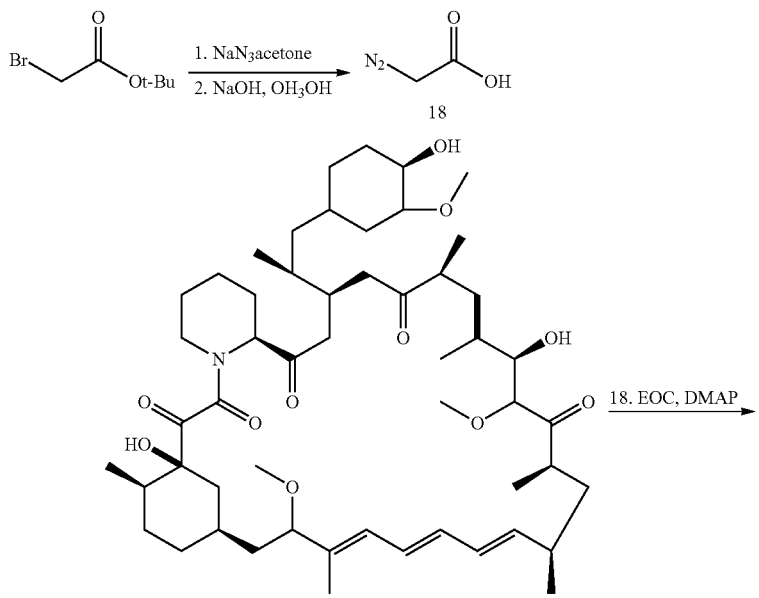

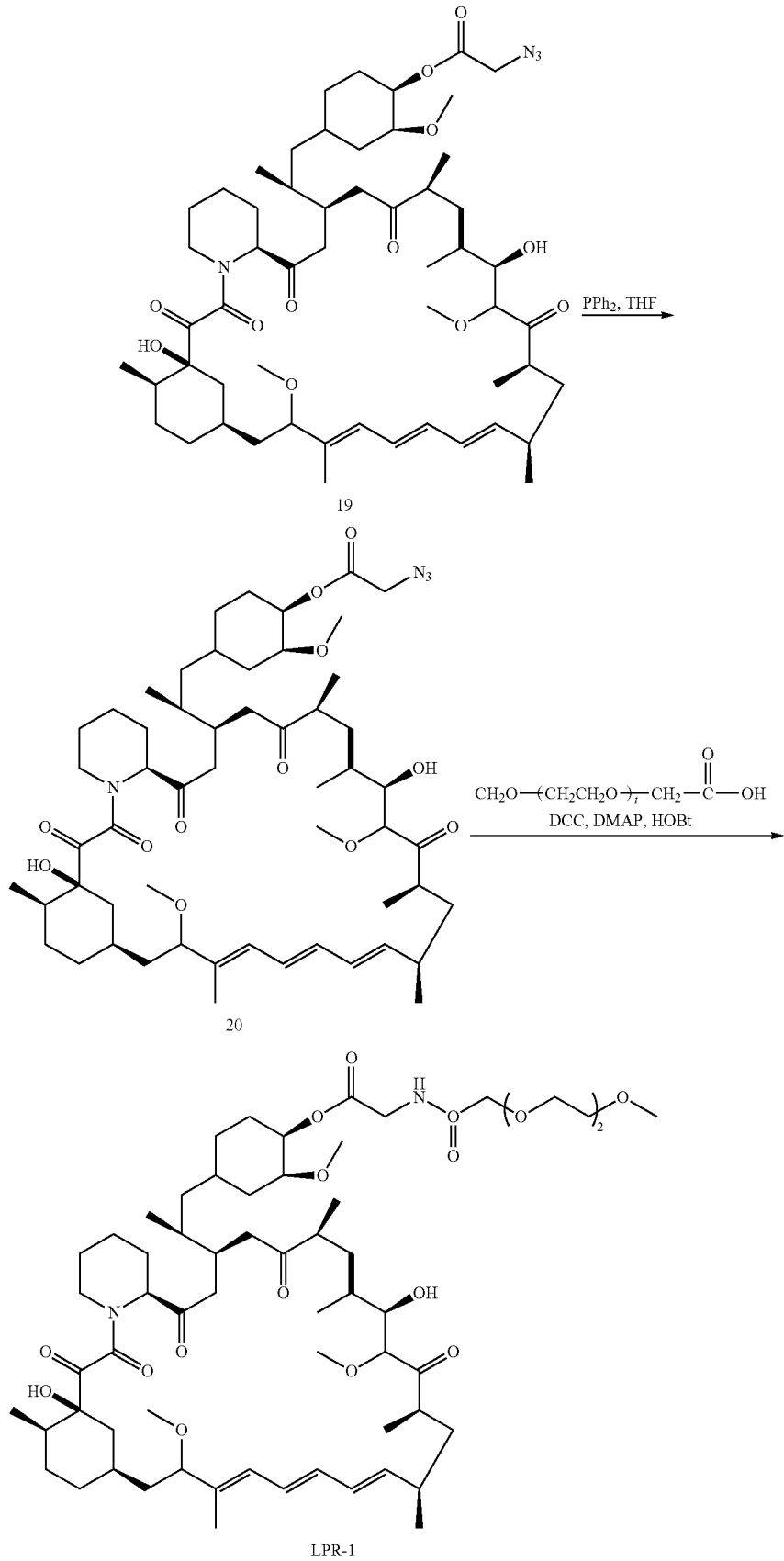

Tert-Butyl bromoacetate (5.82 g, 30 mmol) was added to the reaction bottle. Acetone (80 mL) was used to dissolve it, then aqueous solution (40 mL) containing sodium azide (4.55 g, 70 mmol) was added and the system was heated to conduct backflow overnight. The acetone was removed by evaporating the reaction solution, and the residues were extracted by ether. The extract solution was washed by saturated saline and dried, which was concentrated under reduced pressure to produce oil liquid. This liquid was dissolved in methanol (90 mL), and 1 N sodium hydroxide solution (90 mL) was added, and the system was stirred and then heated to backflow for 3 h. After the system was cooled, the methanol was removed by evaporation under reduced pressure and the residual solution was cooled in ice bath. 6 N hydrochloric acid was used to adjust pH to 2, and ether was then used to extract the system. The extract solution was washed by water, and dried and concentrated to produce azidoacetic acid (compound 18), MS m/z: 124 [M+Na]$^+$.

Azidoacetic acid (compound 18) (253 mg, 2.5 mmoL) and rapamycin (2.28 g, 2.5 mmoL) were added to the reaction bottle, and dichloromethane was used to dissolve them, and the system was cooled in ice bath. 4-dimethylaminopyridine (DMAP, 611 mg, 5 mmoL) and N,N-dicyclohexylcarbodiimide (DCC, 1.03 g, 5 mmoL) were added to the reaction bottle, and then, the system was stirred continuously at room temperature overnight. After the reaction solution was concentrated, the residues were purified by column chromatography to produce 1.42 g azidoacetic acid rapamycin ester (compound 19) at a yield of 57%, MS m/z: 1020 [M+Na]$^+$.

Azidoacetic acid rapamycin ester (compound 19) (0.7 g, 0.7 mmoL) and triphenyl phosphine (0.37 g, 1.4 mmoL) were added to reaction bottle. Mixture of tetrahydrofuran and water (5:1, 180 mL) was added and the system was heated to 50° C. to react overnight. After the reaction solution was concentrated, the residues were extracted by ethyl acetate, and the extract solution was washed by saturated saline and dried. After concentrated under reduced pressure, the residues were purified by column chromatography to produce glycine rapamycin ester (compound 20) 0.48 g, with a yield of 70%, MS m/z: 994 [M+Na]$^+$.

Methoxy PEG acetic acid (20K, 1 g, 0.05mmoL), glycine rapamycin ester (compound 20) (97 mg, 0.1 mmoL), 1-hydroxybenzotrizole (HOBt, 6.8 mg, 0.05 mmoL) and DMAP (12.2 mg, 0.1 mmoL) were added to reaction bottle, and dichloromethane was used to dissolve them, and the system was cooled in ice bath. The dichloromethane solution containing DCC (15.5 mg, 0.075 mmoL) was dropped into the system. After the drop, the system was warmed to room temperature naturally to react overnight. In the next day, the reaction solution was concentrated and the residues were recrystallized by the isopropanol to produce 0.82 g conjugate of methoxy PEG acetic acid glycine (number-average molecular weight of 20,000)-rapamycin (LPR-1).

$^1$H-NMR (300 MHz, CDCl$_3$): 0.90 (Me, 3H), 0.92 (Me, 3H), 0.94 (Me, 3H), 0.96 (Me, 3H), 0.97 (Me, 3H), 1.10 (CH$_2$, 2H), 1.11 (CH$_2$, 2H), 1.20 (CH$_2$, 2H), 1.33 (CH$_2$, 2H), 1.37 (CH, 1H), 1.45 (CH$_2$, 2H), 1.47 (CH$_2$, 2H), 1.60 (CH$_2$, 2H), 1.61 (CH$_2$, 2H), 1.65 (CH$_2$, 2H), 1.65 (CH$_2$, 2H), 1.74 (Me, 3H), 1.75 (CH, 1H), 2.07 (CH, 4H), 2.08 (CH$_2$, 2H), 3.14 (Me, 3H), 3.33 (CH, 1H), 3.36 (Me, 3H), 3.37 (CH$_2$, 2H), 3.42 (CH, 1H), 3.44 (Me, 3H), 3.56 (CH, 1H), 3.64 (CH$_2$, 1800H), 3.71 (CH, 1H), 3.72 (CH, 1H), 3.86 (CH, 1H), 4.17 (CH$_2$, 2H), 4.19 (CH, 1H), 5.16 (CH, 1H), 5.17 (CH, 1H), 5.29(=CH, 1H), 5.39(=CH, 1H), 5.95(=CH, 1H), 6.13(=CH, 1H), 6.31(=CH, 1H), 6.38(=CH, 1H), 8.34 (CH, 1H).

EXAMPLE 11

Preparation of the Conjugate of Methoxy PEG Dipeptide of Glutamic Acid and Glycine (Number-Average Molecular Weight of 20,000)-Rapamycin (LPR-2)

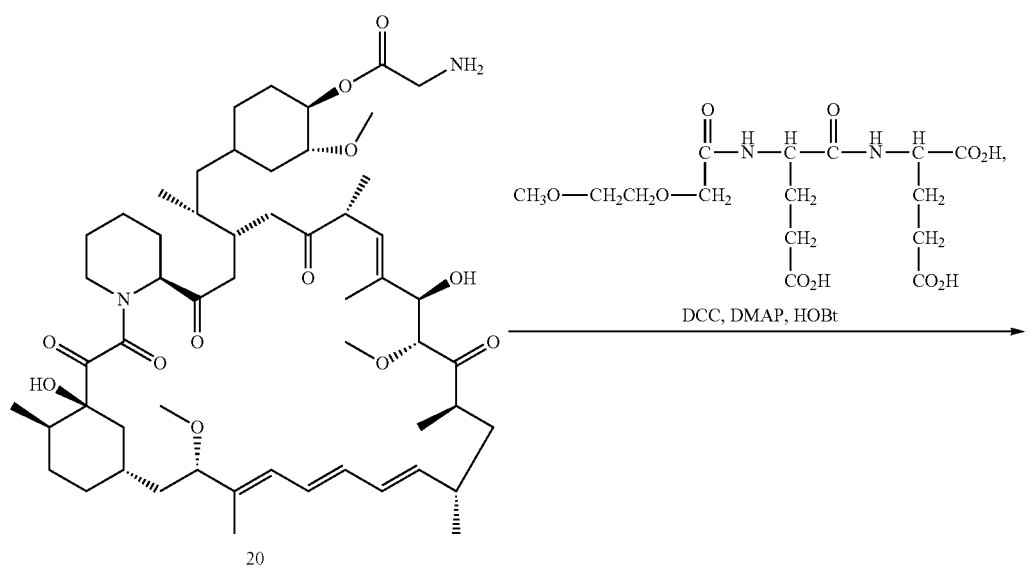

20

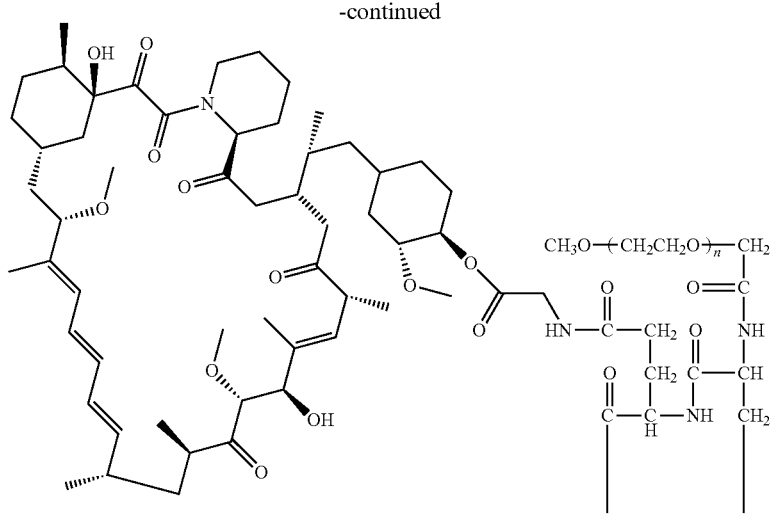

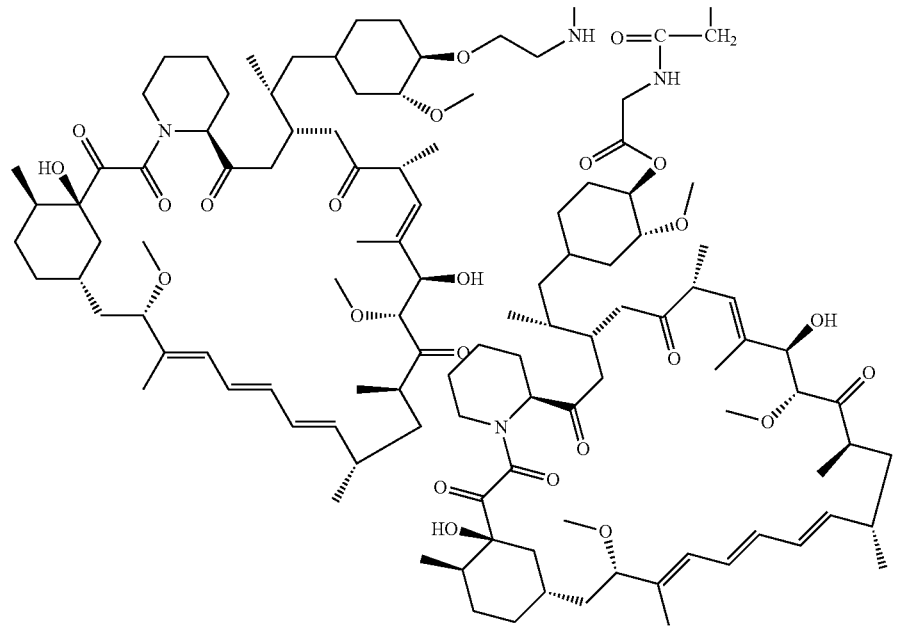

LPR-2

Methoxy PEG dipeptide acid of glutamic acid (compound 5) was prepared according to the method in the Example 1.

Methoxy PEG dipeptide acid of glutamic acid (compound 5) (20K, 0.5 g, 0.025 mmol), 48.6 mg (0.05 mmol) glycine rapamycin ester (compound 20), HOBt (3.4 mg, 0.025mmoL) and 6.1 mg (0.05mmoL) DMAP were added to the reaction bottle, and dichloromethane was used to dissolve them, and the system was cooled in ice bath. The dichloromethane solution containing 15.5 mg (0.075 mmol) DCC was then dropped into the system. After the drop, the system was naturally warmed to room temperature to react overnight. In the next day, the reaction solution was concentrated and the residues were recrystallized by the isopropanol to produce 0.41 g conjugate of methoxy PEG (20K) dipeptide of glutamic acid glycine-rapamycin (LPR-2).

$^1$H-NMR (300 MHz, CDCl$_3$): 0.90 (Me, 9H), 0.92 (Me, 9H), 0.94 (Me, 9H), 0.96 (Me, 9H), 0.97 (Me, 9H), 1.10 (CH$_2$, 6H), 1.11 (CH$_2$, 6H), 1.20 (CH$_2$, 6H), 1.33 (CH$_2$, 6H), 1.37 (CH, 3H), 1.45 (CH$_2$, 6H), 1.47 (CH$_2$, 6H), 1.60 (CH$_2$, 6H), 1.61 (CH$_2$, 6H), 1.65 (CH$_2$, 6H), 1.65 (CH$_2$, 6H), 1.74 (Me, 9H), 1.75 (CH, 3H), 2.07 (CH, 12H), 2.08 (CH$_2$, 6H), 3.14 (Me, 9H), 3.33 (CH, 3H), 3.36 (Me, 9H), 3.37 (CH$_2$, 6H), 3.42 (CH, 3H), 3.44 (Me, 9H), 3.56 (CH, 3H), 3.64 (CH$_2$, 1800H), 3.71 (CH, 3H), 3.72 (CH, 3H), 3.86 (CH, 3H), 4.17 (CH$_2$, 6H), 4.19 (CH, 3H), 5.16 (CH, 3H), 5.17 (CH, 3H), 5.29(=CH, 3H), 5.39(=CH, 3H), 5.95(=CH, 3H), 6.13(=CH, 3H), 6.31(=CH, 3H), 6.38(=CH, 3H), 8.34 (CH, 3H).

EXAMPLE 12
Preparation of the Conjugate of Y Shape PEG Dipeptide of Glutamic Acid and Glycine (Number-Average Molecular Weight of 40,000)-Rapamycin (LPR-3)
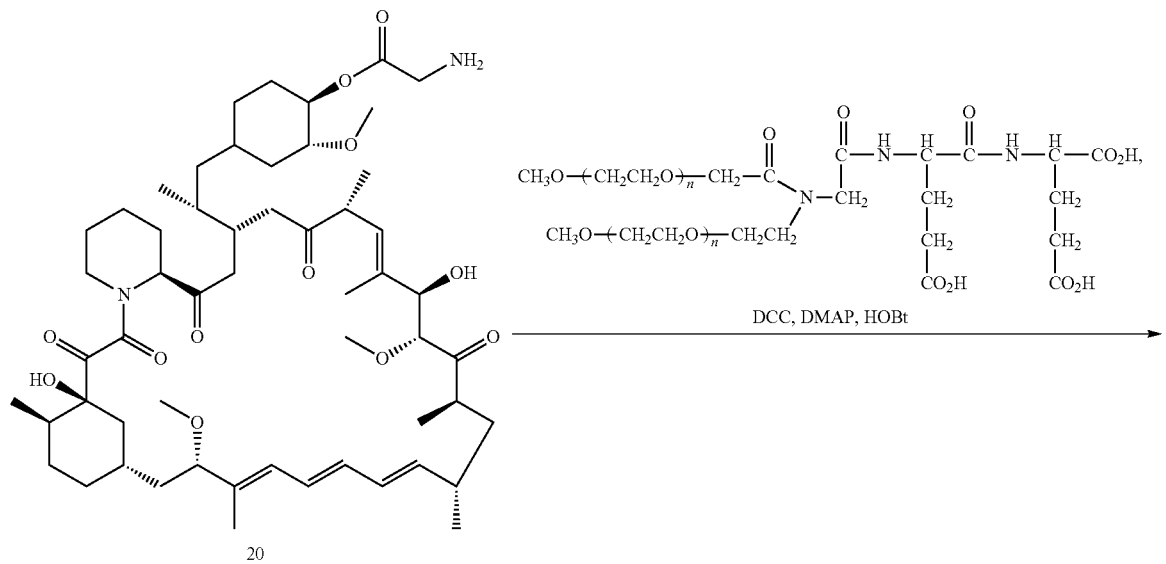
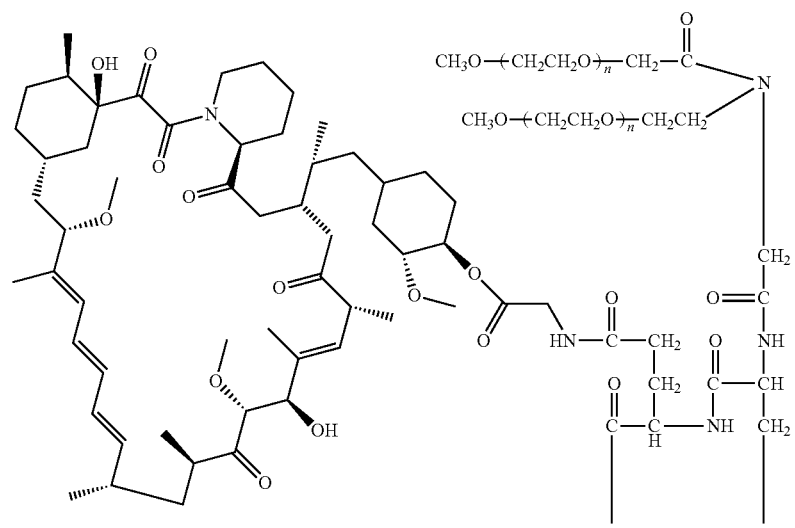

-continued

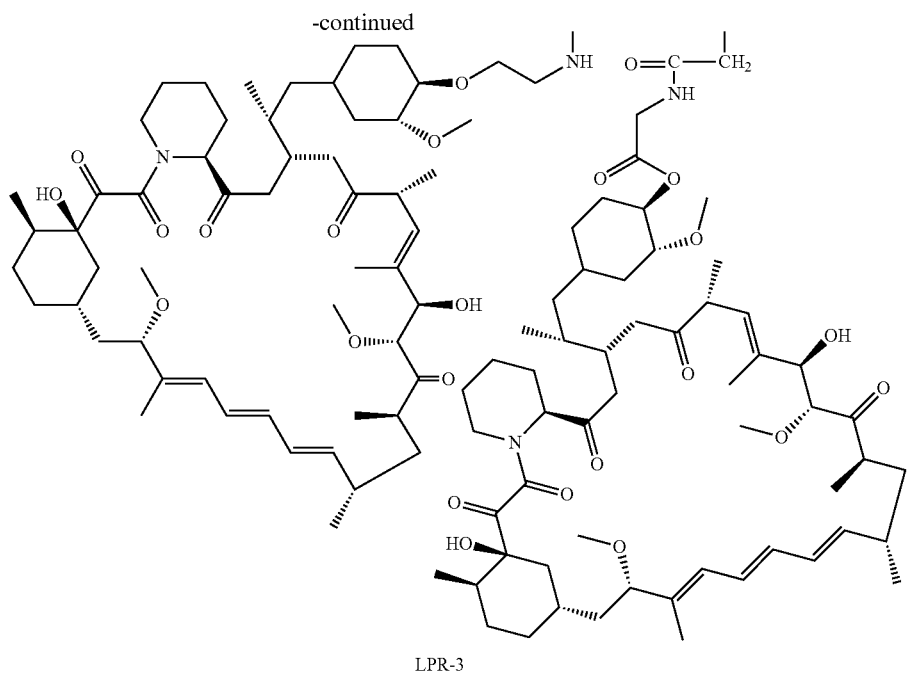

LPR-3

Y shape PEG dipeptide acid of glutamic acid (compound 13) was prepared according to the method in above-mentioned Examples.

Y shape PEG dipeptide acid of glutamic acid (compound 13) (40K, 0.5 g, 0.0125 mmol), 24.3 mg (0.025 mmol) glycine rapamycin ester (compound 20), HOBt (1.7 mg, 0.0125 mmol) and 3 mg (0.025 mmol) DMAP were added to the reaction bottle, and the dichloromethane was used to dissolve them, and the system was cooled in ice bath. 20 mL dichloromethane solution containing 4.1 mg (0.02 mmol) DCC was then dropped into the system. After the drop, the system was naturally warmed to room temperature to react overnight. In the next day, the reaction solution was concentrated and the residues were recrystallized by the isopropanol to produce 0.44 g conjugate of Y shape PEG dipeptide of glutamic acid and glycine (number-average molecular weight of 40,000)-rapamycin (LPR-3).

$^1$H-NMR (300 MHz, CDCl$_3$): 0.90 (Me, 9H), 0.92 (Me, 9H), 0.94 (Me, 9H), 0.96 (Me, 9H), 0.97 (Me, 9H), 1.10 (CH$_2$, 6H), 1.11 (CH$_2$, 6H), 1.20 (CH$_2$, 6H), 1.33 (CH$_2$, 6H), 1.37 (CH, 3H), 1.45 (CH$_2$, 6H), 1.47 (CH$_2$, 6H), 1.60 (CH$_2$, 6H), 1.61 (CH$_2$, 6H), 1.65 (CH$_2$, 6H), 1.65 (CH$_2$, 6H), 1.74 (Me, 9H), 1.75 (CH, 3H), 2.07 (CH, 12H), 2.08 (CH$_2$, 6H), 3.14 (Me, 9H), 3.33 (CH, 3H), 3.36 (Me, 9H), 3.37 (CH$_2$, 6H), 3.42 (CH, 3H), 3.44 (Me, 9H), 3.56 (CH, 3H), 3.64 (CH$_2$, 1800H), 3.71 (CH, 3H), 3.72 (CH, 3H), 3.86 (CH, 3H), 4.17 (CH$_2$, 6H), 4.19 (CH, 3H), 5.16 (CH, 3H), 5.17 (CH, 3H), 5.29(=CH, 3H), 5.39(=CH, 3H), 5.95(=CH, 3H), 6.13(=CH, 3H), 6.31(=CH, 3H), 6.38(=CH, 3H), 8.34 (CH, 3H).

EXAMPLE 13

Inhibitory Activities of Different Conjugates of PEG Rapamycin on Tumor Cells (1) Experiment Methods and Steps:
(a) Cell Culture
Plc/prf/5 cells were cultured in vitro in monolayer under conditions of MEM medium with supplement of 10% heat-inactivated fetal calf serum at 37° C. in an incubator at an atmosphere with 5% CO$_2$. The cells were digested by using tyrisin-EDTA and passaged twice a week. Cells in exponential growth phase were collected, counted and used to inoculate.

(b) tumor cell inoculation, grouping and administration $1\times10^7$ plc/prf/5 tumor cells were suspended in 0.1 mL mixture (PBS: Matrigel=4:1), and were inoculated to the right scapula on the back of each NOD/SCID mouse. When the average tumor volume reached about 350 mm$^3$ at 24th days after the inoculation, the mice with undersized or oversized tumor volume were removed and the other mice were divided to groups randomly according to the tumor volume and then were administrated.

(c) Experiment Scheme

TABLE 5

Grouping and administration to the animals in the experiment

| Group | N | Compound treatment | Dose$^a$ (mg/kg) | Administration volume (μl/g) | Administration route | Administration scheme |
|---|---|---|---|---|---|---|
| 1 | 5 | Solvent control | — | 10 | i.v. | Q2W × 2W |
| 2 | 5 | LPR-1 | 10 mg/kg | 10 | i.v. | Q2W × 2W |
| 3 | 5 | LPR-2 | 10 mg/kg | 10 | i.v. | Q2W × 2W |
| 4 | 5 | LPR-3 | 10 mg/kg | 10 | i.v. | Q2W × 2W |

Figure 2:
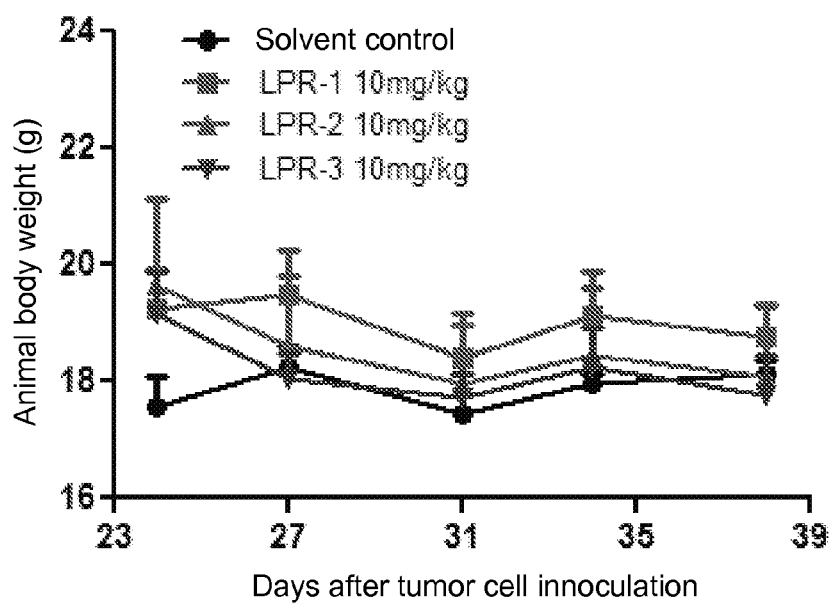
FIG. 2 shows body weight changes of tumor-bearing mice of human liver cancer plc/prf/5 caused by LPR-1, LPR-2, LPR-3 and solvent.

$^a$Administration amount was calculated based on rapamycin (2) Experiment Results
(a) Body Weight
The body weight changes of tumor-bearing mice of each treatment group were shown in Table 6 and FIG. 2.

TABLE 6

Body weight of each treatment group at different time points

| Days after the inoculation | Animal body weight (g) [a] | | | |
|---|---|---|---|---|
| | Solvent control | LPR-1 10 mg/kg | LPR-2 10 mg/kg | LPR-3 10 mg/kg |
| 24 | 17.6 ± 0.5 | 19.2 ± 0.7 | 19.6 ± 1.5 | 19.2 ± 0.7 |
| 27 | 18.3 ± 0.3 | 19.5 ± 0.8 | 18.6 ± 1.2 | 18.0 ± 0.4 |
| 31 | 17.4 ± 0.1 | 18.4 ± 0.6 | 18.0 ± 1.2 | 17.7 ± 0.4 |
| 34 | 18.0 ± 0.2 | 19.1 ± 0.8 | 18.5 ± 1.2 | 18.2 ± 0.7 |
| 38 | 18.1 ± 0.2 | 18.8 ± 0.5 | 18.1 ± 1.2 | 17.8 ± 0.7 |

Note:
[a] average ± standard error (b) Tumor Volume

Figure 3:
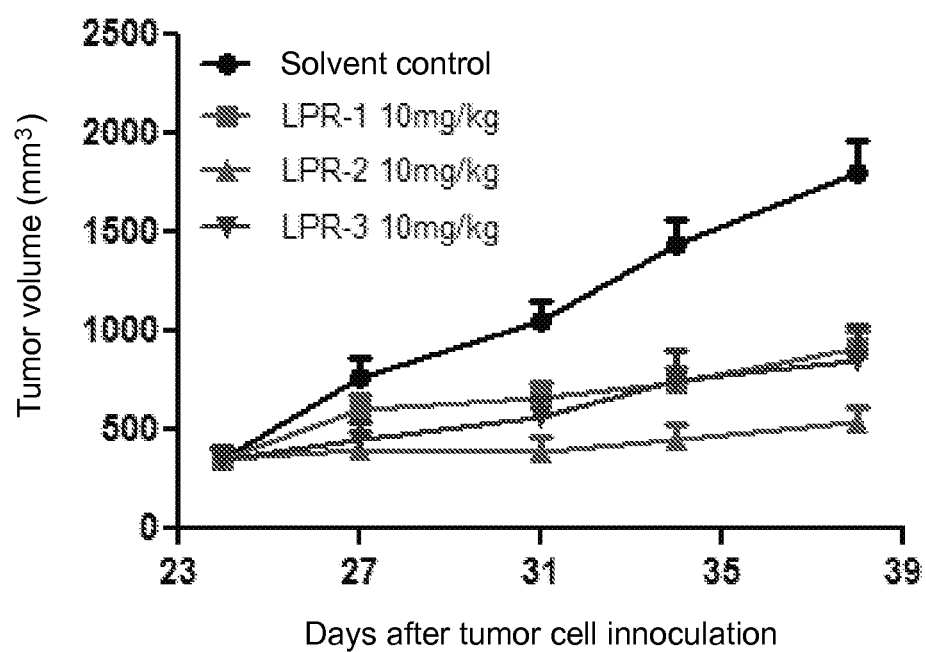
FIG. 3 shows the anti-cancer activity of LPR-1, LPR-2, LPR-3 and the solvent on the subcutaneously transplanted tumor model of human liver cancer plc/prf/5.

The tumor volume changes of each treatment group were shown in Table 7 and FIG. 3.

TABLE 7

Tumor volume of each treatment group at different time points

| Days after the inoculation | Tumor volume (mm³)[a] | | | |
|---|---|---|---|---|
| | Solvent control | LPR-1 10 mg/kg | LPR-2 10 mg/kg | LPR-3 10 mg/kg |
| 24 | 355 ± 64 | 352 ± 49 | 353 ± 54 | 358 ± 62 |
| 27 | 763 ± 102 | 598 ± 80 | 404 ± 89 | 455 ± 85 |
| 31 | 1048 ± 104 | 670 ± 74 | 391 ± 72 | 569 ± 100 |
| 34 | 1439 ± 130 | 738 ± 74 | 456 ± 77 | 754 ± 151 |
| 38 | 1801 ± 162 | 919 ± 78 | 536 ± 77 | 848 ± 178 |

Note:
[a] average ± standard error (c) Evaluation Index of Anti-Tumor Effect

The evaluation index on anti-tumor effect of LPR1, 2, 3 to the plc/prf/5 subcutaneously xenografted tumor model was shown in Table 8.

TABLE 8

Evaluation on the effect of the anti-tumor drugs in each treatment group

| Group | Tumor volume (mm³)[a] | Tumor proliferation rates T/C (%) | Delayed days of tumor growth (to 1000 mm³) | P value |
|---|---|---|---|---|
| Solvent control | 1801 ± 162 | — | — | — |
| LPR-1 | 919 ± 78 | 51 | 7 | 0.000 |
| LPR-2 | 536 ± 77 | 30 | >7 | 0.000 |
| LPR-3 | 848 ± 178 | 47 | >7 | 0.000 |

Note:
[a] average ± standard error (3) Conclusion on the Experiment Results and Discussion During the present experiment, the in vivo effect of LPR-1, LPR-2 and LPR-3 on human liver cancer plc/prf/5 subcutaneously xenografted tumor model was evaluated. The tumor volumes of each treatment group at different time points were shown in Table 2. As it can be seen in FIG. 2, at 38th day after the Plc/prf/5 tumor cells inoculation to the NOD/SCID mouse, the tumor volume of solvent control group reached 1,801 mm³. The tested drugs LPR-1, LPR-2 and LPR-3 all exhibited inhibitory effects to some extent, wherein the anti-tumor effect of LPR-2 was most remarkable and its T/C was less than 40% compared with the solvent group, and p value is 0.000, which has significant difference.

The body weight changes of tumor-bearing mice for each group were shown in Table 6 and FIG. 2. Toxicity response was not observed in each treatment group during the experiment.

In conclusion, the tested drugs LPR-1, LPR-2 and LPR-3 exhibited anti-tumor effect on human liver cancer plc/prf/5 subcutaneously xenografted tumor model in the experiment, wherein the anti-tumor effect of LPR-2 was most remarkable. Toxicity response was not observed in each treatment group during the experiment. PEG that was used for LPR-1 has the same structure and the same average molecular weight with the one for LPR-2. The difference between them was that PEG of LPR-1 was bonded with the rapamycin through glycine only. The PEG molecule can bind with one rapamycin molecule only at one end; whereas, PEG of LPR-2 was bonded with the rapamycin through the dipeptide of glutamic acid and glycine. The PEG molecule can bind with three rapamycin molecules at one end. The drug load ratio of LPR-2 was three times of LPR-1 and thus the anti-tumor effects thereof was much higher than LPR-1.

EXAMPLE

Conjugates of Irinotecan

The irinotecan hydrochloride used in the present example was purchased from Knowshine (Shanghai) Pharmachemicals Inc.

EXAMPLE 14

Preparation of the Conjugate of Methoxy PEG Dipeptide of Glutamic Acid and Glycine (Number-Average Molecular Weight of 20,000)-Irinotecan (YNR-1)

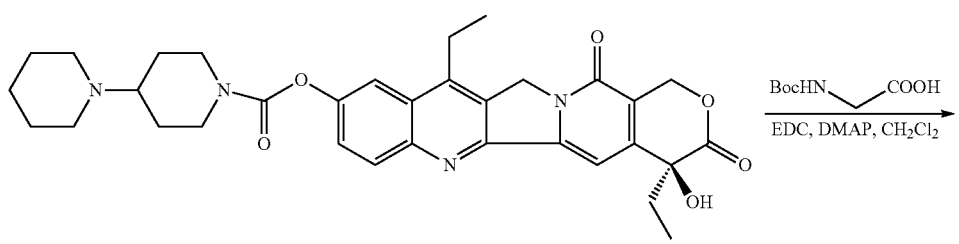

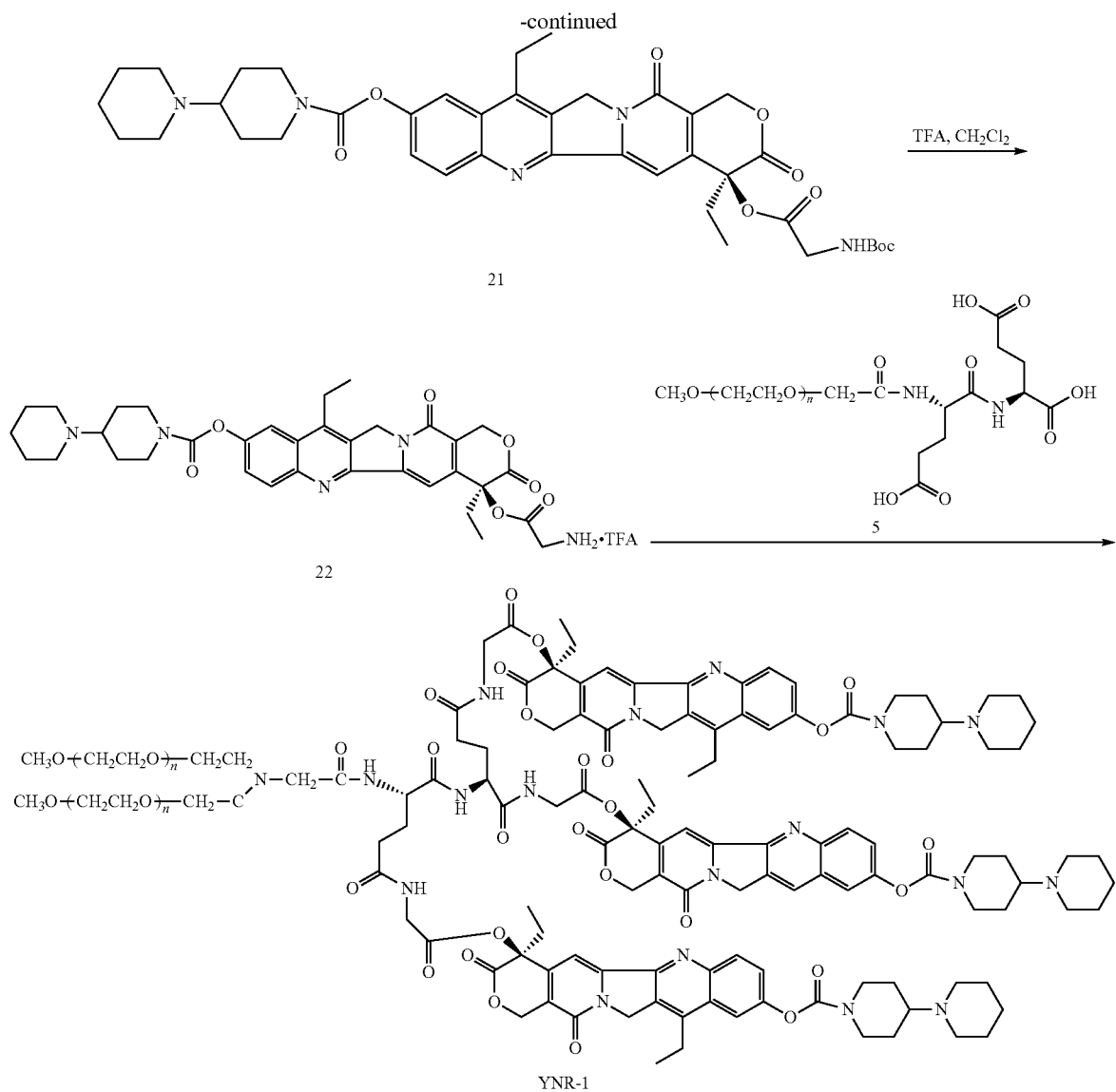

13.3 g irinotecan hydrochloride and 20.1 g N-tert-butyloxycarbonyl glycine were dissolved in 120 mL anhydrous dichloromethane, and 18.8 g dicyclohexylcarbodiimide (DCC) and 7.4 g 4-dimethylaminopyridine (DMAP) were added and the system was stirred at room temperature overnight. The solid formed during the reaction was removed by filtration, and the solution was concentrated under reduced pressure, and 100 mL petroleum ether was added. The precipitation was collected by filtration and dried under vacuum to produce 23 g N-tert-butyloxycarbonyl glycine irinotecan ester (compound 21).

23 g N-tert-butyloxycarbonyl glycine irinotecan ester (compound 21) was dissolved in 100 mL dichloromethane, and 30 mL trifluoroacetic acid was added and the system was stirred at room temperature for 5 h. The solution was concentrated under reduced pressure, and 500 mL ether was added. The system was filtered and the precipitation was collected and dried under vacuum to produce 20 g glycine irinotecan ester (compound 22).

Methoxy PEG dipeptide acid of glutamic acid (compound 5) was prepared according to the method in the Example 1.

5.0 g Methoxy PEG dipeptide acid of glutamic acid (compound 5) (molecular weight of 20,000), 1.02 g glycine irinotecan ester (compound 22), 115 mg N-hydroxysuccinimide (NHS), and 153 mg 4-dimethylaminopyridine (DMAP) were dissolved in 50 mL anhydrous dichloromethane, and 309 mg dicyclohexylcarbodiimide (DCC) was further added under the protection of the nitrogen gas. The system was stirred and reacted at room temperature overnight. The solid substance was removed by filtration, and other solvent was removed by rotary evaporation. 100 mL isopropanol (IPA) was added to the residues, which was filtered and the product was dried in vacuum to produce 4.4 g conjugate of methoxy PEG dipeptide of glutamic acid and glycine (number-average molecular weight of 20,000)-irinotecan (YNR-1). $^1$H-NMR (DMSO-d6): 0.84-0.89(m, 8H), 1.24(m, 9H), 1.40-1.50(m, 21H), 1.79(m, 8H), 2.12(m, 10H), 2.89(m, 4H), 3.50(m, 1800H), 4.05(m, 9H), 4.26(m, 5H), 5.26(m, 5H), 5.48(m, 5H), 7.07(m, 2H), 7.55-7.60(m, 3H), 7.89(m, 3H), 8.11(m, 4H), 8.20(m, 3H).

EXAMPLE 15

Preparation of the Conjugate of Y Shape PEG Dipeptide of Glutamic Acid and Glycine (Number-Average Molecular Weight of 40,000)-Irinotecan (YNR-2)

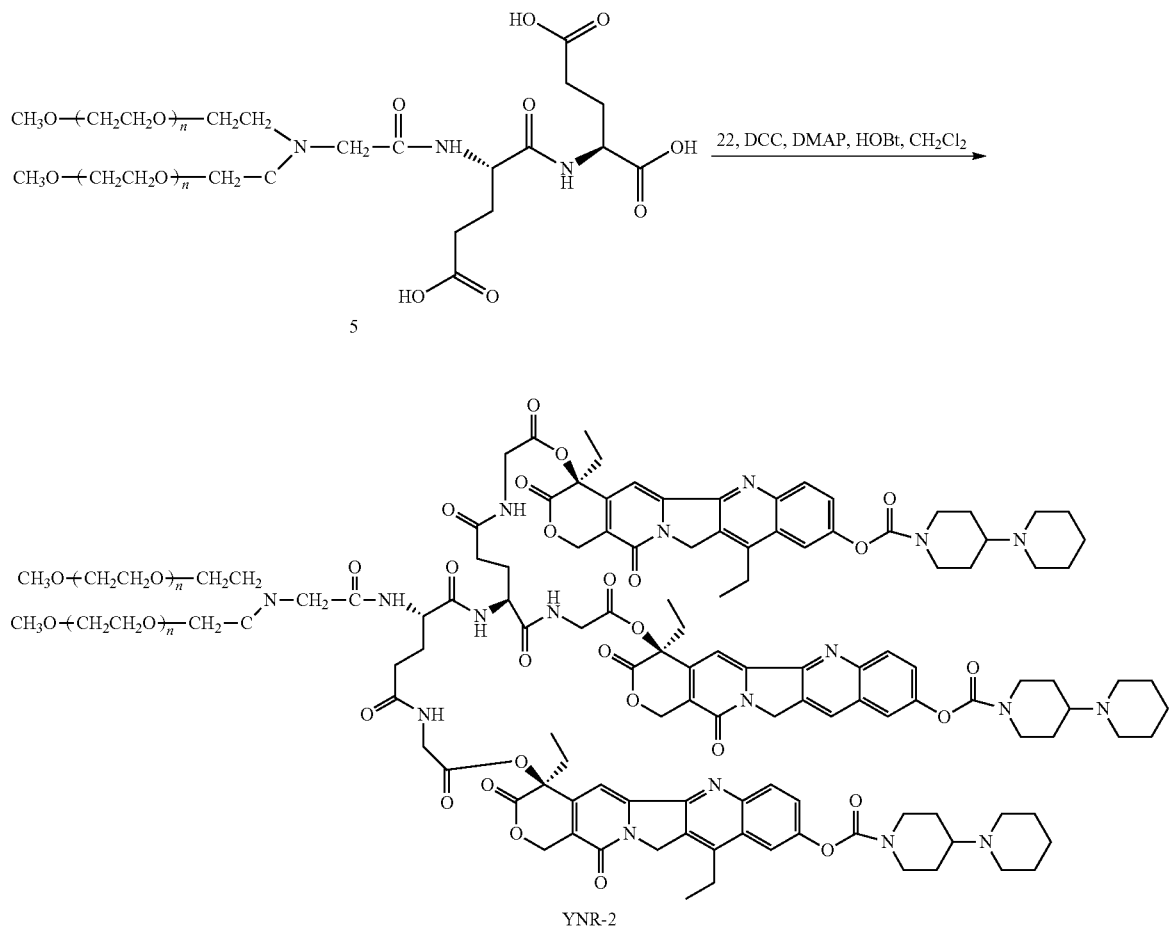

YNR-2

Y shape PEG dipeptide acid of glutamic acid (compound 13) (molecular weight of 40,000) was prepared according to the method in abovementioned examples. 10 g Y shape PEG dipeptide acid of glutamic acid (compound 13) (molecular weight of 40000), 1.02 g glycine irinotecan ester (compound 22), 115 mg N-hydroxysuccinimide (NHS), 153 mg 4-dimethylaminopyridine (DMAP) were dissolved in 50 mL anhydrous dichloromethane, and 309 mg dicyclohexylcarbodiimide (DCC) was further added under the protection of the nitrogen gas. The system was stirred and reacted at room temperature overnight. The solid substance was removed by filtration, and other solvent was removed by rotary evaporation. 100 mL isopropanol (IPA) was added to the residues, which was filtered and the product was dried in vacuum to produce 9.4 g conjugate of Y shape PEG dipeptide of glutamic acid and glycine (molecular weight of 40,000)-irinotecan (YNR-2). $^1$H-NMR (DMSO-$d_6$): 0.82(m, 9H), 1.23(m, 11H), 1.40-1.50(m, 20H), 1.79(m, 8H), 2.12(m, 10H), 3.50(m, 3600H), 3.98-4.22(m, 20H), 5.26-5.48(m, 8H), 7.07(m, 2H), 7.80(m, 2H), 7.90(m, 3H), 8.11(m, 4H), 8.20(m, 2H).

EXAMPLE 16

Preparation of the Conjugate of Methoxy PEG Tripeptide of Glutamic Acid and Glycine (Number-Average Molecular Weight of 20,000)-Irinotecan (YNR-3)

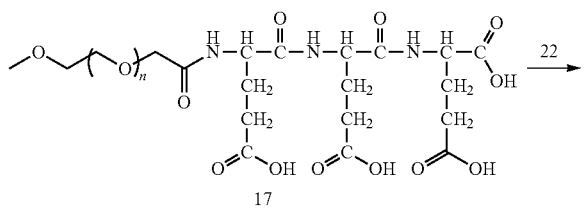

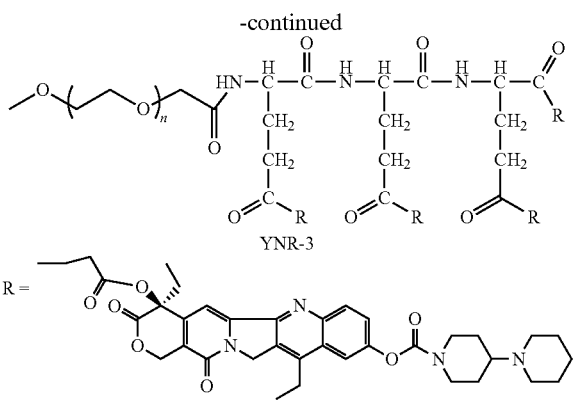

YNR-3

Methoxy PEG tripeptide acid of glutamic acid (compound 17) (molecular weight of 20,000) was prepared according to the method in abovementioned examples. 5.0 g Methoxy PEG tripeptide acid of glutamic acid (compound 17) (molecular weight of 20,000), 1.36 g irinotecan glycine ester (compound 22), 115 mg N-hydroxysuccinimide (NHS), and 153 mg 4-dimethylaminopyridine (DMAP) were dissolved in 50 mL anhydrous dichloromethane, and 309 mg dicyclohexylcarbodiimide (DCC) was further added under the protection of the nitrogen gas. The system was stirred and reacted at room temperature overnight. The solid substance was removed by filtration, and other solvent was removed by rotary evaporation. 100 mL isopropanol (IPA) was added to the residues which was filtered and the product was dried in vacuum to produce 4.5 g conjugate of methoxy PEG tripeptide of glutamic acid and glycine (number-average molecular weight of 20,000)-irinotecan (YNR-3). $^1$H-NMR (DMSO-d6): 0.84-0.89(m, 8H), 1.24(m, 9H), 1.71-1.74(m, 23H), 2.12(m, 16H), 2.95-2.99(m, 19H), 3.50(m, 1800H), 4.22(m, 18H), 5.45(m, 5H), 5.49(m, 5H), 7.07(m, 2H), 7.55-7.60(m, 3H), 7.89(m, 3H), 8.11(m, 4H), 8.20(m, 3H).

EXAMPLE 17

Inhibitory Effects of the Conjugate of PEG Irinotecan on Growth of Xenografted Tumor of Human Colon Cancer in HCT-116 Nude Mice The drug to be tested YNR-1 was the conjugate of methoxy PEG acetic acid glycine-irinotecan.

The positive control drug, irinotecan hydrochloride injection solution (CPT-11) (40 mg/2 mL) with batch number 8UL002-B was produced by Aventis Pharma (Dagenham) incorporation. It was diluted with normal saline to the desired concentration before use.

Setting on Dose

YNR-1 dose was set to be 45 mg/kg (calculated based on the amount of irinotecan contained), and was administrated by intravenous injection once a week for three weeks; CPT-11 dose was 45 mg/kg which was administrated once a week by intravenous injection, and 15 mg/kg which was administrated by intravenous injection three times a week for three weeks.

Animal: BALB/cA male nude mice, 5-6 weeks old with body weight of 19±2 g, were provided by Shanghai Institute of Material Medical, Chinese Academy of Sciences, No. of certificate for compliance of production: SCXK (Shanghai) 2008-0017. The animal number for each group is as follows: 12 mice for the negative control group and 6 mice for the treatment groups.

Cell Line

Human colon cancer HCT-116 cell line which was purchased from ATCC was subcutaneously inoculated to the right armpit of the nude mice with inoculation cell amount of $5 \times 10^6$/mouse. After the xenografted tumor formed, it was passaged two times within the nude mice and then subject to use.

Experiment Method

Tumor tissue at vigorously growing stage was cut to about 1.5 mm$^3$. It was subcutaneously inoculated to the right armpit of nude mice under sterile conditions. The diameter of subcutaneously xenografted tumor of the nude mice was measured by the caliper. After the tumor grew to 100-200 mm$^3$, the animals were divided to groups randomly. YNR-1, the treatment group, was administrated at the does of 45 mg/kg. The control group was administrated normal saline at equal amount. They were administrated by intravenous injection once a week for three weeks. CPT-11 (15 mg/kg), the positive control drug, was administrated by intravenous injection three times a week for three weeks. After the administration, the animals were continuously monitored for one week. The diameter of xenografted tumor and mouse body weight were measured simultaneously twice a week during the whole experiment process. The calculation formula of tumor volume (TV) was as follows: TV=½×a×b$^2$, wherein a and b represent the length and the width, respectively. Relative tumor volume (RTV) was calculated based on the measured results through the following formula: RTV=Vt/V$_0$. V$_0$ was the tumor volume measured at the time of dividing cages for administration (i.e. d0), and Vt was the tumor volume at each measurement. The evaluation index of anti-tumor activity was relative tumor proliferation ratio T/C (%), whose calculation formula was as follows: T/C (%)= (T$_{RTV}$/C$_{RTV}$)×100%, T$_{RTV}$: RTV for treatment group; C$_{RTV}$: RTV for negative control group.

Result and Discussion

The experiment results were shown in Table 9. YNR-1 (45 mg/kg), which was administrated by intravenous injection once a week for three weeks has inhibited dramatically the growth of subcutaneously xenografted tumor of human colon cancer HCT-116 nude mice with T/C of 27.60%. Its anti-tumor effect was better than CPT-11 (45 mg/kg) at the same dose and administration scheme. CPT-11 with the same administration scheme also inhibited the growth of subcutaneously xenografted tumor of HCT-116, but the T/C percentage is only 63.56%. The positive control of CPT-11 (15 mg/kg) which was intravenously administrated once a week for three weeks remarkably inhibited the growth of HCT-116 subcutaneously xenografted tumor as well, with T/C value of 39.84%. The body weights of nude mice for all groups decreased during the whole experiment process. Compared with the solvent control, CPT-11 45 mg/kg group was slightly better with respect to the decrease of nude mice body weight.

TABLE 9

Treatment effects of PEGylation irinotecan on xenografted tumor of human colon cancer HCT-116 nude mice in the experiment

| Group | Dosing, administration method | | No. of animal | | Body weight (g) | | TV (mm³, mean ± SD) | | RTV (mean ± SD) | T/C (%) |
|---|---|---|---|---|---|---|---|---|---|---|
| | | | Beginning | End | Beginning | End | $d_0$ | $d_{28}$ | | |
| Solvent control | 0.4 ml/mouse qw × 3w | iv | 12 | 12 | 19.7 | 17.3 | 132 ± 32 | 804 ± 82 | 6.45 ± 1.83 | |
| CPT-11 | 15 mg/kg, q3w × 3w | iv | 6 | 6 | 19.1 | 16.6 | 129 ± 26 | 322 ± 37 | 2.57 ± 0.66** | 39.84 |
| CPT-11 | 45 mg/kg, qw × 3w | iv | 6 | 6 | 19.2 | 15.1 | 126 ± 25 | 512 ± 99 | 4.10 ± 0.73* | 63.56 |
| YNR-1 | 45 mg/kg, qw × 3w | iv | 6 | 6 | 18.8 | 16.8 | 132 ± 30 | 234 ± 54 | 1.78 ± 0.23**,## | 27.60 |

Note:
t test, vs solvent control group, *p < 0.01, **p < 0.001; vs CPT-11 45 mg/kg group, #p < 0.05, ##p < 0.001

EXAMPLE 18

Inhibitory Effects of the Conjugate of PEG Irinotecan on Growth of Xenografted Tumor of Human Colon Cancer HT-29 Nude Mice The drug to be tested YNR-1 was the conjugate of methoxy PEG dipeptide of glutamic acid and glycine-irinotecan.

The positive control drug, irinotecan hydrochloride injection solution (CPT-11) (40 mg/2 ml) with batch number 8UL002-B was produced by Aventis Pharma (Dagenham) Incorporation. It was diluted with normal saline to the desired concentration before use.

Setting on Dose

YNR-1 dose was set to be 45 mg/kg (calculated based on the amount of irinotecan contained), and was administered by intravenous injection once a week for three weeks; CPT-11 dose was 45 mg/kg, which was administered by intravenous injection once a week; and 15 mg/kg, which was administered by intravenous injection three times a week for three weeks.

Animals

BALB/cA male nude mice, 5-6 weeks old with body weight of 18±2 g, were provided by Shanghai Institute of Material Medical, Chinese Academy of Sciences, No. of certificate for compliance of production: SCXK (Shanghai) 2008-0017. The animal number for each group was as follows: 12 mice for negative control group; 6 mice for the treatment group.

Cell Line

Human colon cancer HT-29 cell line which was purchased from ATCC was subcutaneously inoculated to the right armpit of the nude mice with inoculation cell amount of 5×10⁶/mouse. After the xenografted tumor formed, it was passaged two times within the nude mice and then subject to use.

Experiment Method

Tumor tissue at vigorously growing stage was cut to about 1.5 mm³. It was subcutaneously inoculated to the right armpit of the nude mice under sterile conditions. The diameter of subcutaneously xenografted tumor of nude mice was measured by the caliper. After the tumor grew to 100-200 mm³, animals were divided to groups randomly. YNR-1 and CPT-11 was administrated at the does of 45 mg/kg. The control group was administrated normal saline at equal amount. They were administrated by intravenous injection once a week for three weeks. CPT-11 (15 mg/kg), the positive control drug, was administrated by intravenous injection three times a week for three weeks. After the administration, the animals were continuously monitored for one week. The diameter of xenografted tumor and mouse body weight were measured simultaneously twice a week during the whole experiment process. The calculation formula of tumor volume (TV) was as follows: $TV = \frac{1}{2} \times a \times b^2$, wherein a and b represent the length and the width, respectively. Relative tumor volume (RTV) was calculated based on the measured results through the following formula: $RTV = V_t/V_0$. $V_0$ was the tumor volume measured at the time of dividing cages for administration (i.e. $d_0$), and Vt was the tumor volume at each measurement. The evaluation index of anti-tumor activity was relative tumor proliferation ratio T/C (%), whose calculation formula was as follows: T/C (%) = $(T_{RTV}/C_{RTV}) \times 100\%$, $T_{RTV}$: RTV for treatment group; $C_{RTV}$: RTV for negative control group.

Results and Discussion

The experiment results were shown in Table 10. YNR-1 (45 mg/kg), which was administrated by intravenous injection once a week for three weeks inhibited dramatically the growth of subcutaneously xenografted tumor of human colon cancer HT-29 nude mice. After the administration for one week, the tumor volume increase of the mice in the treatment group slowed down. At the end of the experiment, the T/C percentage was 41.08%. The positive control CPT-11 (15 mg/kg) that was administrated three times a week for three weeks has remarkable inhibited the growth of HT-29 subcutaneously xenografted tumor as well, with the T/C value of 27.27%. The nude mice in each group grew well during the whole experiment process, and only the mice in two CPT-11 groups with different doses showed the body weight decrease.

TABLE 10

Treatment effects of PEGylation irinotecan on xenografted tumor of human colon cancer HT-29 nude mice in the experiment

| Group | Dosing, administration method | | No. of animal | | Body weight (g) | | TV (mm³, mean ± SD) | | RTV (mean ± SD) | T/C (%) |
|---|---|---|---|---|---|---|---|---|---|---|
| | | | Beginning | End | Beginning | End | $d_0$ | $d_{28}$ | | |
| Solvent control | 0.4 ml/mouse qw × 3w | iv | 12 | 12 | 19.0 | 19.2 | 119 ± 29 | 1588 ± 578 | 13.90 ± 5.38 | |
| CPT-11 | 15 mg/kg, q3w × 3w | iv | 6 | 6 | 18.2 | 16.0 | 121 ± 14 | 460 ± 152 | 3.79 ± 1.21*, | 27.27 |
| CPT-11 | 45 mg/kg, qw × 3w | iv | 6 | 6 | 18.6 | 16.2 | 116 ± 13 | 995 ± 368 | 8.69 ± 3.43*** | 62.52 |
| YNR-1 | 45 mg/kg, qw × 3w | iv | 6 | 6 | 18.7 | 18.4 | 115 ± 25 | 642 ± 105 | 5.71 ± 1.21** | 41.08 |

Note:
t test, vs solvent control group, *$p < 0.05$, $p < 0.01$, *$p < 0.001$; vs CPT-11 45 mg/kg group, #$p < 0.05$

EXPERIMENT 19

Inhibitory Effects of the Conjugate of PEG Irinotecan on Growth of Xenografted Tumor of Human Lung Cancer A549 Nude Mice The drug to be tested YNR-1 was the conjugate of methoxy PEG dipeptide of glutamic acid and glycine-irinotecan The positive control drug, irinotecan hydrochloride injection solution (CPT-11), 40 mg/2 ml with batch number 8UL002-B was produced by Aventis Pharma (Dagenham) incorporation. It was diluted with normal saline to the desired concentration before use.

Setting on Dose

YNR-1 dose was set to be 45 mg/kg (calculated based on the amount of irinotecan contained), and was administered by intravenous injection once a week for three weeks; CPT-11 dose was 45 mg/kg that was administrated by intravenous injection once a week; and 15 mg/kg that was administered by intravenous injection once a week for three weeks.

Animals

BALB/cA female nude mice, 5-6 weeks old with body weight of 18±2 g, were provided by Shanghai Institute of Material Medical, Chinese Academy of Sciences, No. of certificate for compliance of production: SCXK (Shanghai) 2008-0017. The animal number for each group was as follows: 12 mice for the negative control group; 6 mice the treatment group had.

Cell Line

Human lung cancer A549 cell line that was purchased from ATCC was subcutaneously inoculated to the right armpit of the nude mice with cell inoculation amount of 5×10⁶/mouse. After the xenografted tumor formed, it was passaged two times within the nude mice and then subject to use.

Experiment Method

Tumor tissue at vigorously growing stage was cut to about 1.5 mm³. It was subcutaneously inoculated to the right armpit of the nude mice under sterile conditions. The diameter of subcutaneously xenografted tumor of nude mice was measured by the caliper. After the tumor grew to 100-200 mm³, the animals were divided to groups randomly. YNR-1 and CPT-11 was administrated at the does of 45 mg/kg. The control group was administrated normal saline at equal amount. They were administrated by intravenous injection once a week for three weeks. CPT-11 (15 mg/kg), the positive control drug, was administrated by intravenous injection three times a week for three weeks. After the administration, the animals were continuously monitored for one week. The diameter of xenografted tumor and mouse body weight were measured simultaneously twice a week during the whole experiment process. The calculation formula of tumor volume (TV) was TV=½×a×b², wherein a and b represent the length and the width, respectively. Relative tumor volume (RTV) was calculated based on the measured results through the following formula: RTV=Vt/V₀. V₀ was the tumor volume measured at the time of dividing cages for administration (i.e. $d_0$), and Vt was the tumor volume at each measurement. The evaluation index of anti-tumor activity was relative tumor proliferation ratio T/C (%), whose calculation formula was as follows: T/C (%)= ($T_{RTV}$/$C_{RTV}$)×100%, $T_{RTV}$: RTV for treatment group; $C_{RTV}$: RTV for negative control group.

Results and Discussion

The experiment results were shown in Table 11. YNR-1 and CPT-11 (45 mg/kg) that was administrated by intravenous injection once a week for three weeks has inhibited dramatically the growth of subcutaneously xenografted tumor of human lung cancer A549 nude mice, with T/C of 20.62%. The anti-tumor effect of YNR-1 was significantly better than CPT-11 at the same dose and administration scheme. After YNR-1 treatment for one week, the growth of subcutaneously xenografted tumor of nude mice slowed down. The positive control, CPT-11 (15 mg/kg), that was intravenously administrated once a week for three weeks has remarkably inhibited the growth of A549 subcutaneously xenografted tumor as well, with T/C value of 53.26%. The nude mice in each treatment group grew well during the whole experiment process, and the body weight increase was slightly slower than that of the solvent control group.

TABLE 11

Treatment effects of PEGylation irinotecan on xenografted tumor of human lung cancer A549 nude mice in the experiment

| Group | Dosing, administration method | | No. of animal Beginning | No. of animal End | Body weight (g) Beginning | Body weight (g) End | TV (mm³, mean ± SD) $d_0$ | TV (mm³, mean ± SD) $d_{28}$ | RTV (mean ± SD) | T/C (%) |
|---|---|---|---|---|---|---|---|---|---|---|
| Solvent control | 0.4 ml/mouse qw × 3w | iv | 12 | 12 | 18.4 | 23.1 | 108 ± 21 | 1546 ± 496 | 14.40 ± 4.38 | |
| CPT-11 | 15 mg/kg, q3w × 3w | iv | 6 | 6 | 18.1 | 21.2 | 112 ± 21 | 831 ± 305 | 7.67 ± 2.88**, | 53.26 |
| CPT-11 | 45 mg/kg, qw × 3w | iv | 6 | 6 | 18.4 | 21.7 | 110 ± 15 | 1055 ± 432 | 9.87 ± 4.87 | 68.54 |
| YNR-1 | 45 mg/kg, qw × 3w | iv | 6 | 6 | 19.1 | 22.0 | 105 ± 21 | 320 ± 154 | 2.97 ± 1.04*,# | 20.62 |

Note:
t test, vs solvent control group, *p < 0.001, **p < 0.001; vs CPT-11 45 mg/kg group, #p < 0.01

EXAMPLE 20

Inhibitory Effects of the Conjugate of PEG Irinotecan on Growth of Xenografted Tumor of Human Ovarian Cancer SKOV-3 Nude Mice The drug to be tested YNR-1 was the conjugate of methoxy PEG dipeptide of glutamic acid and glycine-irinotecan The positive control drug, irinotecan hydrochloride injection solution (CPT-11) (40 mg/2 ml) with batch number 8UL002-B was produced by Aventis Pharma (Dagenham) Incorporation. It was diluted with normal saline to the desired concentration before use.

Setting on Dose

YNR-1 dose was set to be 45 mg/kg (calculated based on the amount of irinotecan contained), and was administered by intravenous injection once a week for three weeks; CPT-11 dose was 45 mg/kg which was administered by intravenous injection once a week, and 15 mg/kg which was administered by intravenous injection three times a week for three weeks.

Animals

BALB/cA female nude mice, 5-6 weeks old with body weight of 19±2 g, were provided by Shanghai Institute of Material Medical, Chinese Academy of Sciences, No. of certificate for compliance of production: SCXK (Shanghai) 2008-0017. The animal number for each group was as follows: 12 mice for the negative control group; 6 mice for the treatment group.

Cell Line

Human ovarian cancer SKOV-3 cell line that was purchased from ATCC was subcutaneously inoculated to the right armpit of the nude mice with cell inoculation amount of 5×10⁶/mouse. After the xenografted tumor formed, it was passaged two times within the nude mice and then subject to use.

Experiment Method

Tumor tissue at vigorously growing stage was cut to about 1.5 mm³. It was subcutaneously inoculated to the right armpit of the nude mice under sterile conditions. The diameter of subcutaneously xenografted tumor of nude mice was measured by the caliper. After the tumor grew to 100-200 mm³, animals were divided to groups randomly. YNR-1 and CPT-11 was administrated at the does of 45 mg/kg. The control group was administrated normal saline at equal amount. They were administrated by intravenous injection once a week for three weeks. CPT-11 (15 mg/kg), the positive control drug, was administrated by intravenous injection three times a week for three weeks. After the administration, the animals were continuously monitored for one week. The diameter of xenografted tumor and mouse body weight were measured simultaneously twice a week during the whole experiment process. The calculation formula of tumor volume (TV) was: TV=½×a×b², wherein a and b represent the length and the width, respectively. Relative tumor volume (RTV) was calculated based on the measured results through the following formula: RTV=Vt/$V_0$. $V_0$ was the tumor volume measured at the time of dividing cages for administration (i.e. $d_0$), and Vt was the tumor volume at each measurement. The evaluation index of anti-tumor activity was relative tumor proliferation ratio T/C (%), whose calculation formula was as follows: T/C (%)= ($T_{RTV}/C_{RTV}$)×100%, $T_{RTV}$: RTV for treatment group; $C_{RTV}$: RTV for negative control group.

Results and Discussion

The experiment results were shown in Table 12. YNR-1 that was administrated by intravenous injection once a week for three weeks has inhibited dramatically the growth of subcutaneously xenografted tumor of human ovarian cancer SKOV-3 nude mice, with T/C of 0.53%. The anti-tumor effect of YNR-1 was significantly better than CPT-11 at the same dose and administration scheme. The T/C percentage of CPT-11 in the same condition is 96.46%. One week after the administration of YNR-1, the tumor volume of each tumor-bearing mouse decreased and at the end of the experiment, the tumors of 4 tumor-bearing mice in YNR-1 group vanished completely. The positive control, CPT-11 (15 mg/kg) which was intravenously administrated once a week for three weeks has remarkably inhibited the growth of SKOV-3 subcutaneously xenografted tumor as well, with T/C value of 55.69%. The body weights of nude mice in the solvent control group and the two treatment groups with different CPT-11 all slightly decreased during the whole experiment process. However, the nude mice in YNR-1 treatment group grew well with body weights increased.

TABLE 12

Treatment effects of PEGylation irinotecan on xenografted tumor of human ovarian cancer SKOV-3 nude mice in the experiment

| Group | Dosing, administration method | | No. of animal Beginning | No. of animal End | Body weight (g) Beginning | Body weight (g) End | TV (mm³, mean ± SD) $d_0$ | TV (mm³, mean ± SD) $d_{28}$ | RTV (mean ± SD) | T/C (%) |
|---|---|---|---|---|---|---|---|---|---|---|
| Solvent control | 0.4 ml/mouse qw × 3w | iv | 12 | 12 | 19.8 | 18.7 | 136 ± 28 | 1770 ± 588(0) | 13.27 ± 4.75 | |
| CPT-11 | 15 mg/kg, q3w × 3w | iv | 6 | 6 | 18.9 | 18.0 | 137 ± 33 | 924 ± 443(0) | 7.39 ± 5.22**, | 55.69 |
| CPT-11 | 45 mg/kg, qw × 3w | iv | 6 | 6 | 19.7 | 18.4 | 136 ± 44 | 1753 ± 878(0) | 12.80 ± 3.91 | 96.46 |
| YNR-1 | 45 mg/kg, qw × 3w | iv | 6 | 6 | 20.7 | 22.7 | 135 ± 35 | 1.27 ± 1.98(4) | 0.07 ± 0.01*,# | 0.53 |

Note:
t test, vs solvent control group, *p < 0.001; vs CPT-11 45 mg/kg group, #p < 0.001, "( )" was the number of animals with vanished tumor

EXAMPLE 21

Inhibitory Effects of Irinotecan at Different Doses on Growth of Xenografted Tumor of Human Colon Cancer SW-620 Nude Mice The drug to be tested, YNR-1 was the conjugate of methoxy PEG dipeptide of glutamic acid and glycine-irinotecan.

The positive control drug, irinotecan hydrochloride injection solution (CPT-11) (40 mg/2 mL) with batch number 8UL002-B was produced by Aventis Pharma (Dagenham) Incorporation. It was diluted with normal saline to the desired concentration before use.

Setting on Dose

YNR-1 dose was set to be 45 mg/kg (calculated based on the amount of irinotecan contained), and was administered by intravenous injection once a week for three weeks; CPT-11 dose was 45 mg/kg which was administered by intravenous injection once a week, and 15 mg/kg which was administered by intravenous injection three times a week for three weeks.

Animals

BALB/cA male nude mice, 4-6 weeks old with body weight of 19±2 g, were provided by Shanghai Institute of Material Medical, Chinese Academy of Sciences, No. of certificate for compliance of production: SCXK (Shanghai) 2008-0017. The animal number for each group was as follows: 12 mice for the negative control group; 6 mice for the treatment group.

Cell Line

Human colon cancer SW-620 that was purchased from ATCC was subcutaneously inoculated to the right armpit of the nude mice with cell inoculation amount of $5 \times 10^6$/mouse. After the xenografted tumor formed, it was passaged two times within the nude mice and then subject to use.

Experiment Method

Tumor tissue at vigorously growing stage was cut to about 1.5 mm³. It was subcutaneously inoculated to the right armpit of nude mice under sterile conditions. The diameter of subcutaneously xenografted tumor of nude mice was measured by the caliper. After the tumor grew to 100-200 mm³, animals were divided to groups randomly. YNR-1 and CPT-11 was administered at the does of 45 mg/kg. The control group was administrated normal saline at equal amount. They were administrated by intravenous injection once a week for three weeks. CPT-11 (15 mg/kg), the positive control drug, was administrated by intravenous injection three times a week for three weeks. After the administration, the animals were continuously monitored for one week. The diameter of xenografted tumor and mouse body weight were measured simultaneously twice a week during the whole experiment process. The calculation formula of tumor volume (TV) was: TV=½×a×b², wherein a and b represent the length and the width, respectively. Relative tumor volume (RTV) was calculated based on the measured results through the following formula: RTV=Vt/$V_0$. $V_0$ was the tumor volume measured at the time of dividing cages for administration (i.e. $d_0$), and Vt was the tumor volume at each measurement. The evaluation index of anti-tumor activity was relative tumor proliferation ratio T/C (%), whose calculation formula was as follows: T/C (%)= $(T_{RTV}/C_{RTV}) \times 100\%$, $T_{RTV}$: RTV for treatment group; $C_{RTV}$: RTV for negative control group.

Results and Discussion

The experiment results were shown in Table 13. YNR-1 and CPT-11 (45 mg/kg) that were administered by intravenous injection once a week for three weeks has inhibited dramatically the growth of subcutaneously xenografted tumor in human colon cancer SW-620 nude mice. The anti-tumor effect of YNR-1 was better than CPT-11 at the same dose and administration scheme. After the treatment for one week on 6 tumor-bearing mice in each group, the tumors of 2 tumor-bearing mice in YNR-1 treatment group vanished completely and the tumor recrudesce was not observed even one week after stopping the drug use. The positive control, CPT-11 (15 mg/kg) which was intravenously administered once a week for three weeks has remarkably inhibited the growth of SW-620 subcutaneously xenografted tumor as well, with T/C value of 0.13%. The nude mice in each treatment group grew well during the whole experiment process, and the body weight increase surpassed the solvent control group.

TABLE 13

Treatment effects of PEGylation irinotecan on xenografted tumor of human colon cancer SW-620 nude mice in the experiment

| Group | Dosing, administration method | | No. of animal | | Body weight (g) | | TV (mm³, mean ± SD) | | RTV (mean ± SD) | T/C (%) |
|---|---|---|---|---|---|---|---|---|---|---|
| | | | Beginning | End | Beginning | End | $d_0$ | $d_{28}$ | | |
| Solvent control | 0.4 ml/mouse qw × 3w | iv | 12 | 12 | 19.4 | 19.9 | 132 ± 29 | 1920 ± 590(0) | 15.40 ± 6.40 | |
| CPT-11 | 15 mg/kg, q3w × 3w | iv | 6 | 6 | 19.7 | 24.2 | 133 ± 33 | 2.09 ± 1.51(0) | 0.02 ± 0.02**, | 0.13 |
| CPT-11 | 45 mg/kg, qw × 3w | iv | 6 | 6 | 18.8 | 21.8 | 132 ± 25 | 877 ± 324(0) | 6.60 ± 1.56* | 42.86 |
| YNR-1 | 45 mg/kg, qw × 3w | iv | 6 | 6 | 19.2 | 24.6 | 130 ± 43 | 0.37 ± 0.29(2) | 0.003 ± 0.002**,# | 0.02 |

Note:
t test, vs solvent control group, *p < 0.01, **p < 0.001; vs CPT-11 45 mg/kg group, #p < 0.001, "( )" was the number of animals with vanished tumor

The invention claimed is:

1. A conjugate of water soluble polymer-amino acid oligopeptide-drug of Formula (I) below:

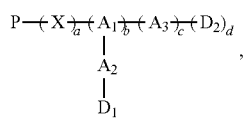

Formula (I)

wherein P is a water soluble polymer;

X is a linking group, wherein the linking group links P and $A_1$;

each of $A_1$ is independently same or different amino acid residue or amino acid analogue;

each of $A_2$ and $A_3$ is independently alanine or valine;

each of $D_1$ and $D_2$ is independently same or different drug molecule;

a is 0 or 1;

b is an integer of 2-12;

c is an integer of 0-7; and d is 0 or 1.

2. The conjugate according to claim 1, wherein P is selected from the group consisting of polyethylene glycol (PEG), polypropylene glycol, poly(glutamic acid), poly(aspartic acid), polyvinylpyrrolidone, polyvinyl alcohol, polypropylene morpholine, glucan, carboxymethylcellulose and analogue or copolymer thereof.

3. The conjugate according to claim 2, wherein P is PEG and the molecular weight of the PEG is 300-60,000 Daltons.

4. The conjugate according to claim 3, wherein the molecular weight of the PEG is 20,000-40,000 Daltons.

5. The conjugate according to claim 4, wherein the PEG is linear, Y shape branched or multi-arm PEG.

6. The conjugate according to claim 2, wherein the PEG has a structure shown in Formula (II) below:

$R_1$—O—(CH$_2$CH$_2$O)$_e$    Formula (II), wherein $R_1$ is $C_{1-12}$ alkyl, $C_{1-12}$ heteroalkyl, hydrogen or arylalkyl; and e is an integer of 10-1,500.

7. The conjugate according to claim 1, wherein P has a structure shown in Formula (III) below:

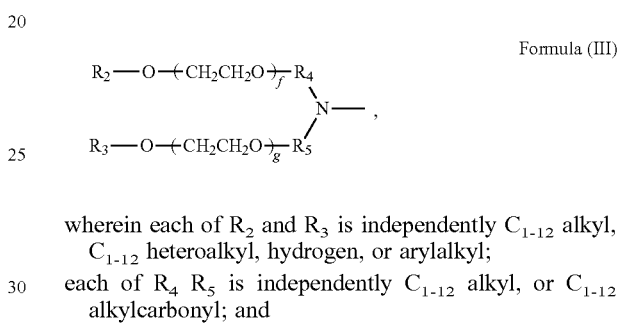

Formula (III)

wherein each of $R_2$ and $R_3$ is independently $C_{1-12}$ alkyl, $C_{1-12}$ heteroalkyl, hydrogen, or arylalkyl;

each of $R_4$ $R_5$ is independently $C_{1-12}$ alkyl, or $C_{1-12}$ alkylcarbonyl; and each of f and g is independently an integer of 10-1,500.

8. The conjugate according to claim 7, wherein $R_2$ and $R_3$ are methyl, $R_4$ is ethyl, and $R_5$ is methylenecarbonyl.

9. The conjugate according to claim 1, wherein P has a structure shown in Formula (IV) below:

Formula (IV), wherein $R_6$ is pentaerythritol, methylglucoside, sucrose, diethylene glycol, propanediol, glycerol or polyglycerol whose hydrogen in hydroxyl group is removed; i is 3, 4, 6 or 8; and h is an integer of 10-1,500.

10. The conjugate according to claim 1, wherein X is (CH$_2$)$_n$, (CH$_2$)$_n$CO, (CH$_2$)$_n$OCO, (CH$_2$)$_n$NHCO, —S—, —SO$_2$—, or —SO$_4$—; and n is an integer of 1-12.

11. The conjugate according to claim 10, wherein X is CH$_2$CO.

12. The conjugate according to claim 1, wherein $A_1$ is an amino acid residue or an amino acid analogue with at least two carboxylic groups and one amino group.

13. The conjugate according to claim 12, wherein $A_1$ has a structure shown in Formula (V) below:

Formula (V)

wherein $R_7$ is $C_{1-20}$ alkyl or $C_{1-20}$ heteroalkyl.

14. The conjugate according to claim 12, wherein $A_1$ has a structure shown in Formula (VI) below:

Formula (VI)

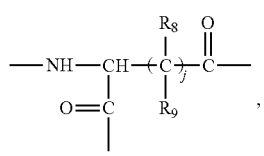

wherein each of $R_8$ and $R_9$ is independently hydrogen, $C_{1-12}$ alkyl, $C_{1-12}$ heteroalkyl, aryl, heteroaryl, aralkyl, or heteroarylalkyl, and $R_8$ and $R_9$ in each repeat unit are same or different; and j is an integer of 1-10.

15. The conjugate according to claim 12, wherein $A_1$ is an aspartic acid residue or glutamic acid residue.

16. The conjugate according to claim 1, wherein $A_2$ and $A_3$ are valine.

17. The conjugate according to claim 1, wherein each of $D_1$ and $D_2$ is independently an anti-tumor drug.

18. The conjugate according to claim 17, wherein the anti-tumor drug forms peptide or ester bond with $A_2$ or $A_3$.

19. The conjugate according to claim 17, wherein the anti-tumor drug is dasatinib, rapamycin, irinotecan, imatinib, erlotinib, gefitinib, lapatinib, sorafenib, sunitinib, paclitaxel, camptothecin, cinobufagin, glycyrrhetinic acid, or scopoletin.

20. The conjugate according to claim 19, wherein the anti-tumor drug is dasatinib.

21. The conjugate according to claim 1, wherein the conjugate has a structure shown in Formulas (IX), (X), or (XI) below:

Formula (IX)

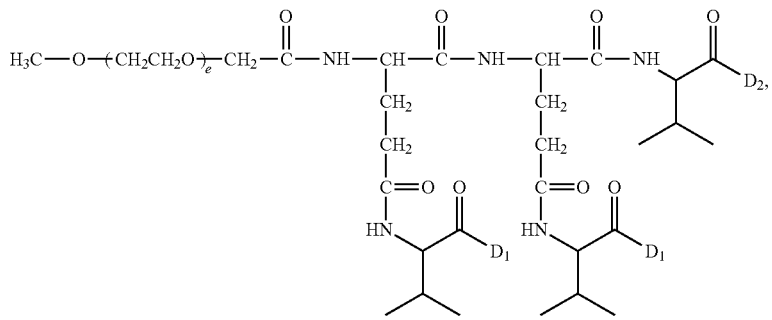

Formula (X)

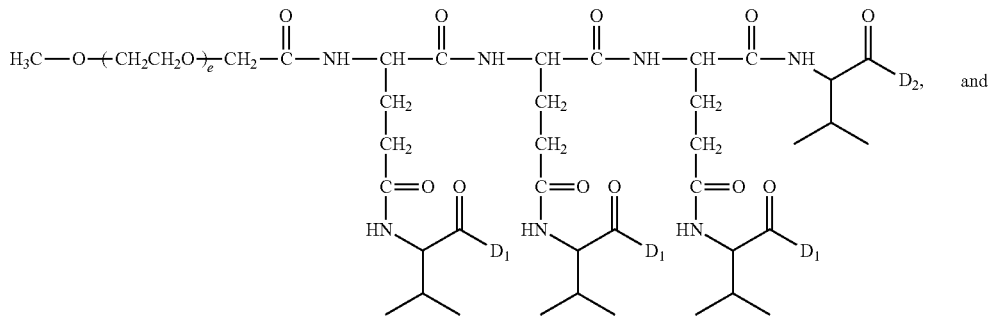

and

Formula (XI)

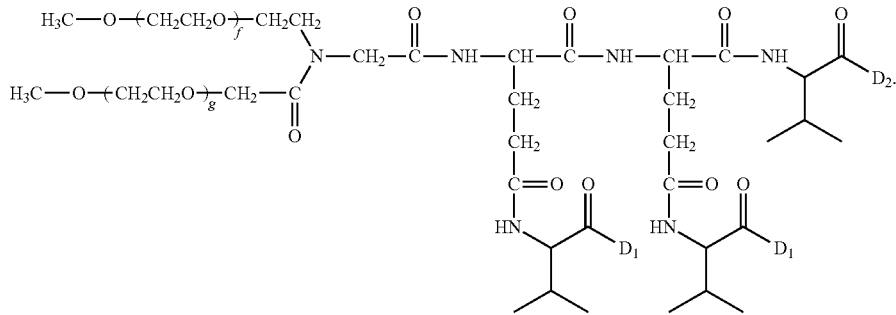

wherein each of e, f and g is independently an integer of 10-1,500; and wherein $D_1$ and $D_2$ are the same drug.

22. The conjugate according to claim 21, wherein $D_1$ and $D_2$ are dasatinib.

23. A pharmaceutical composition comprising the conjugate according to claim 1 and a pharmaceutically acceptable carrier or excipient.

24. The pharmaceutical composition according to claim 23, wherein the pharmaceutical composition is in the form of tablet, capsule, pill, granules, powder, suppository, injection, solution, suspension, ointment, patch, lotion, drop, liniment, or spray.

* * * * *